(12) United States Patent
Hayes et al.

(10) Patent No.: US 9,838,836 B2
(45) Date of Patent: Dec. 5, 2017

(54) PATIENT SUPPORT APPARATUS COMMUNICATION SYSTEMS

(71) Applicant: Stryker Corporation, Kalamazoo, MI (US)

(72) Inventors: Michael Joseph Hayes, Kalamazoo, MI (US); Anuj K. Sidhu, Kalamazoo, MI (US); Jonathan Mark Greenbank, Plainwell, MI (US); Aaron Douglas Furman, Kalamazoo, MI (US); Richard C. Mayoras, Jr., Kalamazoo, MI (US); David Terrance Becker, Grand Rapids, MI (US)

(73) Assignee: Stryker Corporation, Kalamazoo, MI (US)

( * ) Notice: Subject to any disclaimer, the term of this patent is extended or adjusted under 35 U.S.C. 154(b) by 259 days.

(21) Appl. No.: 14/559,458

(22) Filed: Dec. 3, 2014

(65) Prior Publication Data

US 2015/0082542 A1 Mar. 26, 2015

Related U.S. Application Data

(63) Continuation-in-part of application No. 13/802,855, filed on Mar. 14, 2013, which is a (Continued)

(51) Int. Cl.
*A61G 7/018* (2006.01)
*A61G 7/012* (2006.01)
(Continued)

(52) U.S. Cl.
CPC ............. *H04W 4/02* (2013.01); *A61G 7/018* (2013.01); *A61G 7/012* (2013.01); *A61G 7/015* (2013.01);
(Continued)

(58) Field of Classification Search
CPC .... A61G 7/018; A61G 2203/46; G06F 19/327
See application file for complete search history.

(56) References Cited

U.S. PATENT DOCUMENTS 5,062,151 A 10/1991 Shipley
5,699,038 A 12/1997 Ulrich et al.
(Continued)

FOREIGN PATENT DOCUMENTS

EP 1199027 A2 4/2002
EP 1623666 B1 12/2009
(Continued)

*Primary Examiner* — Eric J Kurilla
(74) *Attorney, Agent, or Firm* — Warner Norcross & Judd LLP

(57) ABSTRACT

A location detection system for person support apparatuses includes multiple network wireless access points that communicate with a plurality of mobile transceivers positioned on board the person support apparatuses. Based upon signal strength data (e.g. RSSI or RCPI) of messages from the access points to the transceivers, the locations of the person support apparatuses are determined. In some embodiments, the person support apparatuses include an additional location detection system that utilizes fixed locators having short range transceivers to generate a second location determination of the person support apparatuses. In still other embodiments, the person support apparatuses utilize the second location detection system to determine the location of the wireless access points. The person support apparatuses may also broadcast their location to other devices that then utilize the received signal strengths of those messages to determine their own location.

25 Claims, 25 Drawing Sheets

Related U.S. Application Data continuation-in-part of application No. 13/680,699, filed on Nov. 19, 2012, now Pat. No. 8,674,826, which is a continuation of application No. 13/356,204, filed on Jan. 23, 2012, now Pat. No. 8,319,633, which is a continuation of application No. 12/573,545, filed on Oct. 5, 2009, now Pat. No. 8,102,254, which is a continuation of application No. 11/277,838, filed on Mar. 29, 2006, now Pat. No. 7,598,853.

(60) Provisional application No. 61/640,138, filed on Apr. 30, 2012, provisional application No. 60/665,955, filed on Mar. 29, 2005, provisional application No. 60/734,083, filed on Nov. 7, 2005.

(51) Int. Cl.
*G06F 19/00* (2011.01)
*H04W 4/02* (2009.01)
*A61G 7/015* (2006.01)

(52) U.S. Cl.
CPC ...... *A61G 2203/12* (2013.01); *A61G 2203/42* (2013.01); *A61G 2203/46* (2013.01); *A61G 2205/60* (2013.01); *G06F 19/327* (2013.01); *G06F 19/328* (2013.01)

(56) References Cited

U.S. PATENT DOCUMENTS

| | | | |
|---|---|---|---|
| 5,917,425 A | 6/1999 | Crimmins et al. | |
| 6,017,354 A | 1/2000 | Culp et al. | |
| 6,049,745 A * | 4/2000 | Douglas | G05D 1/0261 180/168 |
| 6,344,794 B1 * | 2/2002 | Ulrich | G06K 17/0022 340/539.13 |
| 6,612,985 B2 | 9/2003 | Eiffert et al. | |
| 7,319,386 B2 * | 1/2008 | Collins, Jr. | A61B 5/1115 340/286.07 |
| 7,399,205 B2 | 7/2008 | McNeely et al. | |
| 7,638,958 B2 | 12/2009 | Philipp et al. | |
| 7,746,218 B2 | 6/2010 | Collins, Jr. et al. | |
| 7,899,006 B2 | 3/2011 | Boyd | |
| 8,319,633 B2 | 11/2012 | Becker et al. | |
| 8,461,968 B2 | 6/2013 | Ball et al. | |
| 8,535,342 B2 | 9/2013 | Malackowski et al. | |
| 8,634,981 B1 * | 1/2014 | Hyde | A61G 1/0275 180/19.1 |
| 8,887,272 B2 | 11/2014 | Urness et al. | |
| 8,891,816 B2 * | 11/2014 | Billingham | G06K 9/00677 348/113 |
| 2002/0084903 A1 | 7/2002 | Chaco | |
| 2002/0145534 A1 | 10/2002 | Dempsey | |
| 2002/0167417 A1 | 11/2002 | Welles, II et al. | |
| 2002/0183979 A1 | 12/2002 | Wildman | |
| 2005/0035862 A1 * | 2/2005 | Wildman | A61B 5/1113 340/573.1 |
| 2006/0247847 A1 * | 11/2006 | Carter | A47F 10/04 701/498 |
| 2008/0205311 A1 * | 8/2008 | Perkins | A61B 5/6887 370/310 |
| 2009/0112630 A1 * | 4/2009 | Collins, Jr. | G06F 19/327 705/3 |
| 2010/0117823 A1 * | 5/2010 | Wholtjen | G06F 19/327 340/539.13 |
| 2011/0154569 A1 * | 6/2011 | Wiggers | A61B 6/0407 5/81.1 R |
| 2012/0029697 A1 * | 2/2012 | Ota | A61G 7/08 700/253 |
| 2013/0184003 A1 | 7/2013 | Alizadeh-Shabdiz et al. | |
| 2013/0244692 A1 | 9/2013 | Kelly et al. | |
| 2014/0184409 A1 * | 7/2014 | Vanderpohl, III | A61G 7/05 340/539.22 |
| 2015/0081335 A1 | 3/2015 | Dixon et al. | |
| 2015/0216746 A1 * | 8/2015 | Dirauf | G05D 1/0234 701/25 |

FOREIGN PATENT DOCUMENTS

| | | |
|---|---|---|
| WO | 0185085 A2 | 11/2001 |
| WO | 03105095 A2 | 12/2003 |
| WO | 2004093023 A2 | 10/2004 |
| WO | 2004104619 A1 | 12/2004 |

\* cited by examiner

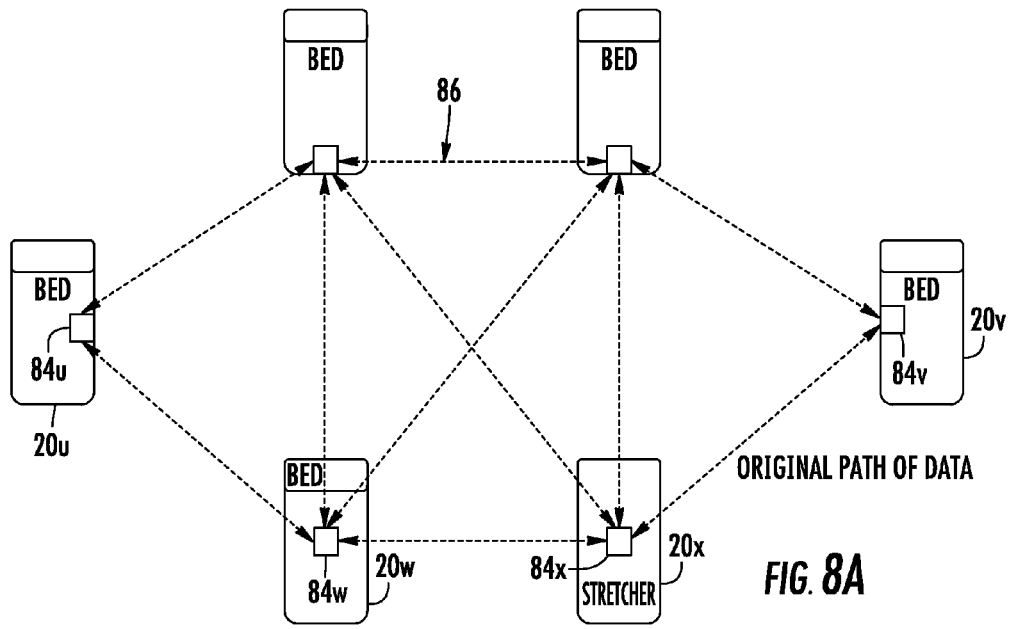
FIG. 8A — ORIGINAL PATH OF DATA
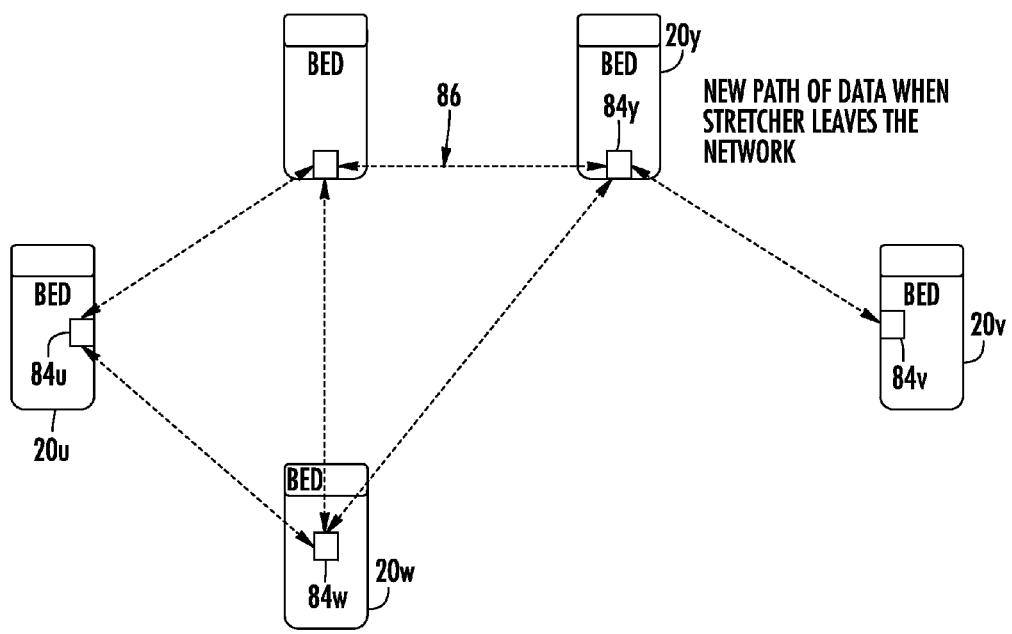
FIG. 8B — NEW PATH OF DATA WHEN STRETCHER LEAVES THE NETWORK

PATIENT SUPPORT APPARATUS COMMUNICATION SYSTEMS

CROSS-REFERENCE TO RELATED APPLICATIONS

This application is a continuation-in-part of U.S. patent application Ser. No. 13/802,855 filed Mar. 14, 2013 by inventors Michael Joseph Hayes et al. and entitled PATIENT SUPPORT APPARATUS COMMUNICATION SYSTEMS, which in turn claims priority to U.S. provisional patent application Ser. No. 61/640,138 filed Apr. 30, 2012 by applicants Michael Hayes et al. and entitled PATIENT SUPPORT APPARATUS COMMUNICATION SYSTEMS. The Ser. No. 13/802,855 patent application is also a continuation-in-part application of U.S. patent application Ser. No. 13/680,699, filed on Nov. 19, 2012, by David T. Becker, et al., entitled LOCATION DETECTION SYSTEM FOR A DEVICE, which is a continuation of U.S. patent application Ser. No. 13/356,204, filed Jan. 23, 2012, by David T. Becker, et al., entitled LOCATION DETECTION SYSTEM FOR A PATIENT HANDLING DEVICE, which issued on Nov. 27, 2012, which is a continuation of U.S. Pat. No. 8,102,254, which is a continuation of U.S. Pat. No. 7,598,853, which claims the benefit of U.S. provisional patent application Ser. No. 60/665,955, filed Mar. 29, 2005 and U.S. provisional patent application Ser. No. 60/734,083, filed Nov. 7, 2005. The subject matter of all of the aforementioned patents and patent applications is incorporated herein by reference.

BACKGROUND OF THE INVENTION

The subject matter of this application relates to location systems for medical facilities. Location detection systems are known in the art for tracking the location of personnel and equipment in a facility. These systems have been specifically adapted for use in facilities such as healthcare facilities for tracking healthcare professionals, e.g., nurses and physicians, and for tracking equipment, e.g., beds, patient monitoring devices, and the like. A typical location detection system is also referred to as an asset tracking system that utilizes tags that periodically transmit a unique identification signal. Receivers are located throughout the facility at known locations for receiving these identification signals. The receivers are wired to a central computer that processes the unique identification signals to determine a location of the asset associated with the tag.

The subject matter of the present application also relates to systems and methods by which person support apparatuses—such as, but not limited to, cots, stretchers, beds, chairs, recliners, operating tables—communicate with each other and with other structures.

SUMMARY OF THE INVENTION

The present invention provides systems and methods for determining the location of person support apparatuses. In some embodiments, the systems and methods allow a location of the person support apparatuses to be determined utilizing existing infrastructure of the healthcare facility, such as, but not limited to, wireless access points that are positioned at known locations throughout the healthcare facility. In some embodiments, the person support apparatuses communicate with each other and share location information. In still other embodiments, the person support apparatuses communicate with other devices and share location information with them. In still other embodiments, multiple technologies for determining the location of a person support apparatus are combined together.

In one embodiment, a location detection system is provided that includes a person support apparatus and a controller. The person support apparatus has a support surface and a wireless transceiver. The support surface is adapted to support a person thereon. The wireless transceiver wirelessly communicates with a plurality of access points of a computer network and receives messages from the plurality of access points. The controller generates a location estimate of the person support apparatus within a facility based upon signal strength data of the messages from the plurality of access points.

In other embodiments, the messages include a media access control (MAC) address for each of the access points.

The wireless transceiver communicates with the access points, in at least one embodiment, using a protocol that follows Institute of Electrical and Electronics Engineers (IEEE) standard 802.11.

In other embodiments, the location detection system further includes an infrared receiver adapted to receive an infrared signal from a fixed locator positioned off of the person support apparatus. The infrared signal includes a locator identifier unique to the fixed locator, and the wireless transceiver transmits the locator identifier to one of the access points.

In some embodiments, the controller is positioned on the person support apparatus, while in other embodiments the controller is positioned off the person support apparatus and on the computer network.

In still other embodiments, the wireless transceiver is further adapted to transmit the location estimate of the person support apparatus, as determined by the controller, to other devices. The other devices include other person support apparatuses and/or other medical devices.

According to another embodiment, a location detection system is provided that includes a person support apparatus, a processing station, and a controller. The person support apparatus includes a frame, a support surface adapted to support a person thereon, and a wireless transceiver adapted to wirelessly communicate with a plurality of access points of a computer network. The wireless transceiver is further adapted to receive messages from the plurality of access points. The processing station is located remotely from the person support apparatus and communicatively coupled to the computer network. The controller is located on board the person support apparatus and is adapted to send to the processing station signal strength data of the messages.

In some embodiments, the processing station is further adapted to access data indicating locations of each of the plurality of access points, and to generate a location estimate of the person support apparatus within a facility based upon the signal strength data and the data indicating locations of each of the plurality of access points.

The controller sends the signal strength data to the processing station using the wireless transceiver, in some embodiments, and the processing station includes map data indicating locations of the access points within the facility.

In still other embodiments, the system includes an infrared transceiver supported on the person support apparatus and adapted to transmit an interrogation signal, and a plurality of locators positioned at fixed locations. Each of the locators is adapted to wirelessly transmit a unique identifier in response to the interrogation signal from the infrared transceiver. The controller is adapted to send the unique identifier to the processing station and the processing station is adapted to generate a location estimate of the person support apparatus within a facility based upon the unique identifier.

In some embodiments, the processing station is further adapted to generate a location estimate of at least one of the access points based upon the location estimate of the person support apparatus and the signal strength data.

The processing station, in some embodiments, accesses data indicating locations of each of the plurality of access points, generates a first location estimate of the person support apparatus based upon the signal strength data and the data indicating locations of each of the plurality of access points, and generates a second location estimate of the person support apparatus based upon the unique identifier.

In some embodiments, the processing station is further adapted to generate a third location estimate of the person support apparatus by combining the first and second location estimates.

The processing station is also adapted to forward at least one of the first and second location estimates to a second processing station communicatively coupled to the computer network, in some embodiments. The processing station forwards the first location estimate to the second processing station if the person support apparatus is moving, and the processing station forwards the second location estimate to the second processing station if the person support apparatus is stationary and positioned adjacent to one of the locators. Still further, in some embodiments, the processing station forwards the first location estimate to the second processing station if the person support apparatus has a brake off, and the processing station forwards the second location estimate to the second processing station if the person support apparatus has the brake on.

The processing station is adapted to transmit the location estimate to the person support apparatus, in some embodiments. In some embodiments, the controller is adapted to transmit the location estimate of the person support apparatus wirelessly to another device.

According to another embodiment, a person support apparatus is provided that includes a frame, a support surface adapted to support a person thereon, a first wireless transceiver, a second wireless transceiver, and a controller. The first wireless transceiver is adapted to wirelessly communicate with a plurality of access points of a computer network and to receive messages from the plurality of access points. The second wireless transceiver is adapted to wirelessly communicate with a locator positioned at a fixed location within a facility and to receive a unique identifier from the locator. The controller is adapted to generate a location estimate of the person support apparatus within the facility based upon signal strength data of the messages and/or the unique identifier.

The controller is further adapted to transmit the location estimate to a processing station located remotely from the person support apparatus and communicatively coupled to the computer network, in some embodiments.

The controller, in some embodiments, bases the location estimate of the person support apparatus upon the signal strength data when a brake on the person support apparatus is off.

According to other embodiments, a person support apparatus is provided that includes a frame, a support surface, a first wireless transceiver, a second wireless transceiver, and a controller. The first wireless transceiver is adapted to wirelessly communicate with a plurality of access points of a computer network and to receive messages from the plurality of access points. The second wireless transceiver is adapted to wirelessly communicate with a locator positioned at a fixed location within a facility and to receive a unique identifier from the locator. The controller is adapted to generate a location estimate of at least one of the access points of the computer network based upon the unique identifier.

In other embodiments, the person support apparatus includes a memory in which map data indicating a location of the locator is stored, and the controller uses the map data and signal strength data of the messages when generating the location estimate of the at least one of the access points.

In some embodiments, the controller is further adapted to wirelessly receive location data from another person support apparatus that is in communication with the at least one of the access points. The controller uses the location data in generating the location estimate of the at least one of the access points.

In other embodiments, the controller is further adapted to wirelessly transmit the location estimate to another person support apparatus that is in communication with the at least one of the access points.

In any of the embodiments disclosed herein, the person support apparatus may be one of a bed, a stretcher, a cot, a recliner, and/or a chair, and the computer network may be an Ethernet-based computer network.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 8A is a plan view of a mesh network arrangement of a plurality of patient support apparatuses wherein a potential data path from a first patient support apparatus to an access point of a healthcare network is highlighted;

FIG. 8B is a plan view of the mesh network of FIG. 8A shown with one patient support apparatus removed and an alternative data path for transmitting data from the first patient support apparatus to the access point of the healthcare network;

DETAILED DESCRIPTION OF THE EMBODIMENTS

Figure 1:
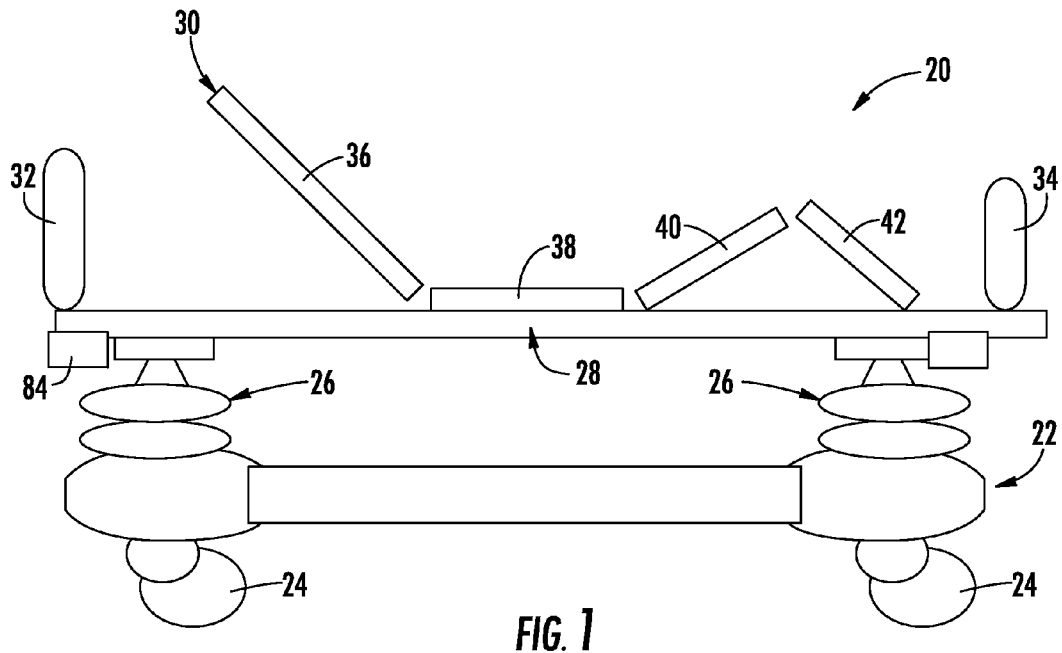
FIG. 1 is side elevation diagram of a patient support apparatus into which one or more of the features of the present invention may be incorporated.

A patient support apparatus 20 that may incorporate one or more of the aspects of the present invention is shown in FIG. 1. Patient support apparatus 20 may be a cot, a stretcher, a bed, a recliner, an operating table, or any other type of structure used to support a patient in a healthcare setting. In general, patient support apparatus 20 includes a base 22 having a plurality of wheels 24, a pair of elevation adjustment mechanisms 26 supported on said base, a frame 28 supported on said elevation adjustment mechanisms, and a patient support deck 30 supported on said frame. Patient support apparatus 20 further includes a headboard 32 and a footboard 34.

Base 22 includes a brake (not shown) that is adapted to selectively lock and unlock wheels 24 so that, when unlocked, patient support apparatus 20 may be wheeled to different locations. Elevation adjustment mechanisms 26 are adapted to raise and lower frame 28 with respect to base 22. Elevation adjustment mechanisms 26 may be hydraulic actuators, electric actuators, or any other suitable device for raising and lowering frame 28 with respect to base 22. In some embodiments, elevation adjustment mechanisms 26 are operable independently so that the orientation of frame 28 with respect to base 22 can also be adjusted.

Frame 28 provides a structure for supporting patient support deck 30, headboard 32, and footboard 34. Patient support deck 30 provides a surface on which a mattress (not shown), or other soft cushion is positionable so that a patient may lie and/or sit thereon. Patient support deck 30 is made of a plurality of sections, some of which are pivotable about generally horizontal pivot axes. In the embodiment shown in FIG. 1, patient support deck 30 includes a head section 36, a seat section 38, a thigh section 40, and a foot section 42. Head section 36, which is also sometimes referred to as a Fowler section, is pivotable between a generally horizontal orientation (not shown in FIG. 1) and a plurality of raised positions (one of which is shown in FIG. 1). Thigh section 40 and foot section 42 may also be pivotable, such as is shown in FIG. 1.

Although not illustrated in the patient support apparatus 20 depicted in FIG. 1, patient support apparatus will sometimes include a plurality of siderails (not shown) coupled to frame 28. If patient support apparatus 20 is a bed, there are typically four such siderails, one positioned at a left head end of frame 28, a second positioned at a left foot end of frame 28, a third positioned at a right head end of frame 28, and a fourth positioned at a right foot end of frame 28. If patient support apparatus 20 is a stretcher or a cot, there are typically fewer siderails. In other embodiments, there are no siderails on patient support apparatus 20. Regardless of the number of siderails, such siderails are movable between a raised position in which they block ingress and egress into and out of patient support apparatus 20, and a lowered position in which they are not an obstacle to such ingress and egress.

The construction of any of base 22, elevation adjustment mechanisms 26, frame 28, patient support deck 30, headboard 32, footboard 34, and/or the siderails may be the same as disclosed in commonly assigned, U.S. Pat. No. 7,690,059 issued to Lemire et al., and entitled HOSPITAL BED, or as disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION; or as disclosed in the Stryker Maintenance Manual for the Model 3002 S3 MedSurg Bed, available from Stryker Corporation of Kalamazoo, Mich., the disclosures of all three of these which are incorporated herein by reference. The construction of any of base 22, elevation adjustment mechanisms 26, frame 28, patient support deck 30, headboard 32, footboard 34 and/or the siderails may also take on forms different from what is disclosed in the aforementioned documents.

Patient support apparatus 20 of FIG. 1 further includes a mesh network node 84 that allows apparatus 20 to form an ad hoc electrical communications network with one or more other patient support apparatuses 20 and/or one or more medical devices. Each of the other patient support apparatuses 20 and/or medical devices includes similar electronics that form a mesh network node that is able to communicate with node 84, as well as any other nodes 84 on other apparatuses 20 or medical devices that are within communication range. Each node 84—whether positioned on a patient support apparatus 20, a medical device, or something else—is therefore able to not only disseminate data that originates from the structure to which it is coupled, but also to serve as a relay for forwarding information it receives from other nodes onto to still other nodes, or onto a healthcare network 70 (FIG. 10), as will be described in greater detail below. Further, because the positions of patient support apparatus 20, as well as medical devices and other structures, are likely to change over time, the mesh network formed by the nodes 84 is dynamic such that the data paths change with changing locations and/or other conditions.

Figure 2:
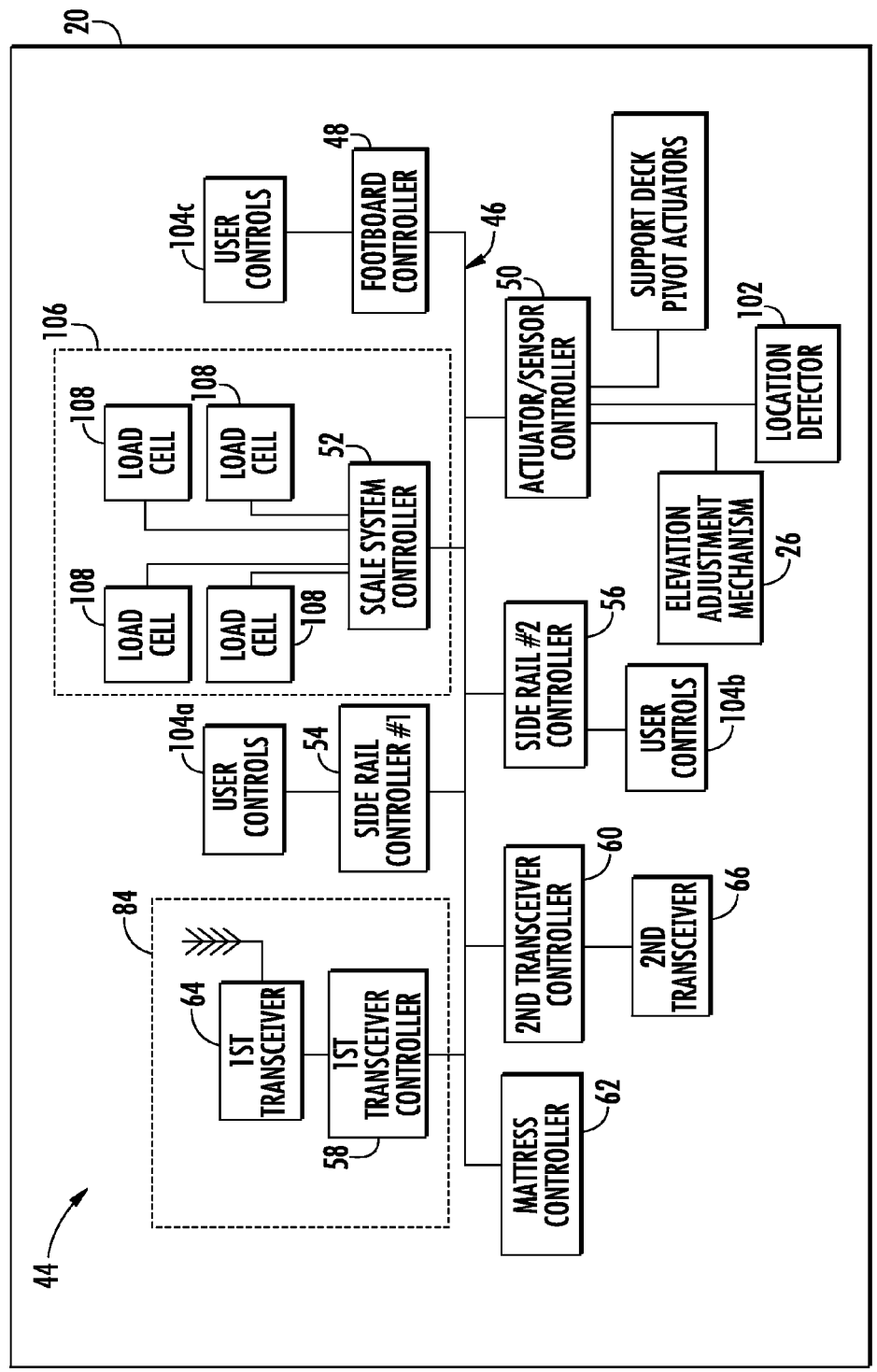
FIG. 2 is a diagram of one embodiment of an electrical control system that may be used with the patient support apparatus of FIG. 1, or with any of the other patient support embodiments described herein.

FIG. 2 illustrates one embodiment of an electrical control system 44 that is incorporated into patient support apparatus 20. Electrical control system 44 includes, in the illustrated embodiment, an internal communications network 46. Internal communications network 46 is a Controller Area Network, although it will be understood by those skilled in the art that it could be another type of network, such as, but not limited to, a CANOpen network, DeviceNet network, other networks having a CAN physical and data link layer), a LONWorks network, a Local Interconnect Network (LIN), a FireWire network, or any other known network for communicating messages between electronic structures on patient support apparatus. Internal communications network 46 includes a number of controllers or internal nodes that are in communication with each other over the internal network 46. These include a footboard controller 48, an actuator/sensor controller 50, a scale system controller 52, a first side rail controller 54, a second side rail controller 56, a first transceiver controller 58, a second transceiver controller 60, and a mattress controller 62. Before describing in further detail the structure and functions of these controllers, it should be pointed out that patient support apparatus 20 could alternatively be designed without any internal communications network, but instead have various controllers communicate with each other in a non-networked manner, or by combining the functions of these various controllers into one controller that handles all of these tasks, or in still other manners that do not utilize any sort of communications network on the patient support apparatus 20.

Each controller that communicates over internal communications network 46 includes one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art.

In the embodiment of FIG. 2, the electrical control system 44 of patient support apparatus 20 includes a first transceiver 64 that is electrically and communicatively coupled to a first transceiver controller 58, as well as a second transceiver 66 that is electrically and communicatively coupled to second transceiver controller 60. It will be understood by those skilled in the art that the use of the terms "first transceiver" and "second transceiver" herein has been done for communicative convenience, and that in no way do the "first" and "second" labels connote any significance to, or ranking of, the respective transceivers, nor are they intended to suggest a limit to the number of transceivers that may be present on a given patient support apparatus 20.

First transceiver controller 58 is adapted to process messages that are communicated on electrical communications network 46 that are intended for first transceiver controller 58. Such messages will typically, although not exclusively, include messages containing data that is meant to be transmitted off of patient support apparatus 20 via first transceiver 64. Similarly, second transceiver controller 60 is adapted to process messages that are communicated on electrical communications network 46 that are intended for second transceiver controller 60. Such messages will typically, although not exclusively, include messages containing data that is meant to be transmitted off of patient support apparatus 20 via second transceiver 66. First and second transceiver controllers 58 and 60 are further adapted to process messages received by first and second transceivers 64 and 66, respectively, and, where applicable, forward the content of those messages onto internal communications network 46 for sharing with one or more of the various controllers on network 46.

Together, first transceiver 64 and first transceiver controller 58 form mesh network node 84. Transceiver 64 therefore receives messages and/or signals from other transceivers that are meant to be forwarded off of patient support apparatus 20, rather than consumed by patient support apparatus 20. Controller 58 processes the received messages sufficiently to determine whether the messages are for internal consumption or whether they are to be relayed onto another recipient. Messages that are to be relayed are temporarily stored in memory that is accessible to controller 58 until such messages have been successfully forwarded onto another recipient. Messages that are to be consumed by patient support apparatus 20 are processed by controller 58 and directly delivered to the appropriate device on patient support apparatus 20 by hardwire or other direct connection, or their content is distributed via internal communications network 46 for use by one or more of the controllers on network 46.

In one embodiment of patient support apparatus 20, first and second transceivers 64 and 66 are different types of transceivers. That is, each transceiver is adapted to transmit and receive electrical signals using two different communication protocols. For example, in one embodiment, first transceiver 64 is adapted to transmit and receive wireless electrical signals using the ZigBee protocol, or the IEEE 802.15.4 protocol, while the second transceiver 66 is adapted to transmit and receive wireless electrical signals using the Wi-Fi protocol, or the IEEE 802.11 protocol. In other embodiments, first transceiver 64 uses the ZigBee or IEEE 802.15.4 protocol while second transceiver 66 is adapted to transmit and receive electrical signals over a wire or cable connected to patient support apparatus 20. Such a wire or cable may constitute a universal serial bus (USB) connection, or it may include an RS-232 or RS-485 connection, or it may include a wired Ethernet cable. In still other embodiments, still other communication protocols are used instead of those listed herein, whether wired or wireless, including, but not limited to, infrared communication, Bluetooth communication, and other types of communication.

Regardless of the specific communications format used, first transceiver 64 is designed to communicate with one or more nearby structures, such as, but not limited to, medical devices, sensing systems, and/or with other patient support apparatuses. First transceiver 64 therefore sends messages to and receives messages from medical devices equipped with transceivers that are compatible with first transceiver 64, and/or it sends messages to and receives messages from sensing systems equipped with compatible transceivers, and/or it sends messages to and receives messages from other first transceivers positioned on one or more other patient support apparatuses.

If communicating with another patient support apparatus, the other patient support apparatus need not be identical to patient support apparatus 20, but instead merely has to be able to have the ability to send and receive messages using the same protocol used by first transceiver 64. Thus, in some situations, if patient support apparatus 20 is a bed, it is able to communicate via first transceiver 64 with a stretcher, or with a cot, or a recliner, or some other type of patient support apparatus that is of a different physical type than a bed. Further, even if the other patient support apparatus is a bed, it need not be constructed in the same manner as patient support apparatus 20. It may be a different model of bed in some cases, or it may be made by a different manufacturer in some cases, or it may be of the exact same type of bed as patient support apparatus 20. The same is true if patient support apparatus 20 is a cot, a stretcher, a recliner, or something else—the other patient support apparatuses to which it communicates via first transceiver 64 may be the same or a different type of patient support apparatus.

Figure 7:
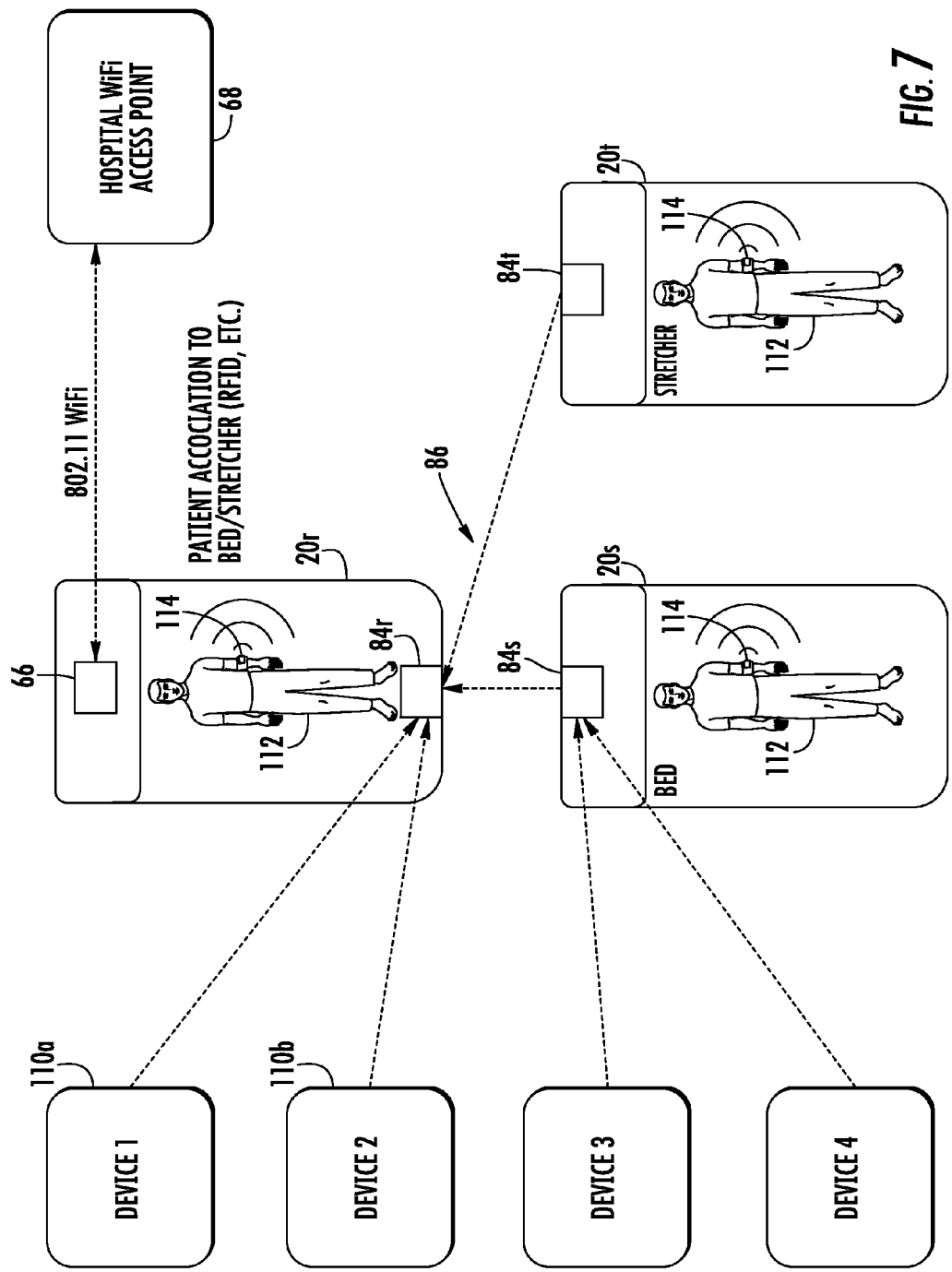
FIG. 7 is a plan view of a plurality of patient support apparatuses that are configured to receive data from one or more medical devices positioned within the vicinity of the patient support apparatuses, and to forward said data to a healthcare network access point.
Figure 10:
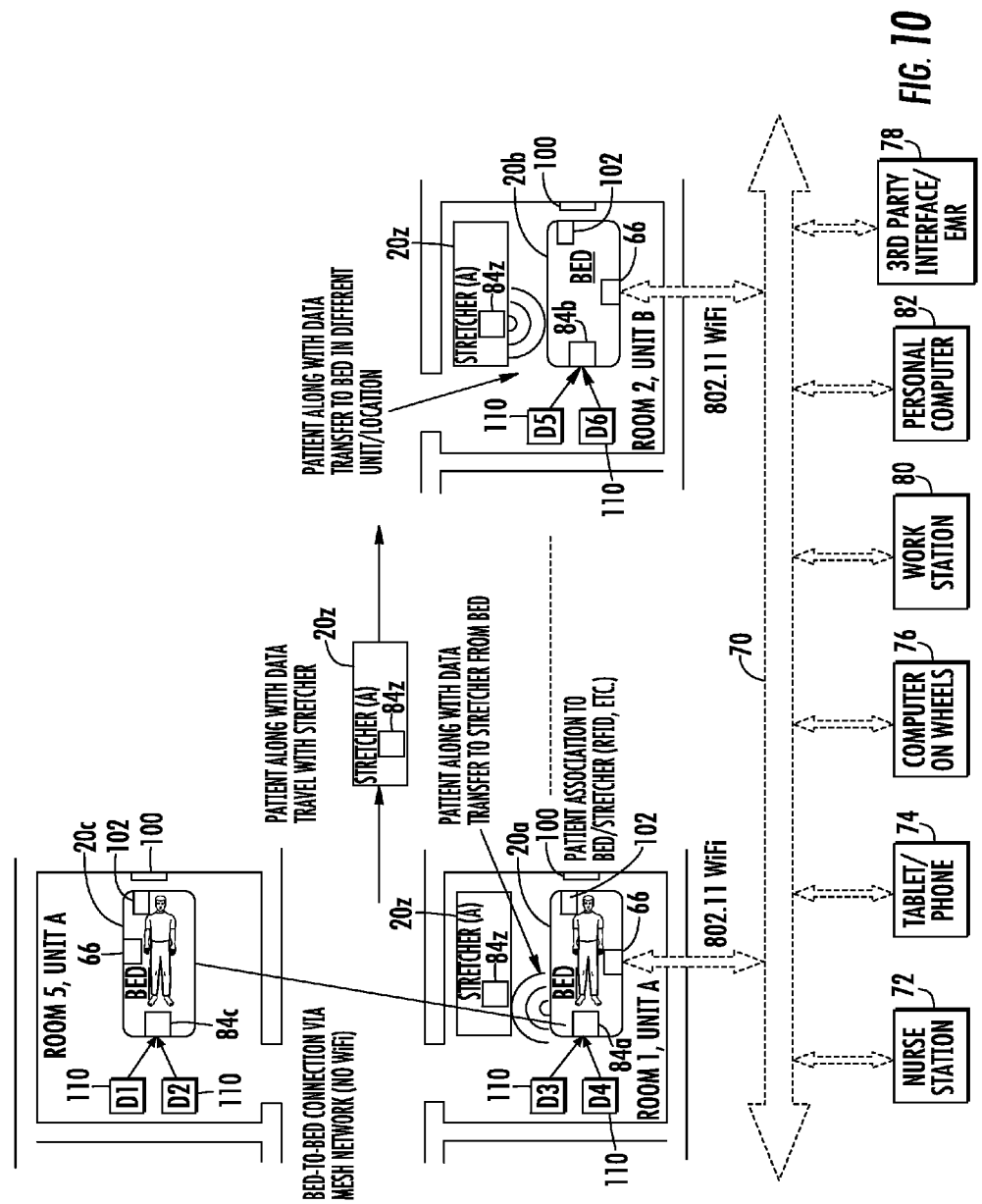
FIG. 10 is a plan view diagram of an arbitrary portion of a floor plan of a healthcare facility showing patient support apparatuses that are configured to wirelessly receive and transmit medical data, patient data, and other signals from other patient support apparatuses.

As noted, in some embodiments, first transceiver 64 is also configured to communicate with one or more medical devices 110 (see, e.g. FIG. 7 or 10). Such medical devices include any medical devices that are usable in a healthcare setting in a patient's room, or otherwise within a nearby vicinity of a patient positioned on a patient support apparatus 20. A non-exhaustive list of such potential medical devices includes ventilators, vital signs monitors, respirators, infusion pumps, IV pumps, temperature sensors, and/or blood oxygen saturation monitors. When communicating with these medical devices, first transceiver 64 and its associated controller 58—which together form one mesh network node 84—become part of a mesh network that includes other nodes 84. In such cases, node 84 of support apparatus 20 is able to relay information received from the medical devices 110 onto a healthcare communication network 70. This relay is able to take place via different routes. First, the relay of information may take place via a direct connection between the support apparatus 20 and network 70, or this relay of information may be routed through one or more other support apparatuses 20 before it is delivered to network 70. These alternative routes are selected by the nodes 84 and intelligence shared between them regarding signal strength, traffic, and/or other factors, as will be discussed more below.

In still other embodiments, first transceiver 64 of patient support apparatus 20 is configured to communicate with sensing systems that are used to sense one or more characteristics, features, conditions, and/or states of the caregiver, the patient, or other personnel. For example, in one embodiment, such a sensing system includes an interface pressure sensing sheet position on top of a mattress on the patient support apparatus 20, such as disclosed in commonly assigned U.S. patent application serial number PCT/US12/27402 filed Mar. 2, 2012 by applicants Balakrishnan et al., and entitled SENSING SYSTEM FOR PATIENT SUPPORTS, the complete disclosure of which is incorporated herein by reference. In such an embodiment, first transceiver 64 is configured to communicate with any one or more of the sensor array 22, the controller 24, the user interface 26, the sensor controller 28, and/or the tablet 44 disclosed in the PCT/US12/27402 patent application. The data from the interface pressure sensing system is forwarded via mesh network node 84 of patient support apparatus 20 onto healthcare network 70, either directly from support apparatus 20, or via one or more additional support apparatuses 20 or other types of intermediate mesh network nodes 84. Still further, in some embodiments, the data from the interface pressure sensing system is partially or wholly consumed by patient support apparatus 20, or a device positioned on patient support apparatus 20.

In another embodiment, first transceiver 64 is configured to communicate with a video monitoring system, such as that disclosed in commonly assigned U.S. patent application Ser. No. 13/242,022 filed Sep. 23, 2011 by applicants Derenne et al. and entitled VIDEO MONITORING SYSTEM, the complete disclosure of which is hereby incorporated herein by reference. In such an embodiment, first transceiver 64 is configured to communicate with any one or more of the cameras 22, computer devices 24, and/or image projectors 30 disclosed in the Ser. No. 13/242,022 patent application. The data from the video system and/or cameras is forwarded via mesh network node 84 of patient support apparatus 20 onto healthcare network 70, either directly from support apparatus 20, or via one or more additional support apparatuses 20 or other types of intermediate mesh network nodes 84. Still further, in some embodiments, the data from the video monitoring system is partially or wholly consumed by patient support apparatus 20, or a device positioned on patient support apparatus 20.

In still another embodiment, first transceiver 64 is configured to communicate with hand washing stations, or other devices, such as disclosed in commonly assigned U.S. patent application Ser. No. 13/570,934, filed Aug. 9, 2012, by applicants Hayes et al., and entitled PATIENT SUPPORT APPARATUS WITH IN-ROOM DEVICE COMMUNICATION, the complete disclosure of which is hereby incorporated herein by reference. In such an embodiment, first transceiver 64 is configured to communicate with any of the electronic tags 24 (e.g. mobile tags 24a, stationary tags 24b, and patient tags 24c) and/or the transceiver 52 disclosed in the Ser. No. 13/570,934 application. The data from the hand washing station, or other device, is forwarded via mesh network node 84 of patient support apparatus 20 onto healthcare network 70, either directly from support apparatus 20, or via one or more additional support apparatuses 20 or other types of intermediate mesh network nodes 84. Still further, in some embodiments, the data from the hand washing station is partially or wholly consumed by patient support apparatus 20, or a device positioned on patient support apparatus 20. In yet other embodiments, the patient hand washing station is configured to be, or include, a mesh network node itself, in which case the hand washing station may be the recipient of data relayed off of patient support apparatus 20 that is destined for communication to healthcare network 70.

In still other embodiments, first transceiver 64 is configured to communicate with any combination of the devices disclosed herein, including, but not limited to, any of those disclosed in the patent references incorporated herein by reference. Still further, patient support apparatus 20 may be modified to include a third or fourth transceiver that, instead of, or in addition to, first transceiver 64, communicates with any of the devices disclosed herein, including, but not limited to, any of those disclosed in the patent references incorporated herein by reference.

Second transceiver 66, as noted earlier, is configured to communicate with one or more wireless access points 68 of a healthcare communications network 70. An example of one such communications network 70 is shown in FIG. 10. Such a network is often an Ethernet network, although it may use other networking communication protocols. The devices, applications, and/or servers that are coupled to the network 70 will vary from facility to facility because they will be dependent upon a particular healthcare institution's choice of what third-party software and/or systems they have installed on their network. In the illustrative embodiment shown in FIG. 10, network 70 includes a plurality of nurses stations 72, tablet and/or phones 74, computers on wheels (COW) 76, work stations 80, and one or more personal computers 82. An electronic medical records (EMR) server or system 78 may also be included. As noted, network 70 may further include one or more additional devices, applications, and/or servers, or it may include one or fewer devices, applications, and/or servers, depending upon the particular configuration that has been implemented at a particular healthcare facility. Such additional devices, applications, and/or servers may include an Admission, Discharge, and Transfer (ADT) system that manages the admission, discharge, and transfer of patients in the healthcare facility; a workflow server that manages the work assignments of caregivers in the healthcare facility; and/or wireless alerting system that automatically forwards alarms and alerts to appropriate healthcare personnel via wireless communication technology. Such wireless communication technology may include the forwarding of alerts via cell phones, WIFI devices, pagers, personal digital assistants (PDAs), or by other means. Any information that is transmitted to network 70 via one or more of the mesh network nodes 84 may therefore cause an alert to be forwarded to the appropriate caregiver(s), depending upon the contents of such information. The nurses station 72, tablets 74, computers on wheels 76, work stations 80, personal computers 82, electronic medical record systems 78, ADT systems, work flow systems, and wireless alerting systems may all be conventional products that are commercially available from one or more different suppliers, as would be known to one of ordinary skill in the art.

Figure 3:
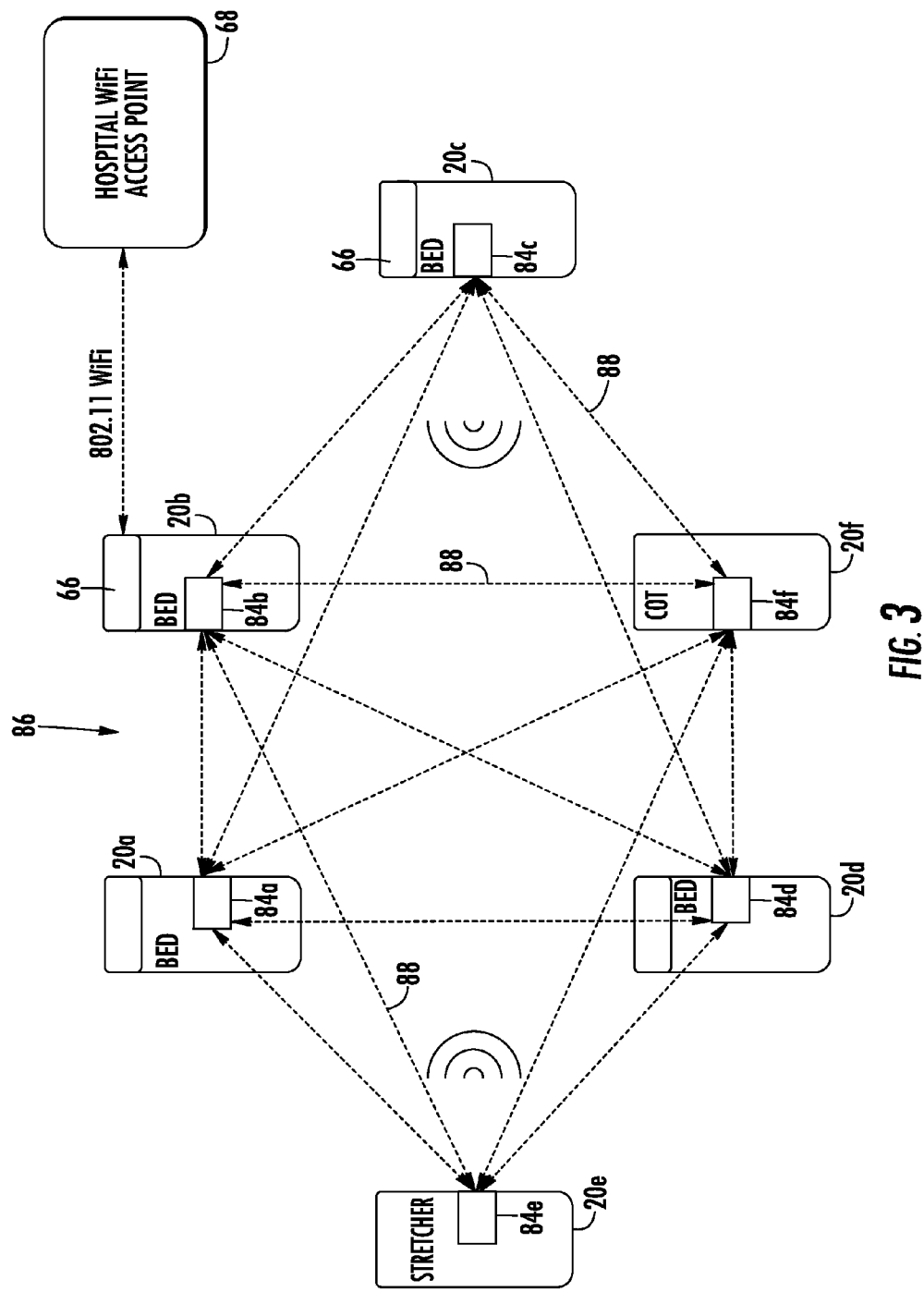
FIG. 3 is a plan view diagram of a plurality of patient support apparatuses according to one embodiment showing a mesh network that enables the patient support apparatuses to communicate with each other and/or an access point of a healthcare network.

FIG. 3 illustrates an arbitrary example of a mesh network 86 that created by a plurality of patient support apparatuses and their respective mesh network nodes 84. In the example shown, the mesh network 86 includes four patient support apparatuses 20 that are beds (20a, 20b, 20c, and 20d), one patient support apparatus 20 that is a stretcher (20e), and one patient support apparatus 20 that is a cot (20f). Each patient support apparatus 20 includes a mesh network node 84 that comprises first transceiver 64 and first transceiver controller 58. Each node 84 broadcasts signals that are responded to by all of the other nodes that are sufficiently close to receive the broadcasted signals. This broadcasting and responding enables each patient support apparatus 20 to determine what other patient support apparatuses 20 are within communication distance. When responding to such broadcasts, a node 84 also responds with information identifying what nodes 84 it itself is in communication distance with. For example, if stretcher 20e sends out an initial broadcast, beds 20a, 20b, and 20d, along with cot 20f, will respond because they are all sufficiently close to be within communication range of stretcher 20e (for purposes of discussion, it will be assumed that bed 20c is out of direct communication range with stretcher 20e). The response from beds 20a, 20b, and 20d and cot 20f includes information indicating the nodes that each of these apparatuses 20 are in communication with. Thus, for example, bed 20a might respond to stretcher 20e by indicating that it is able to communicate with bed 20b, bed 20c, cot 20f, and bed 20d. Similarly, bed 20d might respond to stretcher 20e by indicating that it is able to communicate with beds 20a, 20b, and 20c, as well as cot 20f. Still further, in addition to forwarding information about what nodes a particular node is currently able to communicate with, information identifying the relative signal strengths of each of the currently available nodes is also included. In this manner, routing of the information can be accomplished by selecting routes having relatively higher signal strengths, or at least signal strengths above a predetermined threshold, thereby ensuring that more bandwidth is available for transmitting information.

In some embodiments, the response back to stretcher 20e also includes information indicating whether any of the nodes 84 are able to communicate with a wireless access point 68 of healthcare network 70. Thus, for example, bed 20a might respond to stretcher 20e by indicating that not only is it able to communicate with beds 20b, 20c, and 20d, and cot 20f (and also their signal strengths), but also that bed 20b is able to communicate directly with a wireless access point 68, which, in the example of FIG. 3, is a WiFi access point, although it will be understood by those skilled in the art that other types of access points could be used. Because beds 20c and 20d, as well as cot 20f, are all in communication with bed 20b, they too might all respond to stretcher 20e with information indicating that bed 20b is in direction communication with access point 68. Each apparatus 20 is therefore able to include in its response to stretcher 20e an indication that it is or that it is not is direct communication with a wireless access point, as well as a similar indication for all of the apparatuses it is in communication with. Depending upon the size of the mesh network 86, additional levels of communication abilities may be provided for nodes 84 that are even further downstream from stretcher 20e.

In addition to responding to stretcher 20e's initial broadcast, each apparatus 20 that is within communication distance may also respond with additional information that may be useful for stretcher 20e. As was noted, such additional information may include information about the signal strength of each of the communication channels between apparatuses 20, and/or the signal strength between an apparatus 20 and an access point 68. Such additional information alternatively, or additionally, includes information indicating a current level of communication traffic and/or information backlog and/or available bandwidth and/or the congestion that a node is experiencing. Still further, such information includes information that uniquely identifies each node, and/or information that uniquely identifies each patient support apparatus 20.

All of the information that stretcher 20e receives in response to its initial broadcast message is stored in a memory accessible to first transceiver controller 58. This information enables controller 58 to determine which route, or portion of a route, is the best route for transmitting data to access point 68. That is, stretcher 20e uses the information it receives from the other nodes (e.g. 84a, 84b, 84d, and 840 to select an initial recipient of any data that it needs to forward to network 70 (which would be via access point 68 in FIG. 3, although there may be multiple access points in other examples). Once this initial recipient is chosen, node 84e of stretcher 20e transmits the desired information to that recipient, which then forwards the information onto access point 68, either directly or by some other route, depending upon circumstances. In some embodiments, the original source of the transmitted information (in this example, stretcher 20e) includes information indicating its preferred complete routing path to access point 68, while in other embodiments, the original source of the transmitted information only chooses the initial recipient of the transmitted data and leave subsequent routing decisions to the discretion of the recipient node and any other downstream nodes that relay the information to access point 68.

As was noted, the choice of the initial recipient of the information is made based upon any one or more of the items of information received from the other nodes. The choice of the initial recipient may also be combined with predefined data or programming instructions. Such predefined data or programming instructions may, for example, dictate that, absent extenuating circumstances, an apparatus 20 will try to communicate information to access point 68 in the most direct route (i.e. the route involving the fewest number of communications hops between the source of the data and network 70). Thus, as an example, stretcher 20e may be programmed to initially select by default bed 20b as the initial recipient of its transmitted data because bed 20b is in direct communication with access point 68. However, such programming could also take into account the signal strength of the communication path 88 between stretcher 20e and bed 20b and, if it is below a desired threshold level, cause node 84e to seek an alternate initial recipient with which it has a communication path 88 having a stronger signal. Stretcher 20e may therefore, as an example, determine that path 88 between stretcher 20e and bed 20b is too weak, and therefore choose to initially send its data to bed 20a. This choice of bed 20a as an alternative to the default initial recipient may be based upon any of the information stretcher 20e has received from the other nodes 84. Thus, the choice of bed 20a as the alternative initial recipient of the data from stretcher 20e may be made, for example, because the communication path 88 between stretcher 20e and bed 20a is stronger than any of the other communication paths stretcher 20e has with the other patient support apparatuses 20c, 20d, and 20f.

The data that is able to be transmitted from a patient support apparatus 20 includes a variety of different types of data, some of which will be discussed in greater detail below. In some embodiments, data about one or more sensors and/or systems on the patient support apparatus 20 is communicated. Such data includes information indicating whether the side rails of a patient support apparatus are up or down; whether the brake is locked or unlocked; the height of the frame 28 or patient support deck 30 above the base 22 (in those apparatuses where this height can be changed by a user); the angle of one or more sections of deck support 30 (such as head section 36—which may be useful to know for helping to prevent ventilator associated pneumonia and/or for other purposes); the output from a bed exit system that is incorporated into patient support apparatus 20 (such as, but not limited to, the bed exit system disclosed in commonly-assigned U.S. Pat. No. 5,276,432 issued to Travis and entitled PATIENT EXIT DETECTION MECHANISM FOR HOSPITAL BED, the complete disclosure of which is hereby incorporated herein by reference); information indicating whether a bed exit system is armed or disarmed; the output from a patient movement detection system that is incorporated into patient support apparatus 20 (such as, but not limited to, the patient movement detection system disclosed in commonly-assigned U.S. Pat. No. 6,822,571 issued to Conway and entitled PATIENT MOVEMENT DETECTION SYSTEM FOR A BED INCLUDING A LOAD CELL MOUNTING ASSEMBLY, the complete disclosure of which is also incorporated herein by reference); the output from a patent interface pressure detection system (such as, but not limited to, that disclosed in the PCT/US12/27402 application filed Mar. 2, 2012, discussed above); data from one or more medical devices that are either supported on apparatus 20, or in communication with apparatus 20 (such as via first transceiver 64); information from a video monitoring system (such as that disclosed in the Ser. No. 13/242,022 patent application mentioned above); and information from other devices or structures in the room that have wireless communication abilities (such as, but not limited to, the devices disclosed in the Ser. No. 13/570,934 application discussed above.

Any of the data that is transmitted from a patient support apparatus 20 is data that originates from that particular patient support apparatus, or it is data that is received from another patient support apparatus 20 that is to be relayed onto another node 84 or an access point 68. Regardless of whether the data that is to be transmitted originates from the support apparatus 20, or was received from another support apparatus 20, the algorithms used for determining the next recipient of the data are the same. Thus, for example, in the arbitrary example discussed above with respect to FIG. 3 wherein stretcher 20e is transmitting data that is to be forwarded to access point 68, the logic used by stretcher 20e to determine the initial recipient of its data is the same, regardless of whether the transmitted data originated from stretcher 20e, or it was received by stretcher 20e from another support apparatus (such as, for example, bed 20d). Similarly, once stretcher 20e transmits the data to an initial recipient (e.g. bed 20a), that recipient utilizes the same logic and/or algorithms that stretcher 20e used in deciding what node to forward the data to.

By forwarding information through mesh network 86 to access point 68, the information is able to avoid bottlenecks, route around weak communication channels, and in some cases (such as discussed below with respect to FIG. 4) avoid areas where communication with access point 68 is not possible. The routing algorithms used therefore ensure that data is efficiently, yet effectively, transferred to the healthcare network 70 so that the appropriate servers and/or applications on the network 70 can used the transmitted data in the desired manner.

Figure 4:
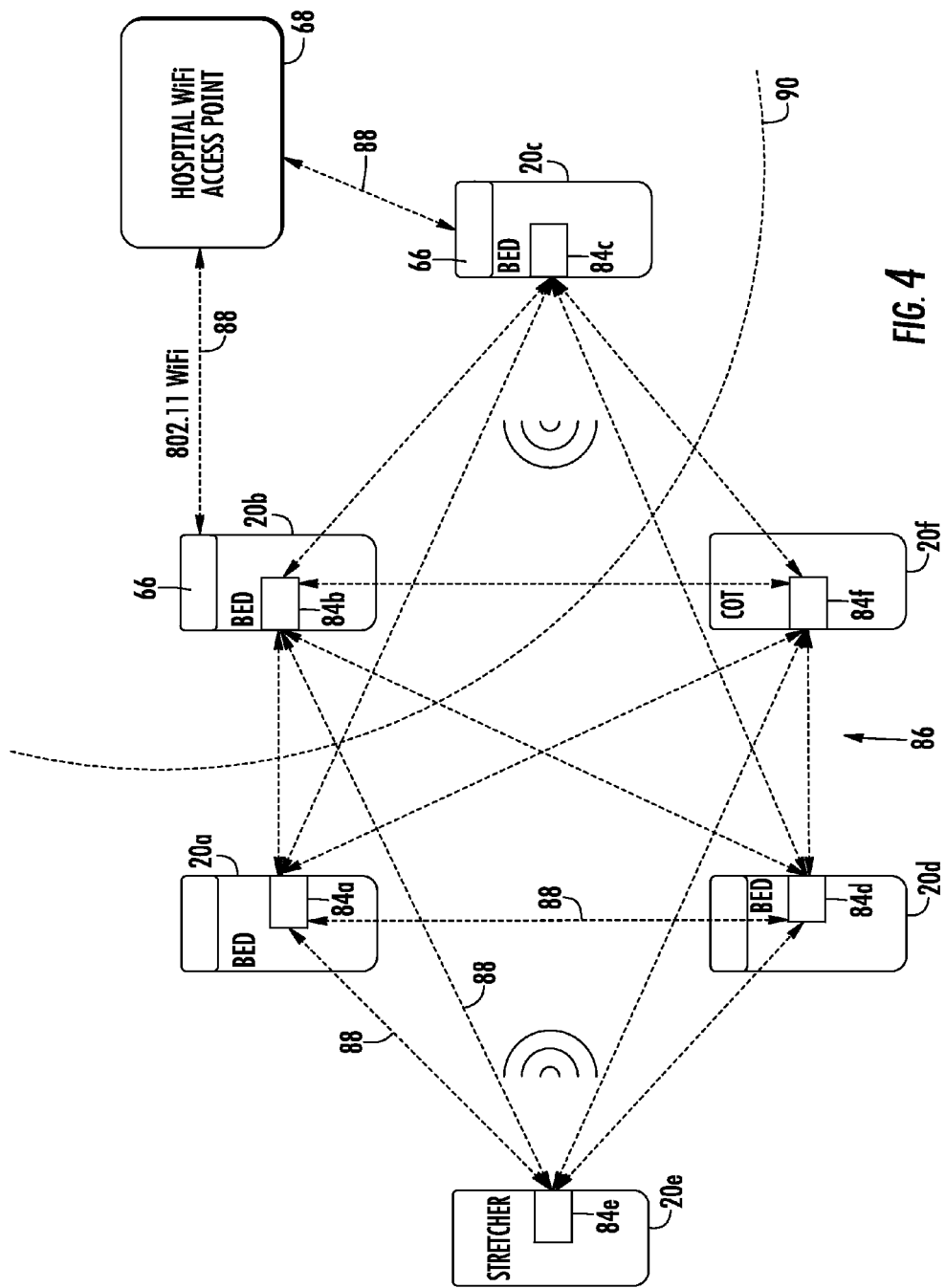
FIG. 4 is an plan view diagram similar to FIG. 3 showing how the mesh network may be used to forward information from patient support apparatuses outside a range of the access point to one or more other patient support apparatuses that are within range of the access point.

FIG. 4 illustrates another arbitrary example wherein some of the patient support apparatuses 20 and associated nodes 84 are completely outside the communication range of access point 68. In the example of FIG. 4, a boundary line 90 indicates the furthest extent of the communication range of access point 68. Thus, only beds 20b and 20c are within communication range of access point 68. Any information to be transmitted from beds 20a and 20d, or cot 20f and stretcher 20e to network 70 must therefore pass (in this example) through either bed 20b or bed 20c. By enabling patient support apparatuses 20 to communicate over, and form, a mesh network 86, the communication range of access point 68 is effectively extended. That is, because those apparatuses 20 within range of access point 68 (e.g. beds 20b and 20c) can talk to apparatuses outside of range 90 and relay information from these apparatuses 20 to access point 68, the effective communication range of access point 68 is enlarged. This allows healthcare facilities to avoid the expensive extra infrastructure that might otherwise be necessary to provide sufficient communication abilities throughout a facility (i.e. it may not be necessary to install as many wireless access points 68 in a given facility when the facility uses the mesh-network equipped patient support apparatuses 20 disclosed herein).

When a patient support apparatus 20 is forwarding data to network 70 via mesh network 86 and there are multiple patient support apparatuses 20 in direct communication with one or more access points 68 (such as, for example, the situation illustrated in FIG. 4), the choice of which apparatus 20 to forward data to may be made in the same manner as discussed above. That is, in the example of FIG. 4, the choice between routing data through bed 20b or 20c is based upon one or more of the following: a default preferred path, relative signal strengths, available bandwidth, traffic congestion, communication backlogs, and/or other factors. If such factors present an equal case for routing through beds 20b and 20c, then the ultimate choice may be based on a random selection, or some other factor.

In the examples of FIGS. 3 and 4, the data transmitted from a support apparatus 20 to access point 68 has been ultimately transmitted to access point 68 via a second transceiver 66 on one of patient support apparatuses 20. If that data has been received from another patient support apparatus 20 (and is thus being relayed to access point 68), the receipt of data is via first transceiver 64. Thus, mesh network communications is accomplished via first transceivers 64, while communications with one or more access points 68 is via second transceivers 66.

It will be understood by those skilled in the art that all of the first transceivers 64 do not have to be identical to each other. Similarly, it will be understood by those skilled in the art that all of the second transceivers 66 do not have to be identical to each other. If disparate types of first and/or second transceivers 64 and/or 66 are incorporated into the support apparatuses 20 of a given mesh network 86, then the communication abilities of the transceivers may also be relayed to each of the nodes and used in the algorithms for determining routing. For example, in some embodiments, some patient support apparatuses have a second transceiver 66 that is able to communicate in accordance with IEEE 802.11b standards, while other patient support apparatuses 20 are able to communicate in accordance with IEEE 802.11g or 802.11n standards, both of which are faster than 802.11b standards. This information is factored into the algorithms for choosing the most efficient routing of data to network 70.

Mesh network 86 is also useful for disseminating data from one or more sources on healthcare network 70. When disseminating such data, the same or similar algorithms can used for routing the data through mesh network 86 to the appropriate destination. Such disseminated data includes, but is not limited to, patient information (such as, but not limited to, information that identifies a particular patient who is occupying a particular patient support apparatus), caregiver information (such as, but not limited to, information identifying the what caregiver(s) have been assigned to a particular patient, room, or support apparatus 20), medical information (such as, but not limited to, information about the fall risk or a patient, information about the susceptibility of a patient to bed sores—such as a Braden scale rating, information and/or any other relevant medical information about a particular patient), commands (such as, but not limited to, commands to change the status of a system or component on patient support apparatus 20), requests for data, acknowledgements, and/or any other type of data that is desirably communicated to one or more patient support apparatuses 20, or to any of the devices or other structures that a patient support apparatus 20 is in communication with via one or more of its transceivers.

Each node 84 of mesh network 86 is configured to dynamically and regularly update its communication abilities and/or status so that the routing of data through mesh network 86 is dynamically adapted to changing conditions. Such changing conditions can include, for example, the movement of one or more patient support apparatuses 20 to different locations, traffic congestion, the addition or deletion of one or more data sources or destinations (e.g. one or more medical devices or support apparatuses 20), and/or any other conditions that might usefully influence the efficient routing of data through mesh network 86.

FIGS. 8A and 8B illustrate one example in which a mesh network 86 dynamically updates itself when a patient support apparatus 20 exits the mesh network 86. In the example of FIG. 8A, a bed 20u is communicating data to a bed 20v via two intermediate patient support apparatuses 20; namely, a bed 20w and a stretcher 20x. The information is being transmitted through nodes 84w and 84x of these two intermediate support apparatuses 20. This data path, however, may change, such as, for example, by the movement of one or both of support apparatuses 20w and/or 20x. In the example of FIG. 8B, stretcher 20x has been moved to a new location that is outside of mesh network 86. In order for patient support apparatuses 20u and 20v to continue to communicate, a new data path is automatically created by mesh network 86. In the example of FIG. 8B, the new data path is from bed 20v to bed 20w to bed 20y to bed 20v, and/or the reverse. By dynamically changing the routing of data when one or more nodes 84 are either added or removed from mesh network 86, communication can still be accomplished without interruption.

Figure 5:
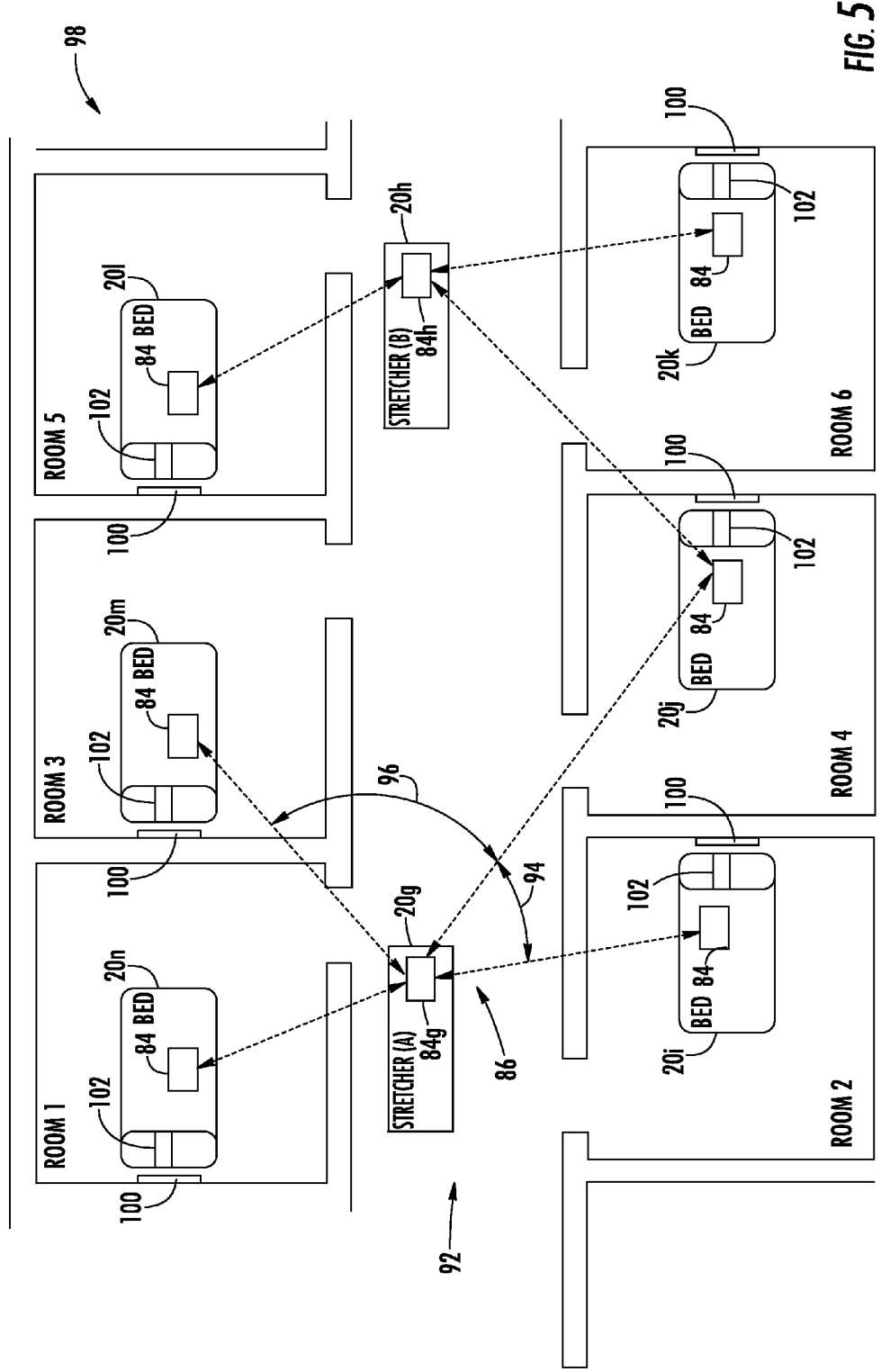
FIG. 5 is a plan view diagram of an arbitrary portion of floor plan of a healthcare facility that illustrates how some patient support apparatus embodiments may determine their location using triangulation techniques of signals received from other patient support apparatuses.

Alternatively, or in addition to, the data transfer abilities of mesh network 86 described above, some embodiments of patient support apparatuses 20 are configured to use mesh network 86 to determine their location within a healthcare facility. This is especially useful for healthcare facilities where some apparatuses 20 are not able to determine their location at all times, such as, for example, during movement of the apparatus 20 from one location within the facility to another location within the facility. FIG. 5 illustrates one manner in which mesh network 86 is used to determine the location of one or more patient support apparatuses. Specifically, stretchers 20g and 20h are shown in a corridor or hallway 92 within an arbitrary portion of a healthcare facility 98. Stretcher 20g includes a mesh network node 84g while stretcher 20h includes a mesh network node 84h. These nodes 84g and 84h are able to wirelessly communicate with other nodes 84 that are within a vicinity of these nodes (the size of the vicinity will depend upon the specific communication protocol and/or standards used by nodes 84, as well as the communication and reception power of the electronics in nodes 84). Nodes 84g and 84h (as well as, in some cases, the nodes 84 on beds 20i, 20j, 20k, 20l, 20m, and 20n) are adapted to determine their location by using triangulation techniques, or trilateration techniques, or some combination of the two, with the other nodes 84 that are within communication range. Such triangulation techniques will enable the nodes to calculate their relative position to the other nodes that are within communication range. If one or more of the other nodes that are within communication range knows its absolute location within health care facility 98, or otherwise possesses information that enables its absolute location to be determined within facility 98, then those other nodes that know their relative location to these nodes are able to calculate their absolute position within the facility.

If configured to determine location based upon triangulation, each node 84g and 84h includes one or more antennas that are adapted to determine the direction in which signals from the other nodes 84 are received at nodes 84g and 84h, respectively. Such antennas and/or other equipment may be conventional equipment, as would be known to one of ordinary skill in the art. If a node (e.g. 84g and/or 84h) receives signals from a sufficient number of other nodes, the angular information determined from those signals will be sufficient for the node (84g or 84h) to determine its relative location to the patient support apparatuses 20 from which it received signals. This relative position can be converted into an absolute position within the healthcare facility if the absolute positions of the patient support apparatuses that transmit signals to nodes 84g and/or 84h are known. In some embodiments, this conversion of relative position to absolute position is performed by one or more processors located on the patient support 20 itself, while in other embodiments, it is performed by a server or application that is running on healthcare network 70.

FIG. 5 illustrates an example of how, in one embodiment, stretcher 20g determines its location using triangulation techniques. By determining the direction from which signals are received from nodes 84 on patient support apparatuses 20i and 20j, which are in rooms 2 and 4, respectively, node 84g will be able to determine a first angle 94 (FIG. 5). By determining the direction from which signals are received from the nodes 84 on patient support apparatuses 20j and 20m, which are in rooms 4 and 3, respectively, node 84g will also be able to determine a second angle 96 (FIG. 5). Further, because the locations of beds 20i, 20j, and 20m is already known—as determined in any conventional manner, at least one of which is described in greater detail below—node 84g on patient support apparatus 20g is able to determine its absolute location within healthcare facility 98. The relative signal strength of all of the received signals may also be used in determining location.

It will be further understood by those skilled in the art that the determination of the location of a patient support apparatus 20 (such as stretcher 20g in FIG. 5) within a given facility 98 may be, in some embodiments, a determination of an approximate location. For example, the algorithms used to determine location may, in some embodiments, specify the location of the patient support apparatus merely to the level of a room or a portion of a room, or a corridor or hallway, or a section of a corridor or hallway, or some other generalized area. However, it will also be understood that finer levels of position granularity are determined in some embodiments.

If nodes 84 are equipped to determine location using trilateration or multilateration techniques, either in lieu of, or in addition to triangulation techniques, nodes 84 may be configured to determine the time it takes for signals from other nodes 84 to travel to the node whose destination is being determined. Such time of flight measurements or computations can be used to determine distances between nodes 84. This will enable a node 84 to determine its relative location. Further, if some of the absolute positions of the nodes are known, the relative position may be converted into an absolute position within the healthcare facility 98.

In one embodiment, some of the patient support apparatuses 20 are able to determine their location within a healthcare facility 98 by way of a location system that utilizes a plurality of stationary modules 100 and stationary module transceivers 102. The stationary modules 100 are positioned on walls, ceilings, or in other fixed locations whose absolute positions within the healthcare facility 98 are known. The module transceivers 102 are incorporated into some or all of the patient support apparatuses 20. In the example of FIG. 2, the electrical control system 44 of patient support apparatus 20 has transceivers 102 feeding into, and controlled by, actuator/sensor controller 50. It will be understood by those skilled in the art that transceivers 102 may be controlled by other controllers, and/or integrated into a patient support apparatus in different manners. Further, as will be discussed in greater detail, stationary modules 100 and stationary module transceivers 102 are configured the same as locators 252 and receivers 254, respectively, in at least some embodiments, or the same as locators 444 and transceivers 440, respectively, in still other embodiments.

In one embodiment, a healthcare facility may have a plurality of patient support apparatuses 20 that are beds that include such transceivers 102, while other types of patient support apparatuses 20—such as stretchers, cots, and the like—might not include such module transceivers 102. Regardless of which specific patient support apparatuses 20 have module transceivers 102 incorporated therein, any such apparatus 20 having a module transceiver 102 incorporated therein will be able to communicate with a fixed module 100 when the apparatus is within a relatively close proximity thereto. Such proximity may be on the order of five to ten feet, or it may be other distances. In some embodiments, module transceiver 102 communicates with modules 100 via infrared signals, although it will be understood by those skilled in the art that other types of signals may be used for communication between modules 100 and transceiver 102.

In general, because the locations of modules 100 is known, and because the patient support apparatuses can only communicate with a given module 100 (via transceivers 102) then they are within a close proximity to the given module 100, the very establishment of such communication indicates that the patient support apparatus 20 is in close proximity to a given module 100 whose location is known. This allows the location of a patient support apparatus 20 to be determined.

In one embodiment, modules 100 are configured to respond to interrogations received from transceiver 102 with an identifier that uniquely identifies and distinguishes that particular module 100 from all other such modules 100 within the healthcare facility 98. The patient support apparatus 20 includes a map, table, or other information that correlates that specific module 100 to a known location, or it communicates with an application or server on network 70 that maintains such a map, table, or other information. In either case, the patient support apparatus is able to determine its location. Further details of the operation of modules 100 and transceivers 102, as well as the manner in which they can be used to determine location, are found in commonly assigned, copending U.S. patent application Ser. No. 12/573,545 filed Oct. 5, 2009 by applicants David Becker et al. and entitled LOCATION DETECTION SYSTEM FOR A PATIENT HANDLING DEVICE, the complete disclosure of which is also incorporated by reference herein.

If a location system such as the one just described (i.e. having modules 100 and transceivers 102) is used within a healthcare facility, it is customary to only position such modules 100 near locations where beds are likely to be stationed or parked (i.e. at the location in a room where the bed normally resides, or, if in a multi-bed room, at each location where the bed is normally parked). Such modules 100 are not typically placed in hallways or other locations where the beds or other patient support apparatuses are temporarily moved. The aforementioned triangulation and/or trilateration techniques used with nodes 84 may therefore be used to determine location when a patient support apparatus 20 is not within an operational vicinity of a module 100. Further, the aforementioned triangulation and/or trilateration techniques may be used with those patient support apparatuses 20 that might not be equipped with a location transceiver 102. Nodes 84 therefore complement existing location determining systems and/or fill in gaps in those existing location determining systems so that greater location knowledge—in terms of both coverage throughout the facility and/or in terms of the number of patient support apparatus—is achievable within a healthcare facility. The location information determined by way of nodes 84 is stored locally on the respective patient support apparatus 20 and/or it is forwarded to healthcare network 70 to one or more servers and/or applications running on the network 70. The forwarding of such information takes place using one or more mesh networks 86 in the manners described above, or it takes place via a direct communication with an access point 68 of network 70, or by other means.

In some embodiments, patient support apparatuses 20 that are not equipped with location transceivers 102 are, after determining their own locations, used to help determine the location or locations of other patients, or other patient support apparatuses 20 that are also not equipped with location transceivers 102, or that are equipped with such transceivers 102 but are currently located outside the vicinity of a module 100. For example, if stretcher 20g in FIG. 5 determines its location using its node 84g and one of the triangulation and/or trilateration techniques discussed above, node 84g is configured to respond to signals from node 84h of stretcher 20h that are being sent by node 84h to determine the location of stretcher 20h. In other words, node 84h of stretcher 20h is thereafter able to measure its angular relationship and/or its distance to stretcher 20g when determining its location. Thus, once a patient support apparatus 20 uses its node 84 to determine its location, it serves as a source of location information for other patient support apparatuses 20. In this way, it is possible to extend location determination abilities farther and farther away from modules 100. Or, stated alternatively, the node triangulation/trilateration position determining system described herein augments any existing location system, and may be cascaded upon itself so that patient support apparatuses that can only communicate via nodes 84 with other patient support apparatus 20 that themselves are outside the range of modules 100 can still determine their location.

The node triangulation/trilateration position determining system described herein may also be used with a position determining system that is based upon WIFI signals and the known location of the corresponding routers, access points, and/or other stationary structures that communicate those WIFI to and from the mobile patient support apparatuses 20. For example, if a patient support apparatus 20 is communicating with a specific access point 68 via second transceiver 66, that patient support apparatus 20 may be configured to determine its general location as being within a general range of the access point 68. This general range is then further refined by way of the triangulation/trilateration techniques described above. Further, this triangulation/trilateration technique is able to be used to extend the range at which patient support apparatus 20 is capable of determine its location beyond the communication range of the access point 68. Indeed, the range may be extended—depending upon the location of patient support apparatuses 20—to locations where there are no available access points 68.

The patient support apparatus to patient support apparatus communication that has so far been described can be used for two separate and potentially independent purposes. First, as was described previously, this communication may be used to create mesh networks for better routing of information between patient support apparatuses 20 and a healthcare network 70. Second, as was also just described above, this patient support apparatus to patient support apparatus communication may be used to determine location and/or to augment or complement the location determining abilities of another patient support apparatus location determining system. As will be described below with reference to FIG. 6, this patient support apparatus to patient support apparatus communication may be used for yet another purpose: transferring patient information between patient support apparatuses.

In lieu of, or in addition to, either of the mesh networking and position determining functions of nodes 84, such nodes are also useful for storing and transferring patient information, medical information, or other information between patient support apparatuses 20. That is, nodes 84 are configured to store information about the patient that is currently being support on the support apparatus 20. This information is received via transceivers 64, or by any of the other transceivers positioned on support apparatus 20. Further, the storage of this information may be in a memory within node 84, or it may be in another location on the patient support apparatus 20. Regardless of the source of the information and regardless of its storage location on the patient support apparatus, the information includes personal information and/or medical information about the patient being supported on apparatus 20. For example, the information may include the patient's name, height, weight, allergies, fall risk assessment, bed sore risk assessment, and/or any other medical or personal information that may be usefully stored on the support apparatus.

In some patient support apparatus embodiments, the stored information is displayable on an LCD screen, touchscreen, or other type of display on the patient support apparatus so that caregivers will have visual access to the information. The patient support apparatus 20 may also be configured to transmit the information locally to a pendant supported on patient support apparatus 20, or to a medical device that is plugged into, or otherwise communicatively coupled, to patient support apparatus 20. In such cases, the pendant and/or medical device are configured to display the information. In still other embodiments, the patient support apparatus wirelessly transmits the information to a portable computer device, such as a laptop, smart cell phone, personal digital assistant, or other device so that the information may be displayed thereon.

Regardless of the manner in which the patient information is displayed, or is displayable, patient support apparatus 20 is configured to transfer the patient information to another patient support apparatus 20 when the corresponding patient is transferred. In this way, the patient information follows the patient around as he or she is moved from one patient support apparatus 20 to another within healthcare facility 98. In the embodiment shown in FIG. 2, node 84 with first transceiver 64 and first transceiver controller 58 are used to control this transfer of patient information between support apparatuses 20, although it will be understood that any other transceivers could be used that enable inter-support apparatus communication.

Figure 6:
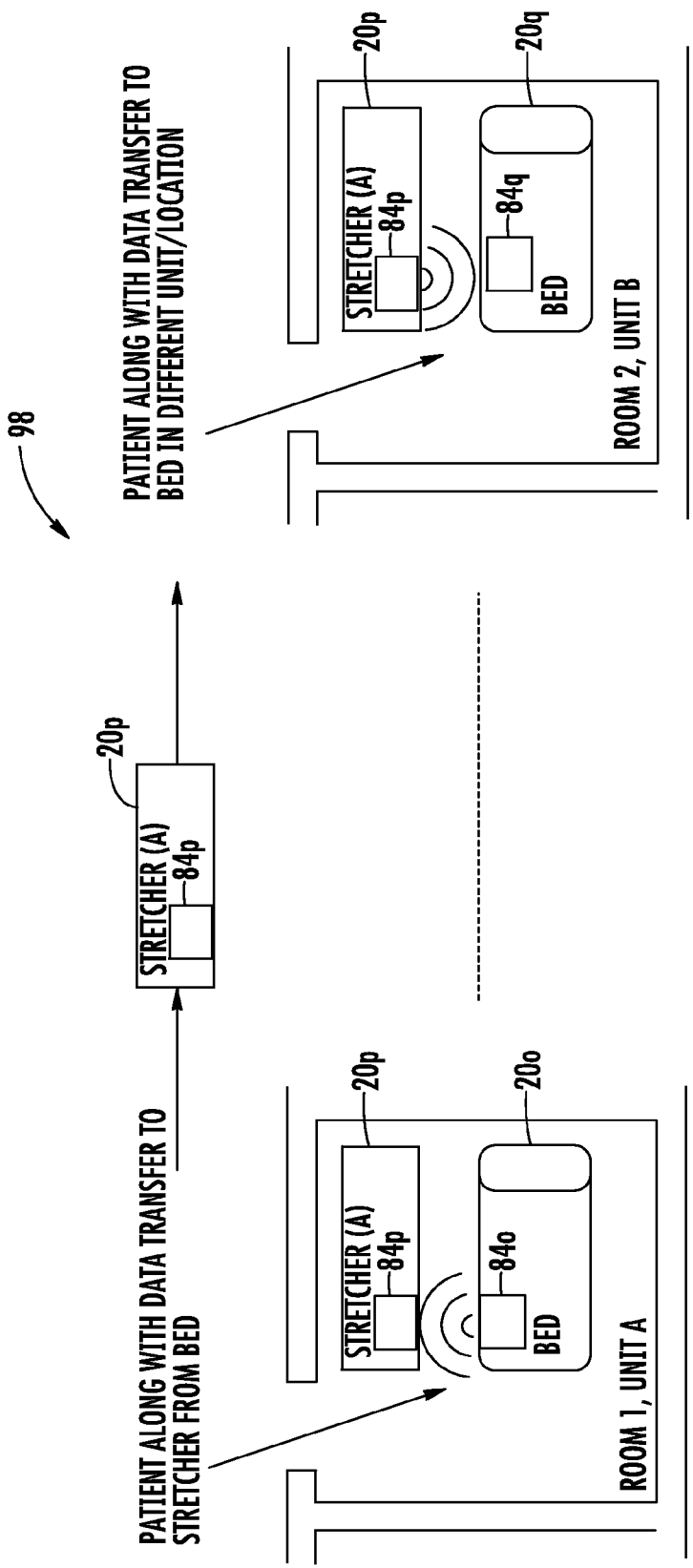
FIG. 6 is a plan view diagram of another arbitrary portion of a floor plan of a healthcare facility that illustrates how some patient support apparatus embodiments may transfer patient information from one patient support apparatus to another as a patient is transferred from one patient support apparatus to another.

In the example of FIG. 6, a bed 20o is shown transferring patient data to a stretcher 20p. More specifically, node 84o of bed 20o is wirelessly communicating patient information to node 84p of stretcher 20p. This information transfer includes any of the information mentioned above, or any other desirably transferred information. Such information will typically be transferred when a patient (not shown) who was previously supported on bed 20o is transferred to stretcher 20p. Once the patient and his or her corresponding patient information have been transferred to stretcher 20p, stretcher 20p may be transported to another location, such as, for example, a room labeled "Room 2, Unit B" in FIG. 6. At the second location, the patient may, in some cases, be transferred to yet another patient support apparatus 20. In the example of FIG. 6, the patient may be transferred off of stretcher 20p and onto a different bed 20q. When this patient transfer occurs, the stretcher 20p will also transfer the corresponding patient data to bed 20q as well. In this manner, bed 20q will be in possession of the information that corresponds to the patient that has just been transferred thereto. Such apparatus-to-apparatus 20 transfers enable patient information to be portable and to easily accompany a patient as he or she is moved throughout a healthcare facility.

In some embodiments, the transfer of patient information from a first patient support apparatus 20 to a nearby second patient support apparatus 20 is commenced in response to an authorized individual, such as a caregiver, physically activating a data transfer mechanism on one or both of the patient support apparatuses. The mechanism is implemented as a touchscreen in one embodiment, although it will be understood that it may alternatively include one or more buttons, additional touchscreens, one or more switches, levers, or other physical components. Such mechanisms may be part of any of any of the user controls on patient support apparatus, or it may be positioned elsewhere. In the example of FIG. 2, patient support apparatus 20 includes a first set of user controls 104a located on a first siderail, a second set of user controls 104b located on a second siderail, and a third set of user controls 104c located on a footboard of patient support apparatus 20. The mechanism for transferring data between support apparatuses 20 is positioned the third set of user controls 104c, although it could be positioned on any one or more of these user controls 104.

In some embodiments, the transfer of patient data is automatically commenced when patient support apparatus 20 senses that a patient has exited and when another patient support apparatus 20 is detected to be within close communication distance (such as via a measurement of signal strength between nodes 84). The detection of a patient exiting a support apparatus 20 may be implemented by a conventional bed exit detection system 106, such as, but not limited to, one of the type illustrated in FIG. 2, which includes a plurality of load cells 108 that feed force data into a scale system controller 52. The force data measurements represent the forces exerted by the patient onto the patient support deck 30, and their absence and/or diminishment beyond a threshold indicate that the patient is off of deck 30.

A patient support apparatus 20 may also be configured to receive patient information from another support apparatus 20, or from another source, upon the manipulation of one or more user controls 104, or it may take place automatically. When configured to take place automatically, the node 84 of the receiving support apparatus 20 monitors its bed exit detection system, or scale system, to determine if there have been any recent increases in weight (signifying the addition of a patient to a previously unoccupied patient support deck 30). If there have, and if node 84 of the receiving support apparatus is detecting a nearby node 84 that is transferring patient data, the node 84 of the receiving support apparatus 20 stores the incoming patient data and accepts it as corresponding to the recently added patient. If the receiving patient support apparatus has patient data stored therein from a prior patient, this may be automatically overwritten by the new data, or the old data may be stored therein for future user or future retrieval.

A verification process is incorporated into the patient data transfer such that a caregiver may easily determine whether the patient data has been transferred correctly. In some embodiments, a graphic or textual display on the receiving support apparatus 20 will display the received name of the patient and prompt the caregiver to confirm that this corresponds to the patient now positioned thereon. If it does not, then the support apparatus 20 discards or ignores the new patient data, or otherwise concludes that it does not correspond to the patient currently occupying that patient support apparatus. Once the data has been verified by the caregiver as having been properly transferred, the receiving support apparatus 20 sends a signal back to the transmitting apparatus indicating it is OK to purge, overwrite, or no longer save, the patient data that it just transferred. In this way, the now empty patient support apparatus will have its memory effectively empty so that it is able to receive patient data corresponding to the next patient. In some embodiments, a patient support apparatus 20 may retain the patient data after transferring it to another support apparatus so that it may be retrieved for potential further use.

In addition to patient data, the transferred data may also include information about the usage of patient support apparatus, such as the amount of time the patient support apparatus was used by a particular patient, and/or any other information that may be useful for billing purposes. Still further, as will be described in greater detail below, the transferred information may include information gathered by one or more medical devices that were used or associated with the patient, including not only medical information that may be useful for treating or caring for the patient, but also usage information that may be useful for billing purposes.

The automatic transfer of information to an adjacent patient support apparatus may also be configured to be implemented based upon an radio frequency (RF) tag, bracelet, or other structure worn by a patient that may be detected automatically by one or more sensors positioned on each of the patient support apparatuses. When a support apparatus 20 detects a new patient has entered it via such a tag, bracelet, or other device, it requests via one or more node 84 transmissions that the adjacent patient support apparatus transfer the corresponding patient information, or other information, to it.

FIG. 7 illustrates yet another use for nodes 84 in one or more patient support apparatuses. Specifically, FIG. 7 illustrates how nodes 84 are useful for communicating medical information received from one or more medical devices 110. The use of nodes 84 in patient support apparatuses 20 to communicate medical information may be the sole use of nodes 84 in a given patient support apparatus, or it may be combined with any of the aforementioned use of nodes 84 in patient support apparatuses 20 (e.g. mesh network communication, location determination, and patient information storage and transfer).

In the arbitrary example illustrated in FIG. 7, a patient 112 is shown positioned on a bed 20r having associated therewith two medical devices 110a and 110b. Medical devices 110a and 110b are configured to communicate with node 84r of bed 20r. Medical devices 110a and 110b therefore are able to transfer data gathered by the medical devices 110a and 110b to bed 20r, which either uses some or all of the transferred information itself, or it forwards it on for communication to healthcare network 70. Patient support apparatus 20s similarly has two medical devices 110 associated with it—devices 110c and 110d—which communicate information to node 84s on bed 20s. A third bed 20t is shown with no medical devices associated with it, yet it may still be in communication via its associated node 84t with node 84r and/or node 84s.

As was alluded to above, each patient support apparatus 20 in some embodiments includes a sensor for automatically detecting a patient ID device 114 that is worn, or otherwise carried with, each patient. The patient ID device 114 carries sufficient information for one or more sensors on patient support apparatus 20 to automatically determine the identity of a patient positioned thereon. With this patient information, support apparatus 20 is able to associate the data received from the one or more medical devices 110 that are communicating data to support apparatus 20 so that the medical data is correlated to a specific patient. The patient support apparatus 20 then forwards this medical data, with the corresponding patient identification, to network 70, which includes one or more applications or servers that utilize this data. Such servers or applications may include an electronic medical records system, or other system.

When forwarding this data to network 70, the nodes 84 of the respective support apparatuses 20 may forward the information thereto by first transmitting the information to one or more intermediate patient support apparatuses before the data ultimately arrives at network 70. This may involve routing the data through a mesh network, as described previously, or it may be forwarded in other manners. As shown in FIG. 7, beds 20s and 20t both forward data to access point 68, and receive data from access point 68, by routing the data through bed 20r. Bed 20r, on the other hand, may communicate directly with access point 68 via second transceiver 66.

Figure 9:
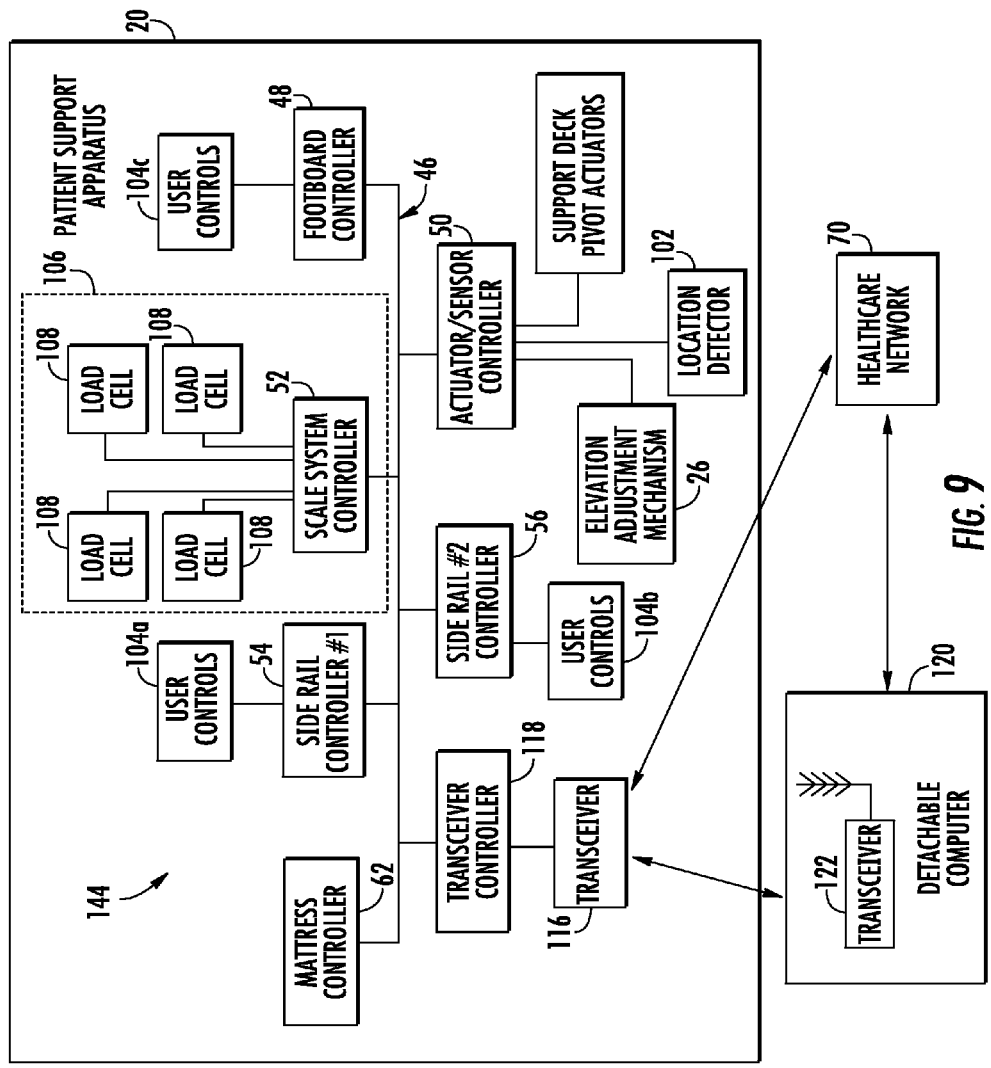
FIG. 9 is a diagram of an alternative electrical control system that may be used with any of the patient support apparatuses described herein.

FIG. 9 illustrates an alternative electrical control system 144 that may be used on any one or more of the patient support apparatuses 20 described herein. Electrical control system 144 includes multiple components that are common to electrical control system 44 described above (FIG. 2). Those components in common are labeled with the same reference numbers, and operate in the same manners described above. Further description of those components is therefore not provided.

Electrical control system 144 differs from the previously described control system 44 in that first and second transceivers 64 and 66, respectively, have been eliminated. A local transceiver 116 has also been added, along with a local transceiver controller 118. Local transceiver 116 is adapted to communicate with a detachable computer 120 that is physically supportable on patient support apparatus 20. More specifically, local transceiver 116 communicates via Bluetooth, ZigBee, or any other suitable wireless protocol with a computer transceiver 122 incorporated into detachable computer 120. Detachable computer 120 is a conventional a laptop, a tablet computer (such as, but not limited to, an iPad), or any other portable computer that may be removably coupled to patient support apparatus 20. The removable coupling of the computer 120 to patient support apparatus 20 may involve only a physical coupling in which the computer is physically supported and/or secured to patient support apparatus 20, but communication takes place wirelessly. Alternatively, the coupling may involve one or more wires, such as communication wires, that are connected between the computer 120 and patient support apparatus 20. In either case, the computer 120 is able to communicate with transceiver 116 such that information may be sent from computer 120 to patient support apparatus 20, and/or information may be received from patient support apparatus 20 by computer 120. Such information includes any of the information discussed above in any of the embodiments described herein such as, but not including, patient information, medical information, bed status information, relayed information received from other support apparatuses 20, information to be relayed to other patient support apparatuses 20, location information, etc.

The coupling of computer 120 to patient support apparatus, in some embodiments, enables the computer 120 to function as a user interface in which any or all functions of the patient support apparatus 20 are able to be controlled by computer 120. In one embodiment, when computer 120 is coupled to patient support apparatus 20, a touch screen on computer 120 appears that includes icons and/or graphics that mimic a control panel already on patient support apparatus 20, or that mimics a control panel that is of the type that might be on patient support apparatus 20, thereby giving the caregiver the means for controlling patient support apparatus 20 through computer 120. One example of a removable computer that may be coupled to a patient support apparatus 20 is described in greater detail in commonly assigned, copending U.S. provisional patent application Ser. No. 13/783,699, filed Mar. 4, 2013 by applicants Cory Herbst et al. and entitled PATIENT SUPPORT, the complete disclosure of which is hereby incorporated herein by reference. Any or all of the other features described in this application may also be incorporated into any of the patient support apparatuses 20 described herein.

FIG. 10 illustrates an arbitrary portion of a healthcare facility 98 in which multiple patient support apparatuses 20 are shown incorporating multiple of the concepts described herein. These include the use of nodes 84 for determining location, for creating a mesh network, for transferring patient information, and for relaying medical device information. For example, patient support apparatus 20*c* receives information from medical devices D1 and D2, which it then relays onto patient support apparatus 20*a* via direct communication between nodes 84*c* and 84*a*. When patient support apparatus 20*a* receives this information, it passes it onto network 70 via transceiver 66. Alternatively, if the connection between patient support apparatus 20*a* and network 70 is not operable, or otherwise not suitable, patient support apparatus 20*a* is able to relay this information to another support apparatus 20 that then forwards this information to network 70.

Also shown in FIG. 10 is the transfer of patient information from support apparatus 20*a* to support apparatus 20*z*, which then moves down one or more hallways to a different room, where it then transfers to the patient information to support apparatus 20*b*. This patient information is transferred via nodes 84 in any of the manners described above. While stretcher 20*z* is in transit, it may determine its location using nodes 84 by any of the triangulation, trilateration, or mutlilateration methods described herein, or in other manners. Any information on any of the servers or applications on network 70 may also be transmitted to the desired patient support apparatus in a reverse manner.

It will be understood by those skilled in the art that the use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Figure 11:
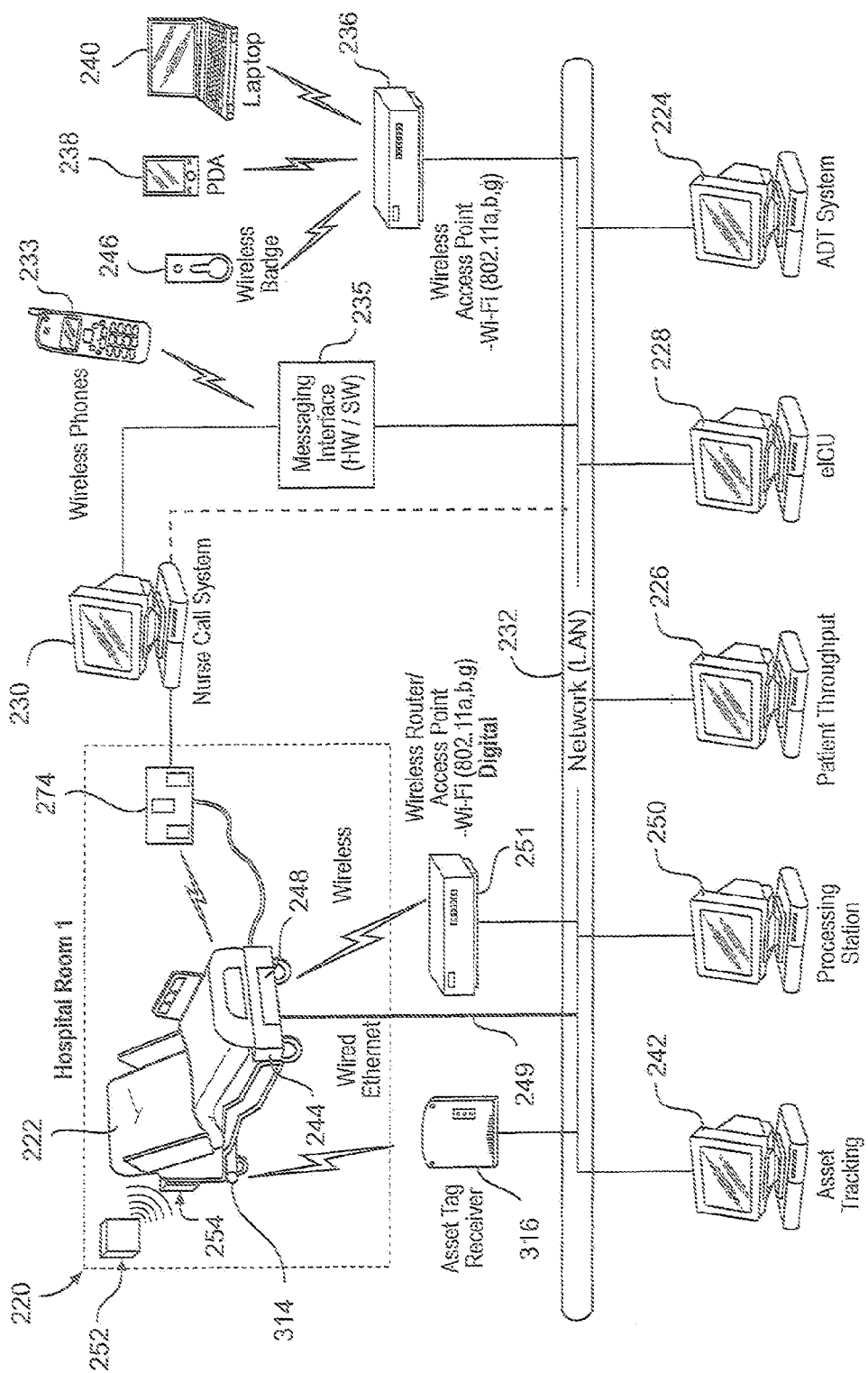
FIG. 11 is a schematic view of a healthcare facility with a network.

A location detection system for a facility is generally shown at 220 in FIG. 11. The location detection system 220 is described as being integrated into a patient handling device 222 of a healthcare facility such as a hospital. Patient handling devices 222 include devices such as beds, stretchers, cots, wheelchairs, and the like. It should be appreciated that the concepts provided by the present invention could also be applied to other devices located in a healthcare facility including, but not limited to infusion pumps, patient monitoring devices, patient therapy devices such as stand-alone therapy mattresses, and the like. It should also be appreciated that these principles could be applied to non-healthcare facilities. For purposes of description, reference is generally made to healthcare facilities.

Referring to FIG. 11, the healthcare facility includes several systems that can be placed in electronic communication with one another through a common network 232. These systems include admission-discharge-transfer (ADT) systems 224 and patient throughput systems 226 such as those offered by Premise Development Corporation. These systems may also include eICU systems 228 such as those provided by Cerner Corporation for the remote monitoring of critically ill patients. A nurse call system 230 may also be in communication with the network 232. For instance, a nurse call system provided by Rauland-Borg Corporation can be used to instantly transfer nurse calls from a patient to the network 232, or to the patient's primary and/or secondary caregivers via a wireless phone 233 using well-known messaging interfaces 235. This places the patient in immediate contact with a healthcare professional to provide faster, more efficient service.

Several communication devices may also be used to access the data or information provided by these systems 224, 226, 228, 230 to receive messages or alerts from these systems 224, 226, 228, 230, or to transmit information to these systems 224, 226, 228, 230. For instance, a wireless badge 246 may be in communication with these systems 224, 226, 228, 230 via wireless access points 236 provided throughout the healthcare facility. Healthcare professionals, e.g., nurses, nurse's aides, medical assistants, nurse practitioners, physician assistants, physicians, etc., may carry the wireless badges 246 to alert the nurse when a patient has called for assistance, or that an alarm condition is present. The nurse could also use the wireless badge 246 to speak to a voice recognition system to report an alarm condition, or to report that the nurse has completed a task, to report any event that may occur in the healthcare facility. Personal digital assistants (PDAs) 238 could also be in communication with the networked systems 224, 226, 228, 230 to transfer data and information between the PDAs 238 and the network 232. Similarly, laptop computers 240 could be used to transfer data and information.

Asset tracking systems 242 may also be integrated into the network 232. Such systems 242 may include those offered by Radianse, Inc., Versus Technology, Inc. or others to track assets throughout the healthcare facility. In some embodiments, the location detection system 2220 is intended to operate independently of the asset tracking system 242 to specifically identify the location, e.g., room and zone, of the patient handling devices 222. In other embodiments, the location detection system 2220 of the present invention is intended to work in conjunction with the asset tracking system 242 to identify the location of the patient handling devices 222 in the healthcare facility.

Still referring to FIG. 11, in one embodiment of the present invention, the patient handling device 222 is adapted for communicating with the network 232. More specifically, a central processing unit 244 (CPU) of the patient handling device 222 is in electronic communication with the network 232 via a communication module 248. The CPU 244 carries out the functions of the patient handling device 222 such as motor functions for raising or lowering movable sections of the patient handling device 222 in response to user input, sensing functions for sensing siderail positions, bed height, patient position or bed exit, patient weight, brake positions, and the like, as will be appreciated by those skilled in the art, or therapy functions for a therapy mattress, such as rotation, percussion, or vibration functions. The CPU 244 includes the necessary processors and memory for carrying out these functions as will be appreciated by those skilled in the art.

The CPU 244 and communication module 248 are physically supported by the patient handling device 222 to move with the patient handling device 222 from location to location. Preferably, one or more housings enclose the CPU 244 and the communication module 248 with the housing or housings being mounted to a frame of the patient handling device 222. As a result, all of the hardware necessary for connecting the CPU 244 of the patient handling device 222 to the communication module 248 is located on and supported by the patient handling device 222. It should be appreciated that the CPU 244 and the communication module 248 could be integrated into a single chassis or could be separate connectable components linked together in a wired or wireless configuration. By providing the communication module 248 on the patient handling device 222, the patient handling device 222 acts as a communication center or link for transmitting data and/or information related to the patient handling device 222, including its location, to the network 232.

The communication module 248 may be connected to the network 232 via a wired and/or wireless connection to transfer data and/or information back and forth between the CPU 244 and the hospital network 232. In a wired configuration, the communication module 248 may be a transceiver wired through a communication link 49 to the hospital network 232. The communication link may be an RS-232 cable, and Ethernet-compliant cable, or any other wired connection known to those skilled in the art. In a wireless configuration, the communication module 248 may be a wireless transceiver or router that is configured with a compatible wireless transceiver or router 251 located on the hospital network 232. In some embodiments, both wired and wireless configurations are present on the patient handling device 222 to easily accommodate user preferences. It should be appreciated that in some patient handling devices 222, there is no CPU 244, but instead a plurality of electronic modules that communicate on a peer-to-peer network. In this instance, the communication module 248 is simply one of the modules or nodes in the peer-to-peer network. However, for purposes of description, reference is made to a master/slave system utilizing the CPU 244 of the patient handling device 222.

A processing station 250 is in communication with the network 232 to process data and/or information received from the various systems 224, 226, 228, 230, 242 or the patient handling device 222 via the communication module 248 to configure or control the various systems 224, 226, 228, 230, 242 or the patient handling device 222. In one embodiment, the processing station 250 is positioned at a central nurse's station in the healthcare facility and is implemented in a workstation, e.g., a personal computer, for use at the central nurse station. The workstation may include software configured to manipulate data and/or information received from the various systems 224, 226, 228, 230, 242 or the patient handling device 222. For instance, the workstation may be configured to receive data and/or information from the communication module 248 of the patient handling device 222 or to transfer data and/or information back to the patient handling device 222. Such data may originate from a bed exit detection system, a bed height detection system, a weight scale, a siderail sensing system that detects a position of the siderails, a therapy mattress, and the like. The processing station 250 preferably includes a graphical user interface on a touch-screen display for reviewing and manipulating the data and/or information. It should be appreciated that the processing station 250 may also be a stand-alone unit that is not located on the network 232, but includes the necessary hardware to link to the communication module 248 of the patient handling device 222.

Figure 12:
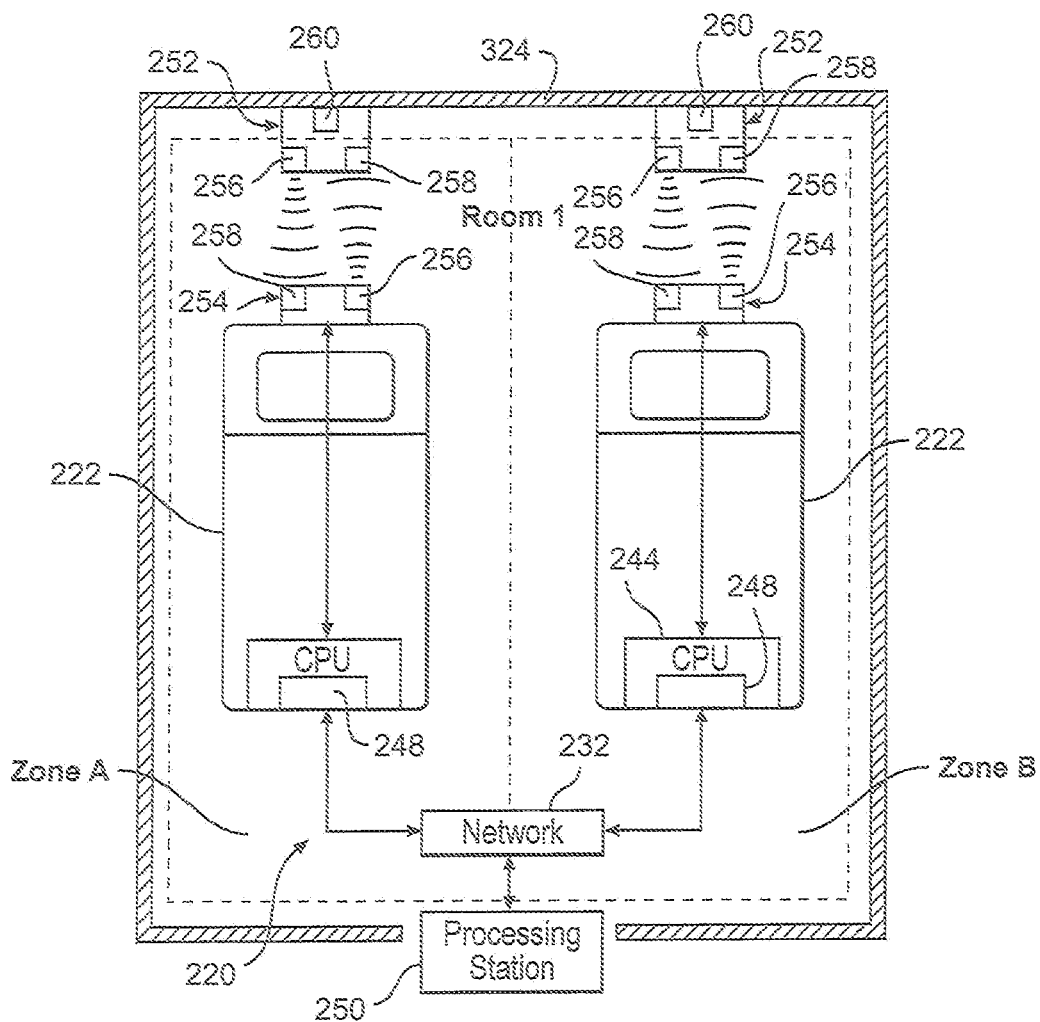
FIG. 12 is a top view of a typical room floor plan in the healthcare facility with two zones labeled A and B, schematically illustrating a location detection system embodiment utilizing a locator configured for transmitting a unique location identifier to a receiver located on a patient handling device.

Referring to FIG. 12, a typical room floor plan in a healthcare facility is illustrated. As shown, the room, labeled Room 1, includes two zones, labeled Zone A and Zone B. These zones A, B are also often referred to as bed bays or bed areas. The location detection system 220 of the present invention is configured to determine the particular zone in which the patient handling device 222 is located. In the embodiment of FIG. 12, two patient handling devices 222 are illustrated for positioning at a location, e.g., Zone A and Zone B, in the healthcare facility. The location detection system 220 shall only be described with reference to one of the patient handling devices 222. Of course, it should be appreciated that the location detection system 220 is utilized to determine the specific locations of several patient handling devices 222 simultaneously throughout the health care facility. Multiple patient handling devices 222 may also be located in the same zone A, B.

Referring to the patient handling device 222 shown in Zone A of the room floor plan of FIG. 12, a locator 252 is fixed relative to the patient handling device 222. The locator 252 is affixed to a wall of the room, a floor of the room, or a ceiling of the room. The locator 252 may also be suspended from any location in the room such as by a tether or any other restraining mechanisms or devices adapted to maintain the locator 252 in a fixed relationship relative to the patient handling device 222. In other words, in the embodiment of FIG. 12, the locator 252 is not designed to be mobile for transport outside of the room. The locator 252 is programmed with a unique location identifier that corresponds to the location of the patient handling device 222. The unique location identifier may simply be a serial number of the locator 252 that is entered into a look-up table stored in accessible memory of the processing station 250 and associated with the zone in which the locator 252 is installed.

The processing station 250, which is remotely located relative to the patient handling device 222 and the locator 252, receives the unique location identifier such that the location of the patient handling device 222 can be determined and monitored remotely from the patient handling device 222. More specifically, a receiver 254 is supported by the patient handling device 222 and receives the unique location identifier corresponding to the location, and the communication module 248, which is electronically coupled to the receiver 254, transmits the unique location identifier of the locator 252 from the patient handling device 222 to the processing station 250. As a result, the patient handling device 222 acts as a communication link between the locator 252 and the processing station 250. About the same time, the communication module 248 transmits or communicates a unique ID of the patient handling device 222 to the processing station 250 such that the processing station 250 can correlate the location of the patient handling device 222 with the unique ID of the patient handling device 222.

A separate look-up table is utilized by the processing station 250 to correlate the unique ID to a patient for which the specific patient handling device 222 is associated. The processing station 250 then correlates the unique ID and patient to the particular zone in which the specific patient handling device 222 is now located such that the software application installed on the processing station 250 can accurately manage data corresponding to the specific patient handling device 222 and the patient.

In one embodiment, the locator 252 includes at least one infrared transmitter 256 for transmitting the unique location identifier to the receiver 254 and the receiver 254 includes a housing supporting at least one infrared sensor 258 for receiving the unique location identifier from the infrared transmitter 256. In this instance, transmitting the unique location identifier from the locator 252 to the patient handling device 222 is further defined as transmitting an infrared location signal from the at least one infrared transmitter 256 of the locator 252 to the at least one infrared sensor 258 of the receiver 254. Those skilled in the art appreciate that other data, besides the unique location identification may also be transmitted from the infrared transmitter 256, e.g., battery strength of a battery 260 in the locator 252, time/date, etc.

The receiver 254 is configured to include at least one infrared transmitter 256 for transmitting a request signal to the locator 252. Likewise, the locator 252 is configured to include at least one infrared sensor 258 to receive the request signal from the receiver 254. The battery 260, rechargeable or otherwise, is used to power the locator 252. To conserve battery life, the locator 252 normally operates in a sleep mode until the request signal is received by the at least one infrared sensor 258 of the locator 252.

Figure 13:
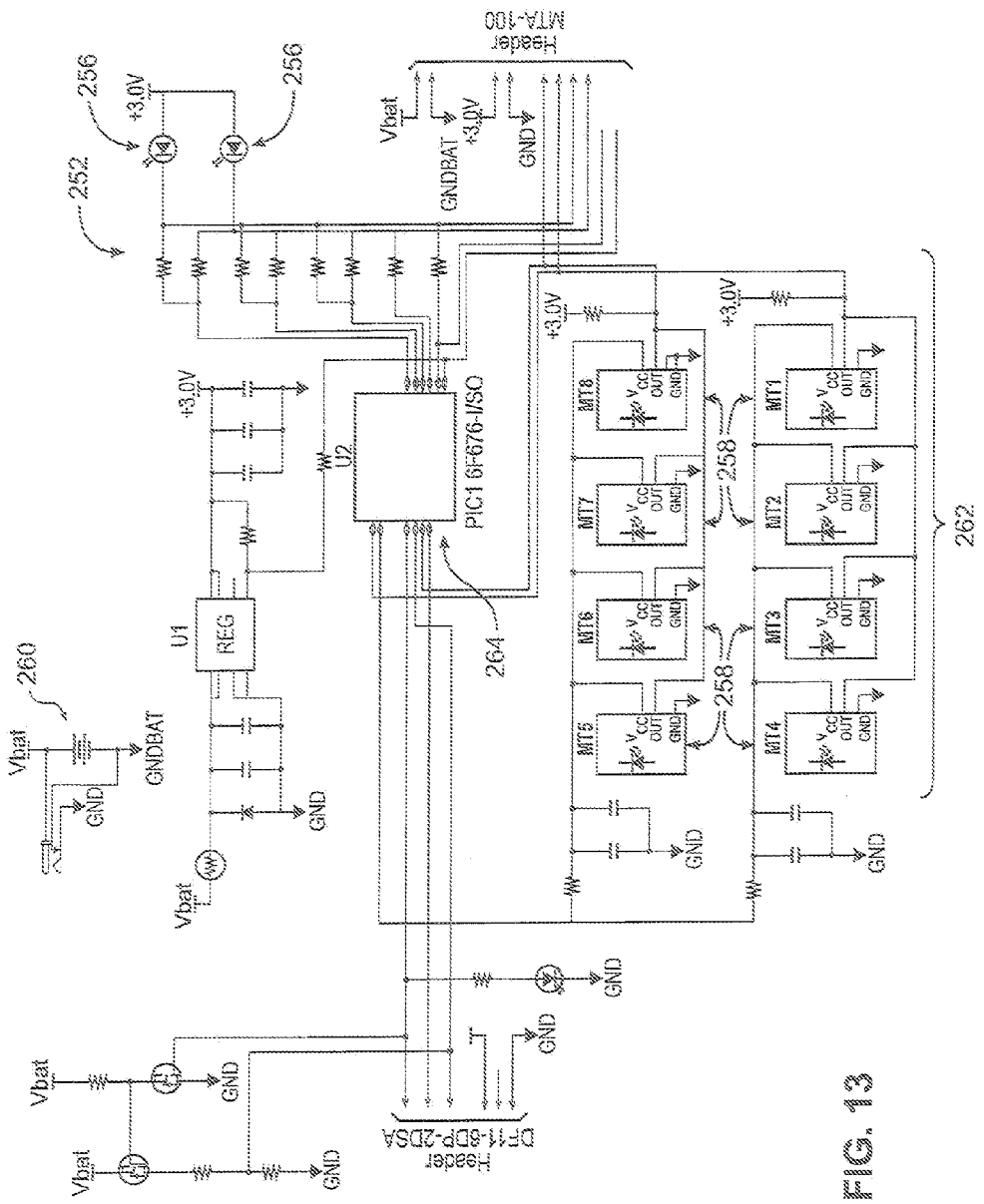
FIG. 13 is an electrical schematic of the locator of FIG. 12.

Referring to the electrical schematic of FIG. 13, one embodiment of the locator 252 is shown in more detail. In this embodiment, the locator 252 includes a plurality of infrared transmitters 256 for transmitting the unique location identifier to the receiver 254. Likewise, the locator 252 includes a plurality of infrared sensors 258 arranged in a sensor array 262 for receiving the request signal from the receiver 254. The locator 252 also includes a microprocessor 264 electrically coupled to the sensor array 262 and the infrared transmitters 256. The microprocessor 264 is pre-programmed with the unique location identifier that corresponds to the location of the patient handling device 222 and controls the infrared transmitters 256 to produce a signal with the unique location identifier and transmit the signal to the receiver 254 of the patient handling device 222. The infrared transmitters 256 of the locator 252 are adapted to provide variable power transmission to minimize cross talk and maximize signal integrity. The locator 252 is also adapted to modulate light intensity from the infrared transmitters 256 to maximize noise immunity. Finally, a filter (not shown) may be used to filter the infrared signal to reduce receiver saturation and maximize signal integrity and noise immunity.

Figure 14:
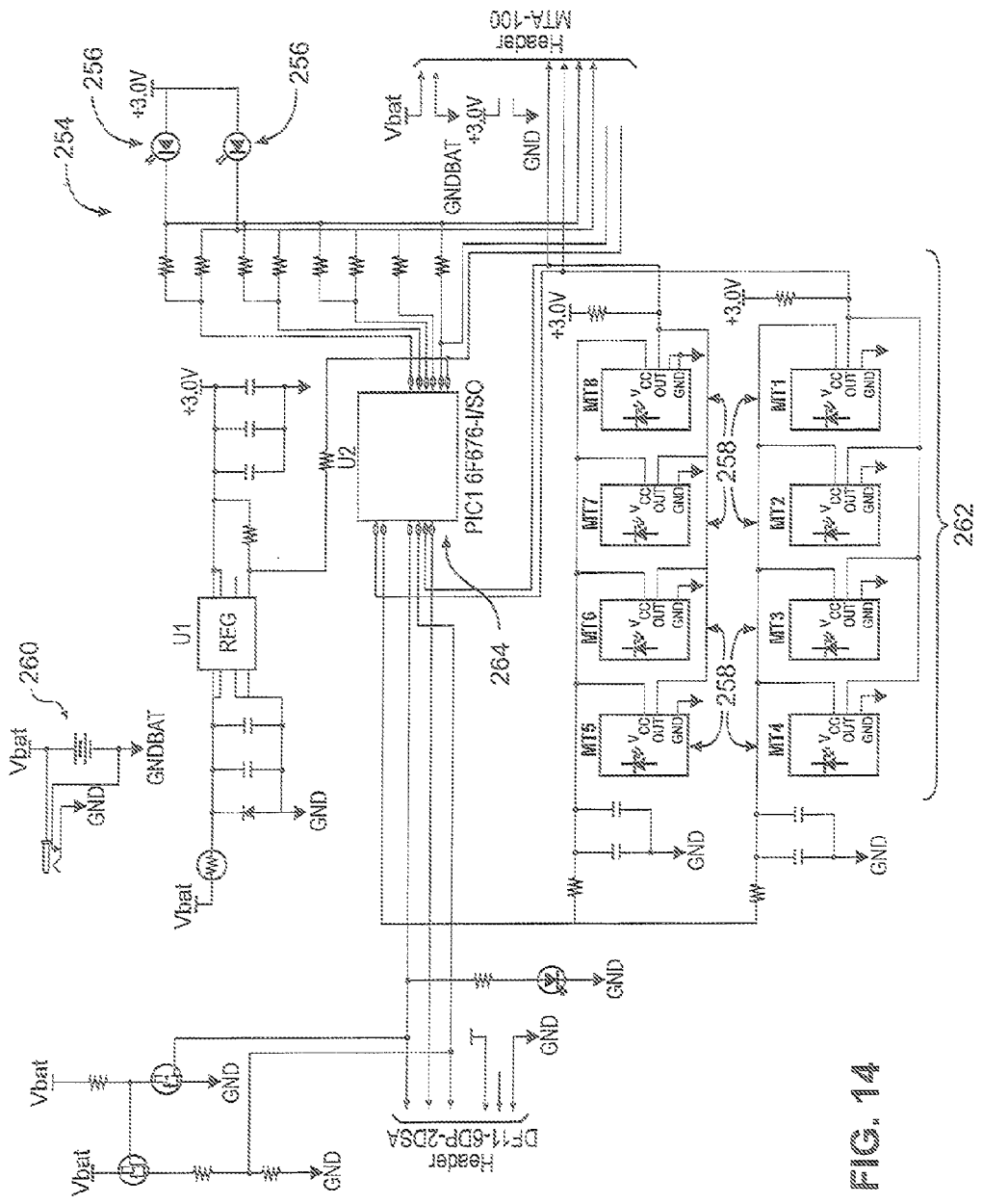
FIG. 14 is an electrical schematic of the receiver of FIG. 12.

Referring to the electrical schematic of FIG. 14, one embodiment of the receiver 254 of the patient handling device 222 is shown in more detail. In this embodiment, the receiver 254 includes a plurality of infrared sensors 258 arranged in a sensor array 262 for receiving the unique location identifier from the infrared transmitters 256 thereby improving transmission of the unique location identifier. Likewise, the receiver 254 includes a plurality of infrared transmitters 256 for transmitting the request signal from the receiver 254 to the locator 252 thereby improving transmission of the request signal. The receiver 254 may also be battery powered, but is preferably powered by an AC power source used to power a control system and the CPU 244 of the patient handling device 222. Those skilled in the art realize that the locator 252 and receiver 254 may each be implemented with a single infrared transmitter 256 and infrared sensor 258.

Figure 15:
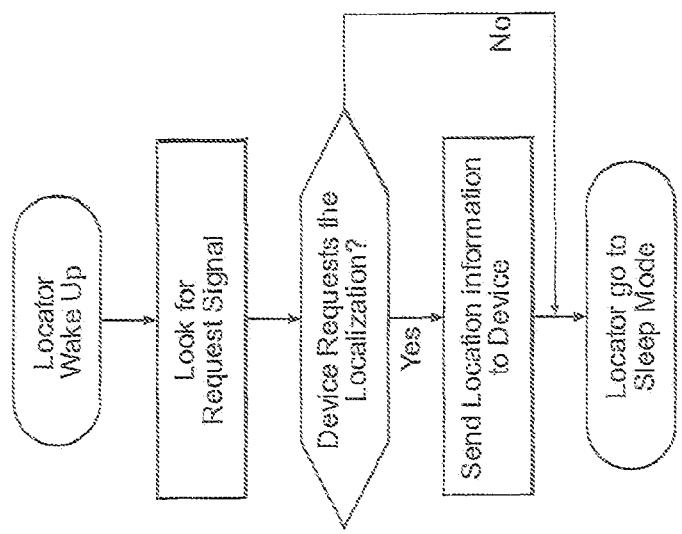
FIG. 15 is a process flow diagram illustrating a process for transmitting the unique location identifier from the locator to the receiver.

Referring to FIG. 15, a process flow diagram illustrates a method of detecting the location of the patient handling device 222. Initially, the locator 252 is in the sleep mode and awaits the request signal from the receiver 254. In other words, the microprocessor 264 looks on a reception channel to see if the patient handling device 222 has requested location information, e.g., the unique location identifier. If the patient handling device 222 has not requested the unique location identifier, the locator 252 remains in the sleep mode. If the patient handling device 222 sends the request signal and the request signal is properly received and understood by the locator 252, then the location signal sends the location information, i.e., the unique location identifier on a transmission channel. Once the unique location identifier is sent, the locator 252 returns to the sleep mode to conserve battery life.

Figure 16:
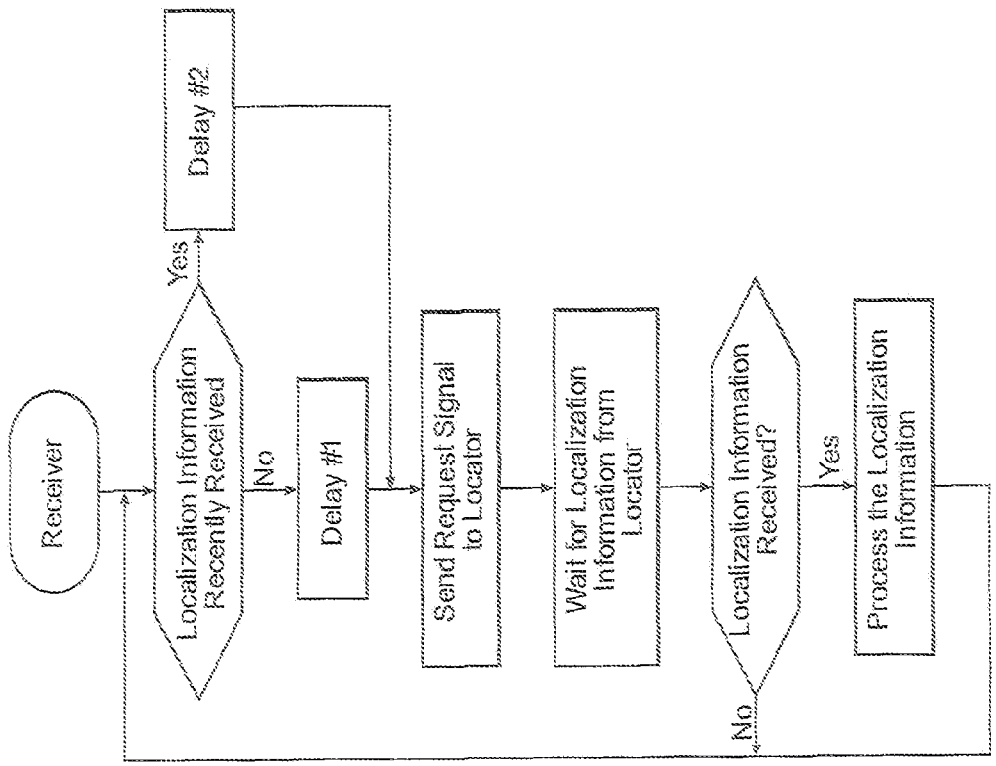
FIG. 16 is a process flow diagram illustrating a process for requesting the unique location identifier from the locator.

Referring to FIG. 16, a process flow diagram illustrates a method of sending the request signal to the locator 252 from the receiver 254. The receiver 254, which is preferably powered by an AC power source, regularly transmits the request signal to continually update the location of the patient handling device 222. The timing of these transmissions can differ depending on whether or not the receiver 254 has recently received the location information or not. As a result, there may be multiple predetermined delays between request signals, e.g., delay #1 and delay #2, which differ in the amount of time between transmissions of the request signal to the locator 252 on a transmission channel of the receiver 254. Once the location information is received, the information is processed and the unique location identifier is sent on to the CPU 244 and ultimately the processing station 250 to determine the location of the patient handling device 222.

Figure 17:
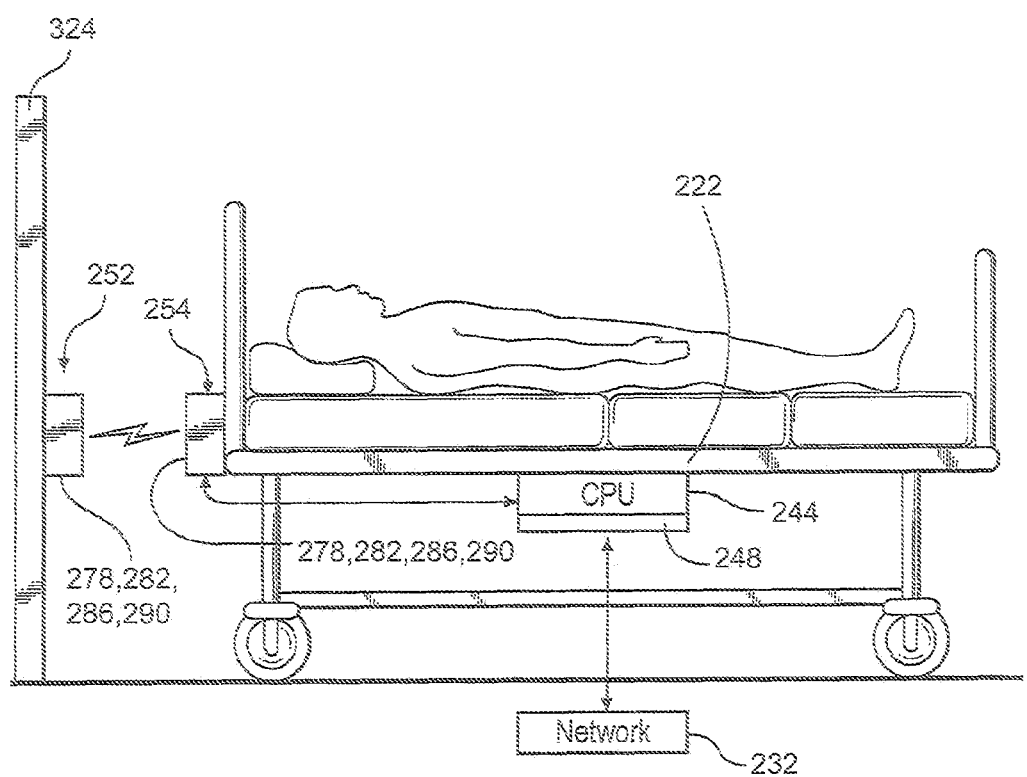
FIG. 17 is a perspective view illustrating alternative location detection systems utilizing radio frequency, magnetic inductance, ultrasonic, or modulated light systems.

Referring to FIG. 17, alternative location detection systems are shown with similar features to that of the previously described embodiment. In FIG. 17, the locator 252 may be one of: a radio frequency identification (RFID) tag 276 for transmitting the unique location identifier using radio frequency; an ultrasonic transmitter 280 for transmitting the unique location identifier using ultrasonic signals; an inductively coupled transmitter 284 for transmitting the unique location identifier using principles of magnetic inductive coupling; or a modulated light transmitter 288 for transmitting the unique location identifier using modulated light. It should be appreciated that in each of these embodiments, the receiver 254 is particularly adapted for receiving the specific signal types mentioned, i.e., the receiver 254 may be a RFID reader 278, or include an ultrasonic sensor 282, an inductively coupled sensor 286, or a modulated light sensor 290.

Referring to FIGS. 18-21, further alternative systems using RFID are shown. It should be appreciated that any of the systems using RFID could be active, semi-active, or passive RFID systems as is well known to those skilled in the art. In general, when a passive system is employed, each of the tags 276 described contains a transponder (not shown) with a digital memory chip (not shown) that is given or programmed with the unique location identifier. An interrogator (not shown), which is an antenna packaged with a transceiver and decoder in the RFID reader 278 emits a signal activating the RFID tags 276 so that the interrogator can read and write data to the RFID tags 276. When the patient handling device 222 is moved into the particular zone in the room, the RFID tags 276 detect the RFID reader's activation signal. The RFID reader 278 then decodes the data, e.g., the unique location identifier, encoded in the RFID tag's digital memory chip and the data is passed to the processing station 250 as previously described.

Figure 18:
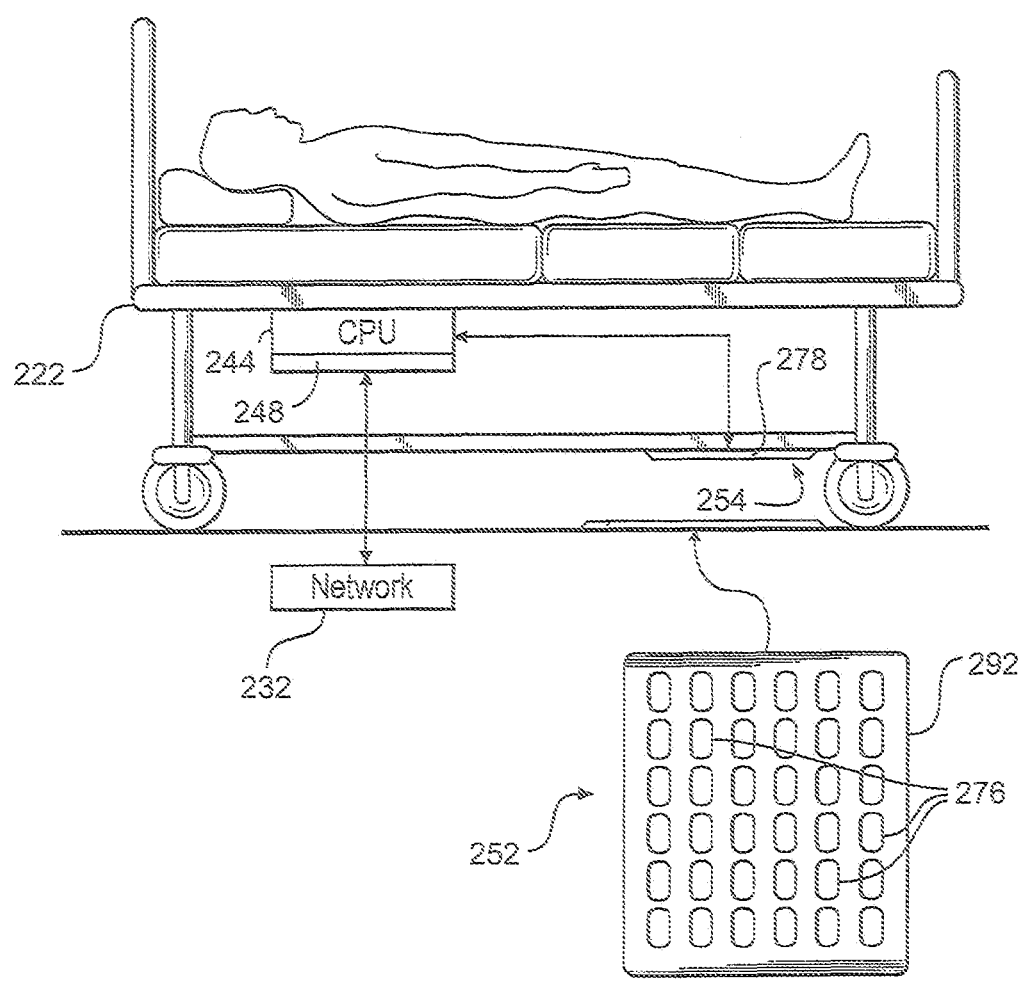
FIG. 18 is a perspective view illustrating an alternative location detection system utilizing an array of RFID tags.

In the embodiment of FIG. 18, the locator 252 comprises an RFID tag mat 292 that includes an array of RFID tags 276. At least one of the tags 276 transmits the unique location identifier, or a selected set of the RFID tags 276 transmits a signal that is recognized as the unique location identifier. In this embodiment, the receiver 254 is an RFID reader 278 for receiving the signals from the RFID tags 276. In use, the healthcare professional or other employee of the healthcare facility would first move the patient handling device 222 into position either over the RFID tag mat 292 or in close proximity to the RFID tag mat 292. The RFID tags 276, or at least a portion thereof, would then transmit the unique location identifier to the RFID reader 278, which would then transmit the unique location identifier to the CPU 244 and then to the processing station 250 located on the network 232 via the communication module 248, as previously described.

Figure 19:
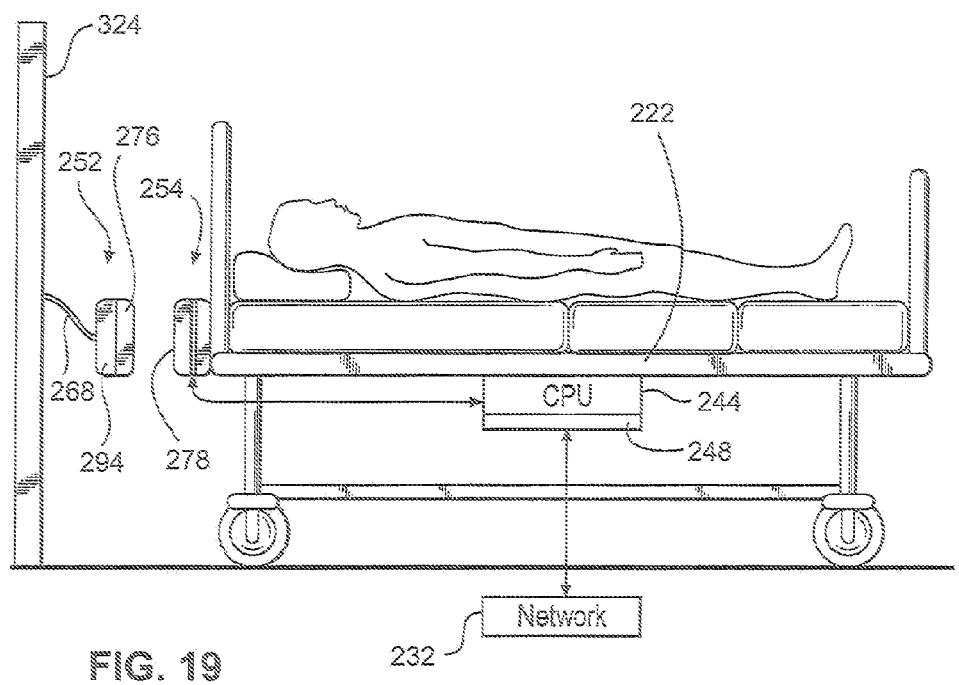
FIG. 19 is a perspective view illustrating an alternative location detection system utilizing an RFID swipe card.

In the embodiment of FIG. 19, the locator 252 comprises an RFID swipe card 294 having at least one active or passive RFID tag 276. The RFID swipe card 294 is tethered to a head wall 324 of the room using a tether 268. This fixes the RFID swipe card 294 in the room relative to the patient handling device 222. The receiver 254 is an RFID reader 278 that receives the unique location identifier from the RFID tag 276 embedded in the RFID swipe card 294. In this embodiment, a healthcare professional would first move the patient handling device 222 into position in the particular zone in the room and then swipe the RFID swipe card 294 over the RFID reader 278 to transfer the unique location identifier from the RFID tag 276 to the RFID reader 278 and on to the processing station 250.

Figure 20:
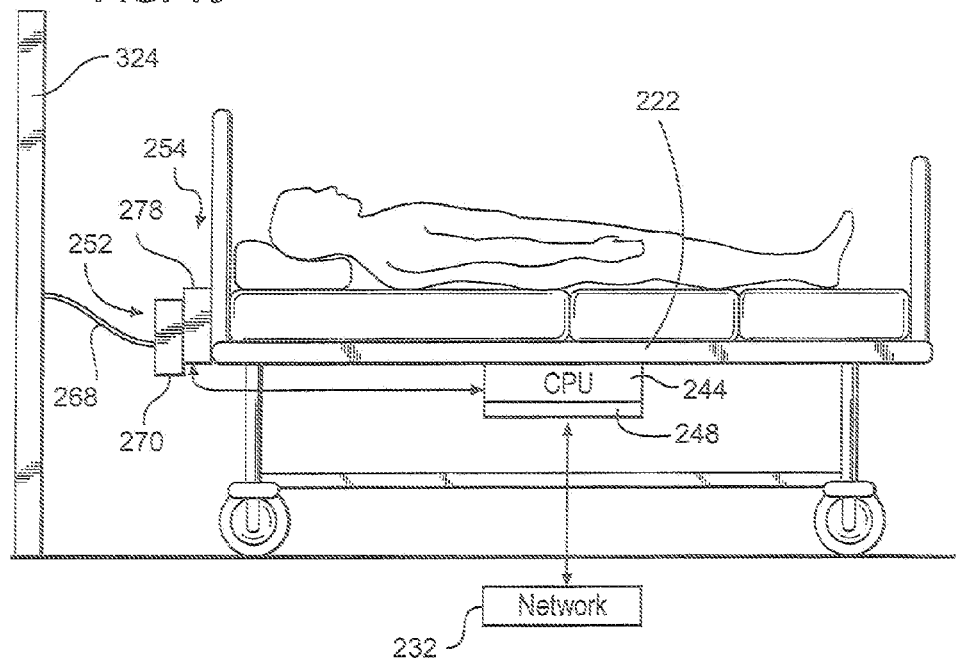
FIG. 20 is a perspective view illustrating an alternative location detection system utilizing a tethered RFID magnet tag.

In the embodiment of FIG. 20, the locator 252 comprises a magnetic RFID tag 270. The magnetic RFID tag 270 is tethered to the head wall 324 as in FIG. 19, using a tether 268. However, in this embodiment, the healthcare professional or other employee of the healthcare facility does not merely swipe the magnetic RFID tag 270 to transmit the unique location identifier to the RFID reader 278. Instead, the RFID reader 278 magnetically attracts the magnetic RFID tag 270 to releasably lock the magnetic RFID tag 270 to the RFID reader 278 to ensure a complete transmission of the unique location identifier to the processing station 250 in the manner described above.

Figure 21:
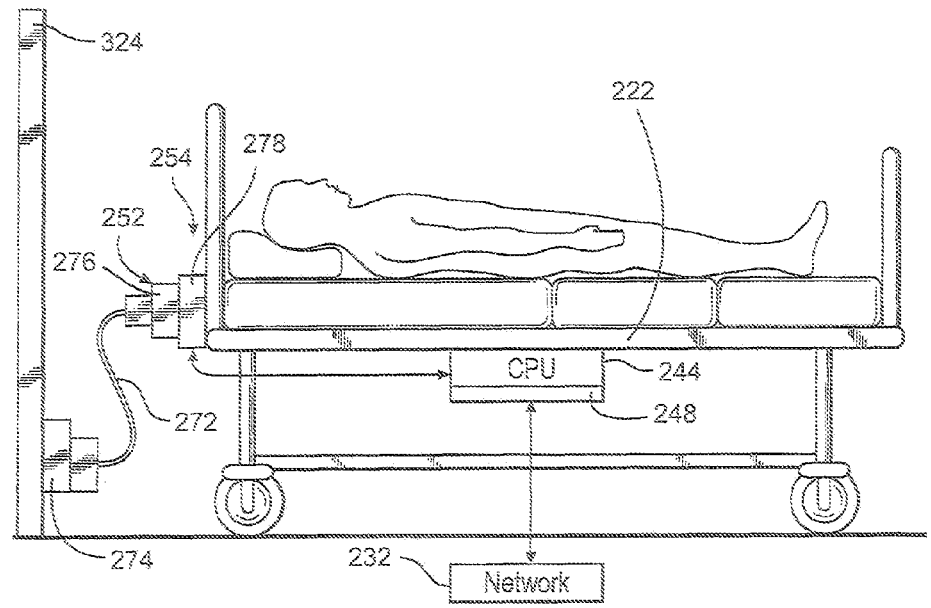
FIG. 21 is a perspective view illustrating an alternative location detection system utilizing a nurse call cable with an integrated RFID tag.

In the embodiment of FIG. 21, the locator 252 comprises an RFID tag 276 and the receiver 254 comprises an RFID reader 278 similar to FIGS. 18-20. However, this embodiment further includes a cable 272 that would be maintained at each zone A, B. The cable 272 interconnects a nurse call interface of the patient handling device 222 to a standard nurse call interface port 274 located at each zone A, B. The RFID reader 278 is integrated into the nurse call interface located on the patient handling device 222 and the RFID tag 276 is integrated into an end of the cable 272 such that when the cable 272 connects the nurse call interface on the patient handling device to the nurse call interface port 274 mounted to the head wall 324, the RFID tag 276 would transmit the location information, e.g., unique location identifier, to the RFID reader 278 and on to the processing station 250 located on the network 232.

Figure 22:
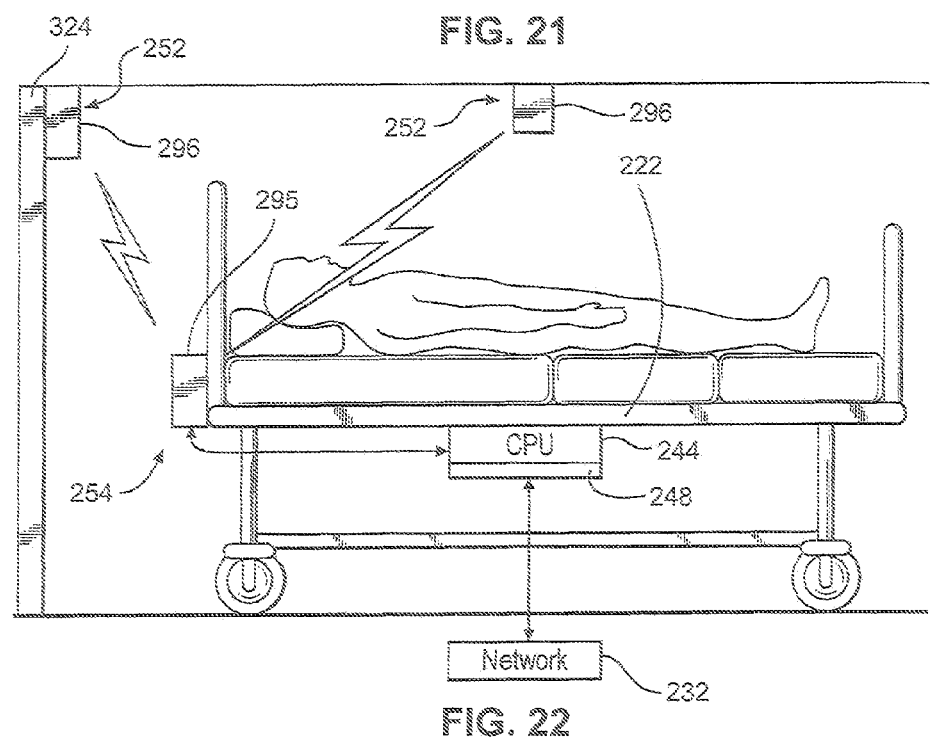
FIG. 22 is a perspective view illustrating an alternative location detection system utilizing WiFi access points.

Referring to FIGS. 22-25, further alternative systems are shown. In the embodiment of FIG. 22, the locator 252 comprises a plurality of WiFi access points 296 located throughout the room and programmed with unique location identifiers for the zones in the room in which they are located. This system is capable of triangulating the room and zone location of the patient handling device 222 using the WiFi access points 296. The receiver 254 further comprises a WiFi transceiver 95 mounted to the patient handling device 222. The WiFi transceiver is in communication with the WiFi access points 296 to receive reference signals transmitted by the WiFi access points 296. In some embodiments, the strength of the signal received in combination with the unique location identifiers programmed into the WiFi access points 296 could be used to triangulate the room and zone location of the patient handling device 222. The WiFi transceiver 95 communicates the location information to the processing station 250 located on the network 232.

Figure 23:
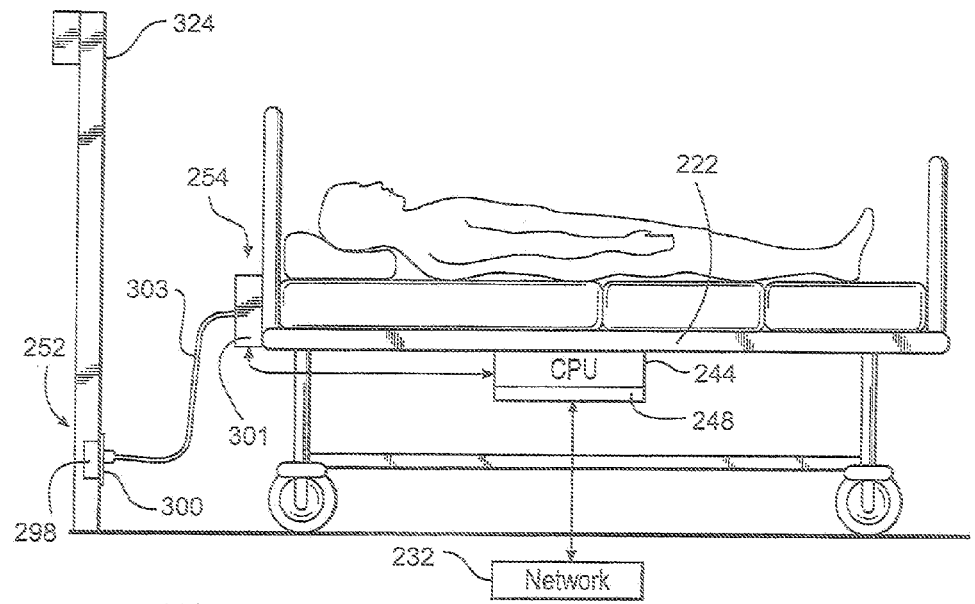
FIG. 23 is a perspective view illustrating an alternative location detection system utilizing a power cord with and integrated ID transmitter.

In the embodiment of FIG. 23, the locator 252 comprises an ID transmitter 298 integrated into a 110 Volt AC plug 300 that transmits a reference signal to the receiver 254 located on the patient handling device 222. In this embodiment, the receiver 254 is integrated into a power cord interface 301 to communicate with the ID transmitter 298 through a power cord 303. The receiver 254 would then communicate the location information, e.g., unique location identifier, to the processing station 250 located on the network 232.

Figure 24:
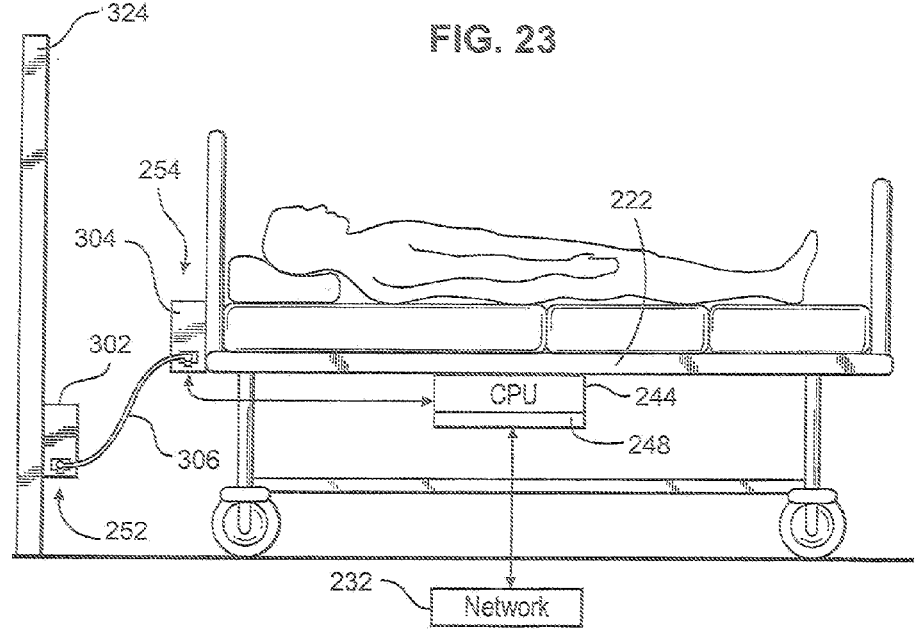
FIG. 24 is a perspective view illustrating an alternative location detection system utilizing an Ethernet port to transmit the unique location identifier.

In the embodiment of FIG. 24, the locator 252 comprises an Ethernet port 302 and the receiver 254 comprises an Ethernet transceiver 304 mounted to the patient handling device 222. An Ethernet-compliant cable 306 interconnects the Ethernet transceiver 304 and the Ethernet Port 302 to send location information to the patient handling device 222. The Ethernet transceiver 304 then communicates the location information to the processing station 250.

Figure 25:
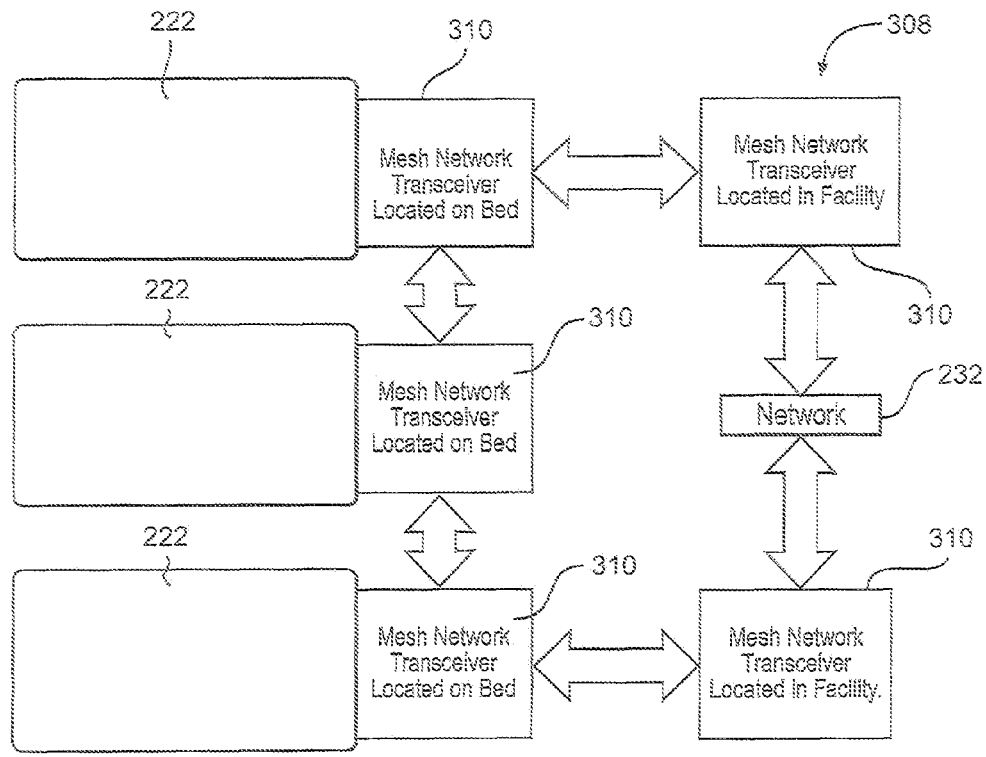
FIG. 25 is a schematic view illustrating an alternative location detection system utilizing a mesh network to determine the location of the patient handling device.

In the embodiment of FIG. 25, the system utilizes a mesh network 308 with mesh network transceivers 310 to determine the location information. The mesh network 308 may be wired or wireless, preferably wireless to reduce infrastructure costs. The wireless mesh network 308 allows mesh network transceivers 310 to transmit data through one another onto the network 232 and the processing station 250. In other words, in the wireless mesh network 308, access points and wireless devices can organize themselves into an ad hoc network, communicating with each other to determine the fastest way to send data to the network 232. In the wireless mesh network 308, data hops from mesh network transceiver 310 to mesh network transceiver 310 looking for the shortest available path to the network 232 and the processing station 250. Here, each of the patient handling devices 222 is equipped with a mesh network transceiver 310, which acts as a node on the mesh network 308. The location information is obtained by knowing the association of the mesh network transceivers 310 on the patient handling devices 222 relative to the other mesh network transceivers 310 and/or a base transceiver (not shown). For instance, adjacent patient handling devices 222 in a second zone of the room, e.g., Zone B of Room 1, could determine the location information using the mesh network transceiver 310 on the patient handling device 222 in Zone A of Room 1.

Referring to FIGS. 26-29, alternative location detection systems are shown for determining the location in which the patient handling device 222 is located by separately determining first and second areas of the location. In one embodiment, the first area is the room, e.g., Room 1, in which the patient handling device 222 is located, and the second, subarea, is the zone in the room in which the patient handling device 222 is located, e.g., zones A, B. One of the previously described location detection systems may be used to determine the first area in which the patient handling device 222 is located. In this instance, the previously described systems would be enabled to only provide first area or room locations and not specific zone locations. In other words, the previously described systems would provide a first locating device, e.g., locator 252, mesh network transceiver 254, etc., associated with the patient handling device 222 and in communication with the processing station 250 to transmit a first unique location identifier to the processing station 250. The first unique location identifier being associated with the first area in which the patient handling device 222 is located, but not the subarea or particular zone in which the patient handling device 222 is located.

The asset tracking system 242 of the healthcare facility could also be the first locating device used for this purpose. In this instance, each of the patient handling devices 222 would be equipped with an asset tag 314 for tracking the patient handling devices 222 in the healthcare facility with the asset tracking system 242 being adapted to provide room locations for the patient handling devices 222 and transmit those room locations to an asset tag receiver 316 on the network 232, and on to the processing station 250. For purposes of description, reference is made to the first locating device being the asset tracking system 242.

Figure 26:
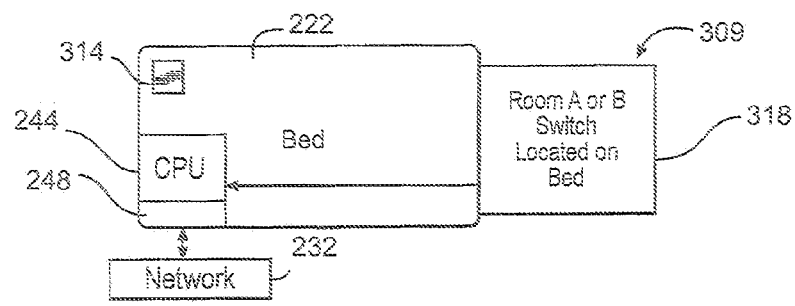
FIG. 26 is a schematic view illustrating an alternative location detection system utilizing an asset tag in combination with a switch.

The alternative location detection systems of FIGS. 26-29 provide a second locating device 109 associated with the patient handling device 222 and in electronic communication with the processing station 250 to transmit a second unique location identifier to the processing station 250. The second unique location identifier corresponds to the subarea or zone in which the patient handling device 222 is located. Thus, the first unique location identifier provides the general vicinity in which the patient handling device 222 is located, while the second unique location identifier further refines the description of the location to pinpoint the location of the patient handling device 222. Referring first to FIG. 26, the second locating device may be an electronic switch 318 that can be manually actuated to correspond to the appropriate zone A, B. The switch 318 would be in communication with the network 232 and processing station 250 to identify the zone A, B selected.

Figure 27:
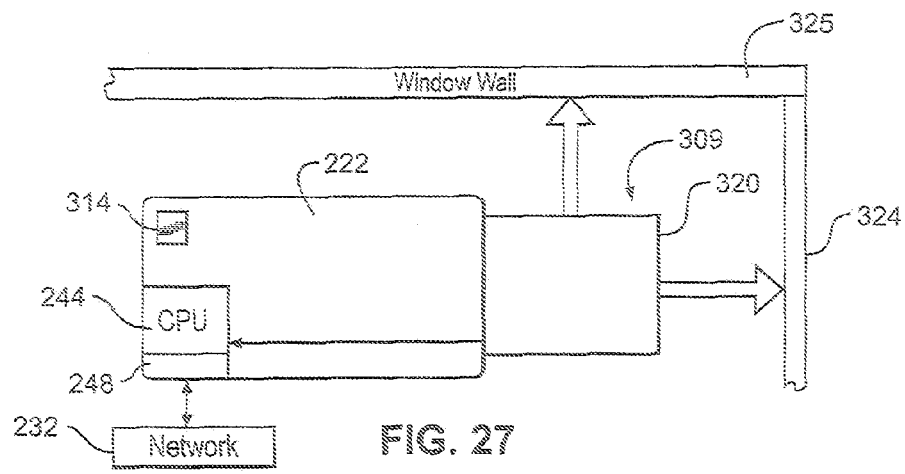
FIG. 27 is a schematic view illustrating an alternative location detection system utilizing an asset tag in combination with a sonic distance finder.
Figure 28:
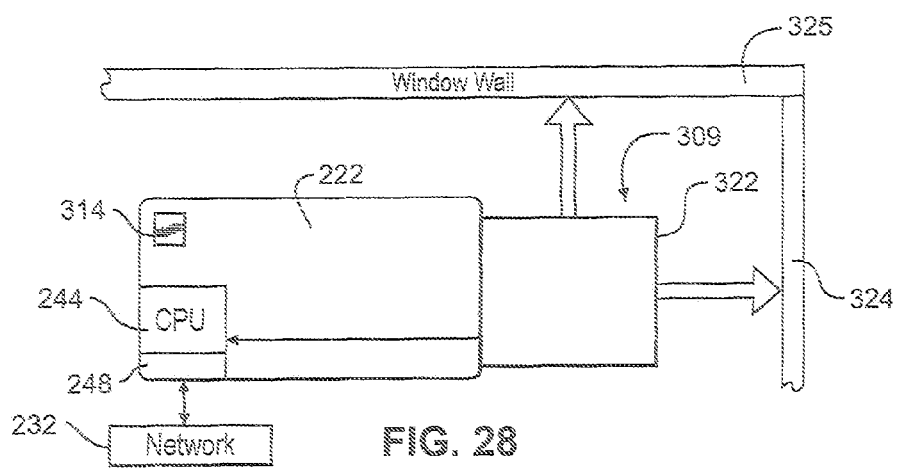
FIG. 28 is a schematic view illustrating an alternative location detection system utilizing an asset tag in combination with a laser distance finder.

Referring to FIGS. 27 and 28, the second locating device 109 is a sonic distance sensor 320 or a laser distance finder 322 used to determine the zone A, B in which the patient handling device 222 is located. In these embodiments, the sonic distance sensors 320 or laser distance finders 322 would be adapted to generally measure distances from walls 324, 325 located in the first area, e.g., Room 1, to further determine the position of the patient handling device 222 in the room. A look-up table could be loaded into the processing station 250 with predetermined ranges of distances provided to correspond to the different zones A, B. For instance, once the patient handling device 222 is wheeled or moved into room, the sonic distance sensors 320 or laser distance finder 322 may be manually or automatically operated to measure the distance from predetermined boundaries, e.g., walls 324, 325, with the measured distances being compared to the look-up table and with a corresponding zone A, B selected therefrom.

Figure 29:
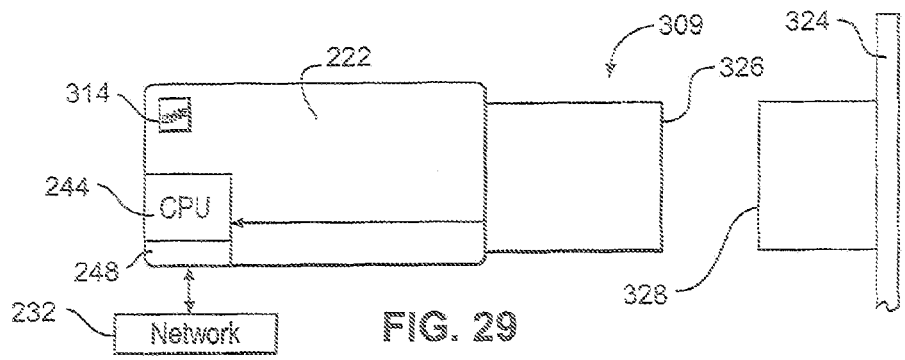
FIG. 29 is a schematic view illustrating an alternative location detection system utilizing an asset tag in combination with a Hall Effect sensing system.

Referring to FIG. 29, the second locating device is a hall-effect sensor 326 operable with a room magnet 328 or plurality of room magnets 328 located in the room to determine the zone location of the patient handling device 222. In each of the embodiments of FIGS. 26-29, the sonic distance sensors 320, laser distance finder 322, and hall-effect sensor 326 would be adapted to transmit signals that communicate, either directly or indirectly, with the processing station 250 to display the room and zone location of the patient handling device 222. In one version, the communication module 248 is in electronic communication with these second locating devices 109 and the processing station 250 to transmit the second unique location identifier from the second locating devices 109 to the processing station 250. Again, as with the previously described embodiments, the patient handling device 222 has a unique ID and the communication module 248 communicates the unique ID to the processing station 250 such that the processing station 250 can correlate the first unique location identifier and the second unique location identifier to the patient handling device 222 to determine the room and zone location of the patient handling device 222.

Figure 30:
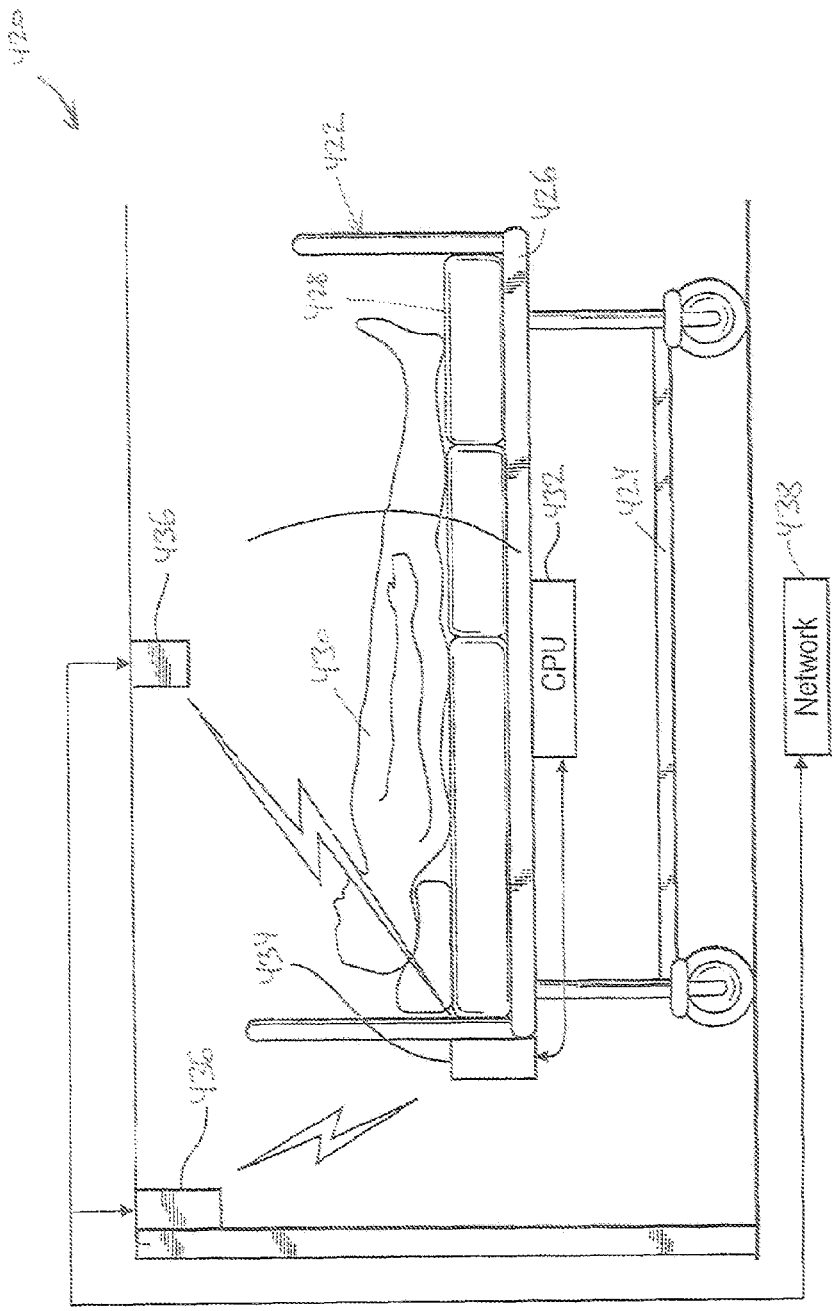
FIG. 30 is a schematic view illustrating another alternative location detection system utilizing fixed wireless access points and a mobile transceiver positioned on-board a person support apparatus.

FIG. 30 depicts another alternative location detection system 420. Location detection system 420 includes a person support apparatus 422 having a base 424, a frame 426, and a support surface 428 adapted to support a person 430 thereon. Person support apparatus 422 also includes a controller 432 that is in communication with a wireless transceiver 434. Wireless transceiver 434 communicates wirelessly with one or more wireless access points 436. Wireless access points 436 are in communication with a local area network 438 of the healthcare facility in which person support apparatus 422 is located. In some embodiments, local area network 438 is an Ethernet-based computer network.

Controller 432 includes one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Wireless access points 436 are, in at least one embodiment, conventional WiFi access points (IEEE 802.11) that allow wireless devices—such as, but not limited to, wireless transceivers 434—to connect to computer network 438. Wireless transceivers 434 are, in at least one embodiment, conventional WiFi transceivers capable of communicating with network 438 via access points 436.

Location detection system 420 (FIG. 30) operates to determine the location of person support apparatus 422 by communicating with one or more of the wireless access points 436. Each WiFi access point 436 sends messages that are received by wireless transceiver 434. Wireless transceiver 434 includes an antenna and circuitry that is adapted to determine a received signal strength indicator (RSSI) of at least one of the messages sent from the wireless access points 436 in which it is in communication with. In an alternative embodiment, wireless transceiver 434 includes circuitry that is adapted to determine a received channel power indicator (RCPI) of at least one of the messages sent from each of the wireless access points 436 that it receives a message from. In still other embodiments, wireless transceiver 434 includes circuitry that is adapted to determine both an RSSI and a RCPI of at least one of the messages sent from each of the wireless access points 436 that it receives a message from.

Each wireless access point 436 includes within at least one of the messages that it sends to wireless transceiver 434 a media access control (MAC) address of that particular wireless access point 436. Location detection system 420 includes a map of the location of each wireless access point 436 that is stored in an electronic memory (not shown). The map includes data indicating the location of each access point 436 within the facility, as well as an identification of which floor each wireless access point 436 is located on in a multi-story facility. Each of the individual wireless access points 436, in at least one embodiment, are identified in the map data using their respective MAC address. The map data therefore includes a location within the facility for each of the MAC addresses of the wireless access points 436.

In one embodiment, the map data is stored in a memory that is on-board person support apparatus 422 and electronically accessible to controller 432. In this embodiment, person support apparatus 422 determines an estimate of its location within the facility based upon this map data and the signal strength data (RSSI and/or RCPI) of the messages it receives from wireless access points 436. In another embodiment, the map data is stored on a server, or other device (e.g. processing station 250 of FIG. 11), that is on computer network 438. In such an embodiment, the server or other network device determines an estimate of the location of person support apparatus 422 based upon this map data and the signal strength data (RSSI and/or RCPI). After determining the location estimate of the person support apparatus 422, the server or other network device—in some embodiments—transmits a message to that particular person support apparatus 422 that identifies the current location of person support apparatus 422. As will be discussed in greater detail below, once person support apparatus 422 knows its location, either from determining it itself or receiving it from a server or other network device, person support apparatus 422 then communicates this location data—in some embodiments—to other person support apparatuses, a nurse call system, and/or other devices.

The location estimate of person support apparatus 422, determined by either controller 432 or a network device, is determined by triangulating and/or trilaterating signal strength data and location data corresponding to multiple wireless access points 436. Where wireless transceiver 434 is in communication with more wireless access points 436 than is necessary to estimate its position, the location estimate is enhanced by utilizing signal strength data from all of the wireless access points and a computation of a best fit of all of the available data, in at least some embodiments. In other embodiments, one or more of the signal strength indicators are discarded by the processor or server when more wireless access points 436 are in communication with transceiver 434 than are necessary to determine the location of person support apparatus 422.

The number of wireless access points 436 that person support apparatus 422 must be in communication with in order to determine its position may vary, depending upon the particulars of the facility in which person support apparatus 422 is located. For example, if person support apparatus 422 is triangulating or trilaterating its position in a single-story facility based off of communication with only two wireless access points 436, and the signal strength data is used a proxy indication of its distance from each of the wireless access points 436, then an initial estimate of its position may yield two different possible locations within the facility. However, in many situations, one of the two different possible locations can be excluded based upon other data, such as map data indicating that one of the two possible locations lies outside the facility, or in an area inaccessible to the person support apparatus. Other data may also be used to narrow the two possible locations down to one. In a multi-story facility, it may be necessary in least some situations, to communicate with at least three different wireless access points 436 in order to determine the location of person support apparatus 422. In other situations, fewer wireless access points may be sufficient.

If controller 432 of person support apparatus 422 computes the location estimate of person support apparatus 422, controller 432 then sends this location estimate, in at least one embodiment, to a device on network 438, such as, but not limited to, processing station 250 (FIG. 11). Processing station 250, whether it receives the location estimate from person support apparatus 422 or computes the location estimate itself, then shares this location data with one or more other servers, or other devices, that are coupled to network 438. Such other servers that may receive this location data include a server of admission, discharge, and tracking system 224 (FIG. 11), a server of eICU system 228, a server of patient throughput system 226, and/or a server of asset tracking system 242. Any of these systems may then communicate this location data to still other devices, such as, but not limited to, laptops 240, personal digital assistants 238, wireless badges 246, smart phones, and/or still other devices that are in communication with network 438.

In facilities where there are multiple person support apparatuses, each person support apparatus 422 also sends a unique identifier to network 438 that uniquely identifies that particular person support apparatus 422. This identifier is used by devices on the network, such as processing station 250, to distinguish the multiple person support apparatuses 422 from each other. Thus, in at least one embodiment, person support apparatus 422 sends both a unique identifier identifying itself and signal strength data of the messages it receives from wireless access points 436 to a network device that then uses this data to determine a location of that particular person support apparatus 422 within the facility.

Figure 31:
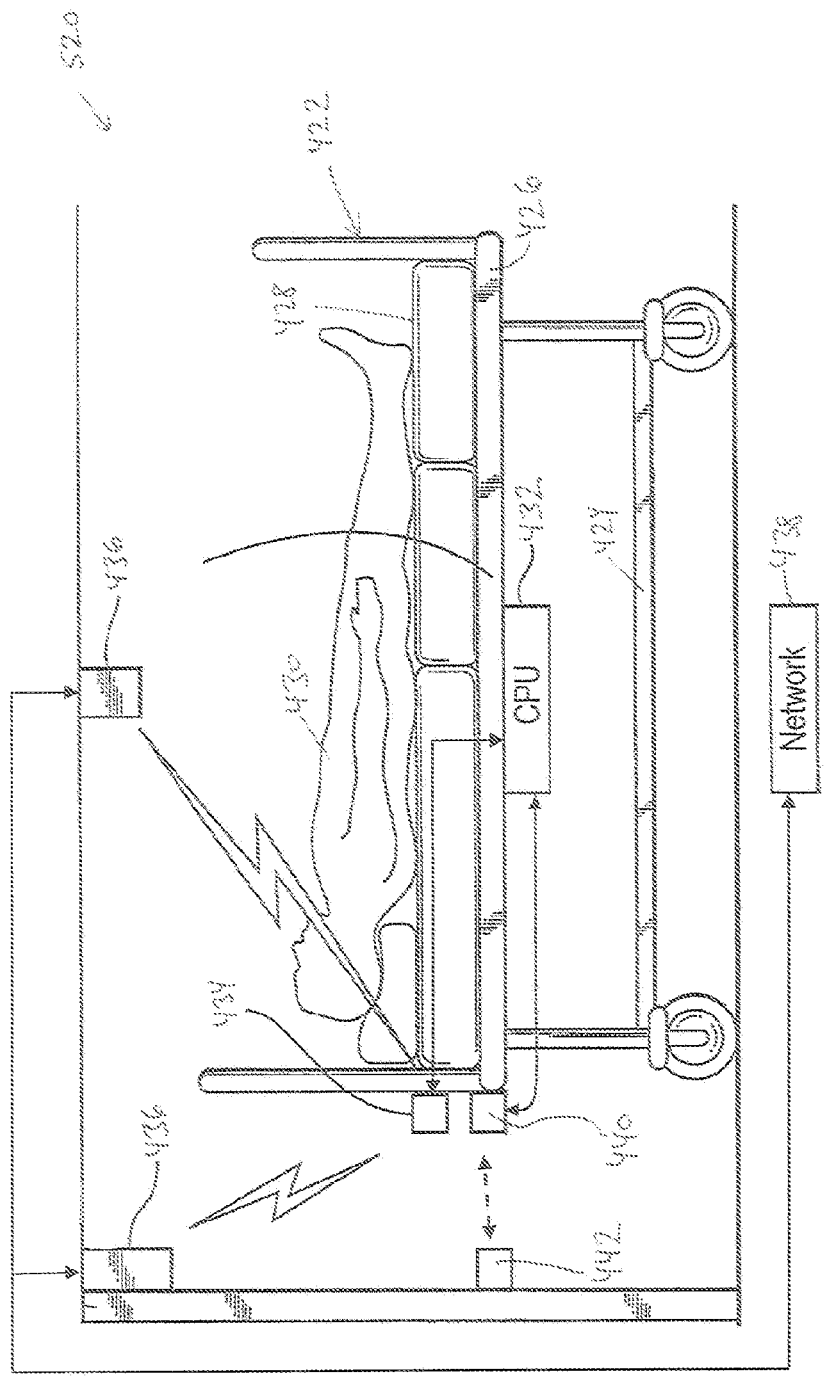
FIG. 31 is a schematic view illustrating another alternative location detection system utilizing a combination of fixed wireless access points and fixed short range locators that communicate with corresponding transceivers on-board the person support apparatus.

FIG. 31 illustrates another alternative location detection system 520. Those components of location detection system 520 that are the same as components found in location detection system 420 are labeled with the same reference number and, unless specified otherwise, operate in the same manner as previously described.

Location detection system 520 includes, in addition to those components of location detection system 420, one or more short range locators 442 that communicate with corresponding short range transceivers 440 positioned on person support apparatus 422. One or more short range locators 442 are positioned at fixed and known locations within the facility in which person support apparatus 422 is positioned. Short range locators 442 transmit wireless signals a relatively short distance, and receive wireless signals from transmitters, such as transceiver 440, when those transmitters are within a short distance of locator 442. In some embodiments, the short range is on the order of several feet. In at least one embodiment, short range locator 442 transmits an infrared signal that is only received by a short range transceiver 440 of person support apparatus 422 if person support apparatus 422 is oriented such that transceiver 440 has a line-of-sight path to locator 442 and is positioned within several feet of locator 442.

Person support apparatus 422 and/or a server on network 438 (e.g. processing station 250) determine a location estimate of person support apparatus 422 using a unique identifier that is transmitted by locator 442 to transceiver 440, as well as map data that identifies (by their unique identifier) the location of each locator 442 within the facility. For example, in one embodiment, transceiver 440, upon receiving a unique identifier from a specific locator 442, forwards the unique identifier to controller 432. Controller 432 consults the map data indicating the location of that particular locator 442 within the facility. Because locators 442 and transceivers 440 are only able to communicate over a short range, controller 432 determines that the location of person support apparatus 422 is substantially the same as the location of the particular locator 442 that its transceiver 440 is in communication with.

The granularity of the position location of person support apparatus 422 that can be determined by controller 432 is not only that of individual rooms within a facility, but also of specific zones within a particular room. Thus, for example, with reference to FIG. 12, the range of communication between fixed locators 442 and transceivers 440 is limited enough such that controller 432 is able to determine whether person support apparatus 422 is in zone A or in zone B. Stated alternatively, if person support apparatus 422 were positioned in zone A of FIG. 12, it would not be able to communicate with a locator 442 positioned at the zone B location (e.g. in the position of the locator 252 that is in zone B), and if person support apparatus 422 were positioned in zone B of FIG. 12, it would not be able to communicate with a locator 442 positioned at the zone A location.

In other embodiments, the location of person support apparatus 422 in location detection system 520 is determined by a device on network 438, such as processing station 250, rather than person support apparatus 422. In such embodiments, controller 432 forwards the unique identifier received from locator 442 to the network device via transceiver 434. The network device has access to the map data indicating the locations of each locator 442 and uses this map data and the unique identifier sent by person support apparatus 422 to determine the location of person support apparatus 422. In some embodiments, processing station 250 sends this location data back to person support apparatus 422 via communication between a network access point 436 and transceiver 434. Person support apparatus 422, in some embodiments, communicates this location estimate to other devices, including other person support apparatuses 422, a nurse call system, and/or other devices. The processing station 250, or other device on the network that determines the location estimate of person support apparatus 422, may also forward this location estimate to other devices on the network 438 in any of the manners described above with respect to location detection system 420.

In facilities where there are multiple person support apparatuses, each person support apparatus 422 also sends a unique identifier to network 438 that uniquely identifies that particular person support apparatus 422. This identifier is used by devices on the network, such as processing station 250, to distinguish the multiple person support apparatuses 422 from each other. Thus, in at least one embodiment, person support apparatus 422 sends both a unique identifier corresponding to a particular locator 442 and a unique identifier corresponding to itself to a network device that then uses these two identifiers to determine a location of that particular person support apparatus 422 within the facility.

In at least one embodiment of location detection system 520, locators 442 and transceivers 440 are the same, and operate in the same manners, as has been previously described with respect to locators 252 and receivers 254, respectively, of FIG. 12.

Location detection system 520 also includes wireless transceiver 434 which is in communication with one or more wireless access points 436. Location detection system 520 is also configured to utilize signal strength data from the messages wireless transceiver 434 receives from wireless access points 436 to enable a second estimate to be made of the location of person support apparatus 422 within the facility. That is, location detection system 520 determines an estimate of person support apparatus 422's location in any of the same manners that have been previously described above with respect to location detection system 420. Thus, location detection system 520 provides both a first location estimate generated from locators 442 and transceivers 440, and a second location estimate generated from the signal strength data of the messages received by transceiver 434 from wireless access points 436. For the first location estimate, map data indicating the location of each locator 442 is utilized, and for the second location estimate, map data indicating the location of each wireless access point 436 is utilized. Either or both of these location estimates may be determined by controller 432 or by a device on network 438, such as processing station 250.

In at least one embodiment, controller 432 and/or processing station 250 utilize only a single one of the location estimates at a given time. More specifically, in at least one embodiment, the first location estimate generated from locator 442 and transceiver 440 is used while person support apparatus 422 is stationary, while the second location estimate generated from transceiver 434 and wireless access points 436 is used while person support apparatus 422 is mobile. Such an embodiment allows the location of person support apparatuses 422 to be determined even when they are positioned out of range of any locators 442.

In at least one embodiment where the first estimate is used while person support apparatus 422 is stationary and the second estimate is used while person support apparatus 422 is mobile, a brake on board the person support apparatus 422 is used as a proxy for the stationary/mobile status of person support apparatus 422. That is, when the brake is off, controller 432 and/or processing station 250 presume that person support apparatus 422 is mobile and use the first location estimate, and when the brake is on, controller 432 and/or processing station 250 presume that person support apparatus 422 is mobile and use the second location estimate. Such embodiments include one or more brake sensors (not shown) that are in communication with controller 432. The status of the brakes is communicated to processing station 250 from controller 432, in some embodiments, via transceiver 434.

In some embodiments, the network device (e.g. processing station 250) in communication with person support apparatus 422 sends the first location estimate to another network device (e.g. asset tracking system 242 (FIG. 11) when the brake is on, and sends the second location estimate to the other network device when the brake is off. This enables not only processing station 250 to know the location of person support apparatus 422 at all times (both when it is stationary and when it is mobile), but any other device or system (e.g. systems 224, 228, 226, 242) to know the location of person support apparatus 422 at all times. Such other systems may include data tables that correlate the specific identity of person support apparatus 422 with a particular patient 430 who is occupying person support apparatus 422, thereby enabling the system to also know the location of a particular patient at all times, including times when the patient is being transported throughout the facility on person support apparatus 422.

In still other embodiments, whenever person support apparatus 422 is in communication range of a locator 442, the two location estimates are combined together to yield a third location estimate that is a combination of the first and second location estimates. The combined location estimate is a weighted or unweighted average of the two location estimates, in at least one embodiment. Other manners of combining the location estimates may also be used in other embodiments.

In some embodiments, the inclusion of dual position sensing technology (e.g. locators 442 and wireless access points 436) in location detection system 520 enables the system to be installed without having to manually calibrate person support apparatuses 422 and/or processing station 250. That is, the inclusion of the locators 442 allows the position of person support apparatus 442 to be determined, as discussed above. Using that known position information, as well as the known location of wireless access points 436, controller 432 (or processing station 250) converts the signal strength data of the messages received by person support apparatus 442 into distances. The system therefore does not rely upon a user manually calibrating, or otherwise inputting a conversion factor, into the system that controller 432 uses to convert signal strengths to distances. Once the conversion factor is known, the location of person support apparatus 422 can be determined solely by signal strength data from wireless access points 436 when person support apparatus 422 is out of range of a locator 442.

Figure 32:
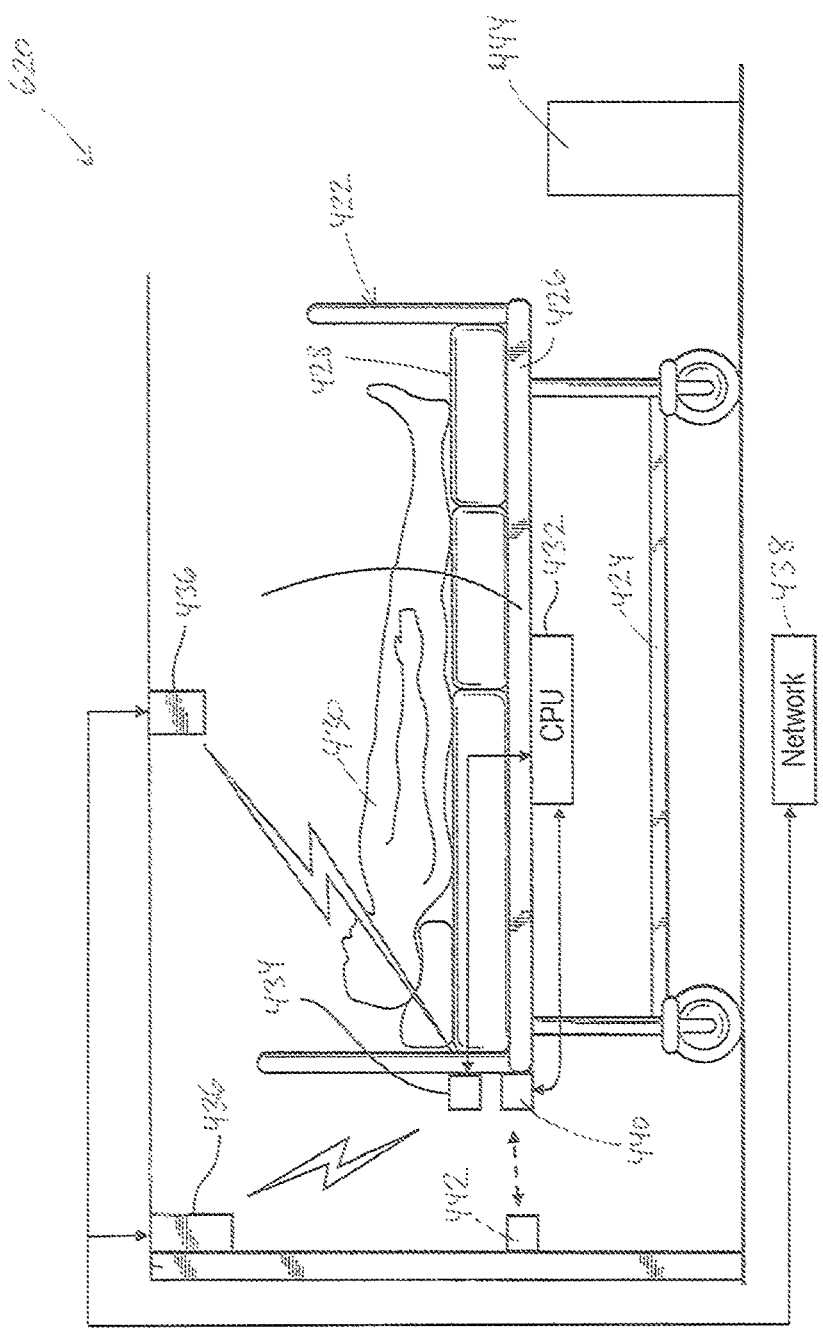
FIG. 32 is a schematic view illustrating another alternative location detection system that includes person support apparatuses adapted to communicate location information to one or more separate devices.

FIG. 32 illustrates another alternative location detection system 620. Those components of location detection system 620 that are the same as components found in location detection systems 420 and/or 520 are labeled with the same reference numbers and, unless specified otherwise, operate in the same manner as previously described.

Location detection system 620 includes, in addition to those components of location detection system 520, at least one device or object 444 that is positioned within the vicinity of person support apparatus 422 and in communication with person support apparatus 422. Device 444 is, in some embodiments, a medical device that is used in conjunction with the care of a patient who is supported or assigned to person support apparatus 422 (e.g. person 430), such as, but not limited to, a pump, a ventilator, a respirator, a monitor, or the like. In other embodiments, device 444 is another person support apparatus 422. In still other embodiments, device 444 is a powered mattress that rests on top of person support apparatus 422.

Regardless of the specific form of device 444, device 444 and person support apparatus 422 are in communication. This communication, in one embodiment, takes place via wireless transceiver 434 of person support apparatus 422 and a transceiver on-board device 444 (not shown) that utilizes the same communication protocol (e.g. WiFi, Zig-Bee, Bluetooth, etc.). In some such embodiments, communications between person support apparatus 422 and device 444 take place directly. In other embodiments, messages from person support apparatus 422 pass through a wireless access point 436 before being forwarded to device 444, and vice versa. In still other embodiments, messages from person support apparatus 422 are transmitted to wireless access point 436, from wireless access point 436 to a network device (e.g. processing station 250), from the network device back to the same (or a different) access point 436, and from that access point to device 444, and vice versa.

In still other embodiments, person support apparatus 422 includes another transceiver (in addition to transceivers 434 and 440) that uses a different communication medium and/or protocol to communicate with device 444. For example, in at least one embodiment, person support apparatus 422 includes a near field transceiver (not shown) that uses near field communication to communicate with device 444. In one embodiment, such near field communication utilizes any of the techniques and/or message content disclosed in commonly assigned U.S. patent application Ser. No. 13/802,992 filed Mar. 14, 2013 by inventors Michael Joseph Hayes et al. and entitled COMMUNICATION SYSTEMS FOR PATIENT SUPPORT APPARATUSES, the complete disclosure of which is hereby incorporated herein by reference. Other types of near field communication can also be used.

Regardless of the form of the communication between person support apparatus 422 and device 444, the content of the communication includes at least one message transmitted from person support apparatus 422 to device 444 that includes the location estimate of person support apparatus 422. The transmitted location estimate may be the first location estimate discussed above (based on locator 442), the second location estimate discussed above (based on wireless access points 436), or a location estimate that is based on a combination of the two. In some embodiments, device 444 uses this location information to determine its own location.

Either of location detection systems 420 or 520 can be modified to include the necessary structure and programming to enable person support apparatus 422 to communicate with device 444. Device 444 is configured, in some embodiments, to analyze the received signal strength of one or more messages that it receives from person support apparatus 422. This information, in combination with the location estimate of person support apparatus 422, which is sent to device 444, allows device 444 to determine its own location by triangulating and/or trilaterating its position relative to the positions of multiple person support apparatuses 422 that it is in communication with (and from which it receives location data). In other words, person support apparatus 422, in at least some embodiments, provides location information to other devices 444 in a manner similar to how wireless access points 436 provide location data to person support apparatus 422. That is, device 444 analyzes the signal strength data of messages from multiple person support apparatuses 422, along with the locations of each of the person support apparatuses, to determine its own location. The locations of person support apparatuses 422, unlike wireless access points 436, are dynamic, and device 444 therefore utilizes the location data transmitted from each person support apparatus 422, rather than a static map.

In some embodiments, device 444 determines its location using signal strength data from a combination of messages from one or more wireless access points 436 and one or more location messages transmitted from one or more person support apparatuses 422. This signal strength data is analyzed in conjunction with the current location of the person support apparatuses 422 (transmitted to device 444 from person support apparatuses 422) and in conjunction with map data stored on board device 444 that identifies the location of each individual wireless access point 436 within the facility.

In some embodiments, person support apparatuses 422 are configured such that they act as mobile hotspots for devices, such as device 444, to communicate with network 438. Device 444 utilizes signal strength data of the messages received from the hot spot person support apparatus 422, along with the location of the person support apparatus 422, to determine their location. Person support apparatuses that include circuitry for acting as mobile hot spots are disclosed in more detail in commonly assigned PCT patent application number PCT/US2014/024672 filed Mar. 12, 2014 by applicant Stryker Corporation and entitled PATIENT SUPPORT APPARATUS WITH REMOTE COMMUNICATIONS, the complete disclosure of which is hereby incorporated herein by reference. Such person support apparatuses can be modified to include any of the components, features, and/or functions described herein with respect person support apparatus 422, patient handling devices 222, and/or patient support apparatuses 20.

Any of location detection systems 420, 520, and/or 620 can also be modified such that controller 432 is configured to determine the location of person support apparatus 422 partially or wholly based upon signal strength data of messages received by person support apparatus 422 from other person support apparatuses 422. In such embodiments, for example, a first person support apparatus 422 that is in communication with two wireless access points 436 and one wireless transceiver 434 from a second person support apparatus 422 uses the signal strength data of the messages from access points 436, the location of wireless access points 436, the signal strength data of at least one message from second person support apparatus 422, and the current location of the second person support apparatus 422 (transmitted from second person support apparatus 422 to first person support apparatus 422) to determine its own location within a facility.

In still other embodiments, either of location detection system 520 or 620 can be modified to determine the location of wireless access points 436 in addition to determining the location of person support apparatuses 422. When so modified, person support apparatus 422 analyzes the signal strength of messages received from a first wireless access point 436 while positioned at a known location (as determined by locator 442 and transceiver 440). This analysis gives person support apparatus 422 information about how far away the first wireless access point 436 is positioned from person support apparatus 422's location. Person support apparatus 422 repeats this process for additional wireless access points 436 while positioned at the known location, giving person support apparatus 422 information about the range of the additional wireless access points 436. All of this information is stored on board person support apparatus 422, along with similar data that is gathered when person support apparatus 422 is moved to a different location. Using this signal strength data gathered by person support apparatus 422 when positioned at multiple different locations, person support apparatus 422 is able to triangulate and/or trilaterate the position of one or more wireless access points 436. This location data is then added to a map of the locations of wireless access point 436 that is maintained on person support apparatus 422, or it is transmitted to a network device, such as processing station 250.

Person support apparatus 422 can also share the signal strength data that it gathers from the wireless access points it is in communication with other person support apparatuses 422. In other words, in some embodiments, it is not necessary for a single person support apparatus 422 to move to multiple locations that are all in communication of a particular wireless access point 436 in order to determine the location of that wireless access point 436. Instead, multiple different person support apparatuses 422 that are all currently in communication with a particular wireless access point 436 can share with each other their current locations and the signal strengths of the messages they are currently receiving from that particular wireless access point. The person support apparatuses 422, or a network device in communication with the person support apparatuses 422, can use this data to determine a location of that particular wireless access point 436.

By having person support apparatuses 422, or a device on the network 438 that is in communication with person support apparatuses 422, determine the location of wireless access points 436, it is not necessary to manually perform a survey of the locations of wireless access points 436 and/or to transfer that surveyed data to person support apparatuses 422 (or to processing station 250). Thus, a location detection system, such as system 520 or 620, can be initially installed in a facility without having to determine the locations of wireless access points 436 (or if the locations are known, without having to transfer this information to person support apparatuses 422 and/or processing station 250), and the locations of person support apparatuses 422 can all be determined initially using locators 442 and transceivers 440. From the location data generated from using locators 442 and transceivers 440, the system can thereafter determine the locations of the wireless access points 436. Once these locations are determined, the locations of person support apparatuses 422 can thereafter be determined using signal strength data of the messages of access points 436, along with their locations, to determine the location of person support apparatuses 422. This location data supplements the locations determined from locators 442 and transceivers 440, or, as noted previously, provides location data when person support apparatuses 422 are mobile, or otherwise not positioned within communication range of a locator 442.

It will be understood that, although many of the components of location detection systems 420, 520, and 620 have been given reference numbers different from similar components in other systems and/or person support apparatuses described herein, such components are, in at least some embodiments, configured to function that same as, and/or include the same components as, the components that have been previously described. Thus, for example, in some embodiments, person support apparatuses 422 include the same functions and/or components as any of the person support apparatuses 20 or patient handling devices 222 described previously. As another example, controller 432 includes the same functions and/or components as any one or more of the following: electrical control system 44, footboard controller 48, actuator/sensor controller 50, scale system controller 52, $1^{st}$ siderail controller 54, $2^{nd}$ siderail controller 56, $1^{st}$ transceiver controller 58, $2^{nd}$ transceiver controller 60, mattress controller 62, and/or central processing unit 244. Still further, network 438, in some embodiments, includes the same components and/or functions as network 70 and/or network 232. Wireless access points 436 and transceiver 434 are the same as, or include the same functionality as, wireless access points 296 (or 68) and receiver 254, respectively. In still other embodiments, controller 432 is modified to be able to act as a mesh network node 84 in a mesh network 86 and carry out mesh network communication in any of the manners described previously.

Various alterations and changes can be made to any of the foregoing embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A location detection system comprising:
  a bed having a support surface and a wireless transceiver, the support surface adapted to support a person thereon, and the wireless transceiver adapted to wirelessly communicate with a plurality of access points of a computer network, to transmit bed status information to the computer network, and to receive messages from the plurality of access points; and a controller adapted to generate a location estimate of the bed within a hospital based upon a signal strength of the messages received from the plurality of access points;

wherein the wireless transceiver is further adapted to transmit the location estimate of the bed, as determined by the controller, to other beds.

2. The location detection system of claim 1 wherein the messages include a media access control (MAC) address for each of the access points.

3. The location detection system of claim 2 wherein the wireless transceiver wirelessly communicates with the plurality of access points in accordance with Institute of Electrical and Electronics Engineers (IEEE) standard 802.11.

4. The location detection system of claim 1 further comprising an infrared receiver adapted to receive an infrared signal from a fixed locator positioned off of the bed, the infrared signal including a locator identifier unique to the fixed locator, and wherein the wireless transceiver transmits the locator identifier to one of the access points.

5. The location detection system of claim 1 wherein the controller is positioned on the bed.

6. A location detection system comprising:

a bed having a frame, a support surface adapted to support a person thereon, and a wireless transceiver adapted to wirelessly communicate with a plurality of access points of a hospital computer network, the wireless transceiver adapted to transmit bed status information to the hospital computer network and to receive messages from the plurality of access points;

a processing station located remotely from the bed and communicatively coupled to the hospital computer network, the processing station adapted to access data indicating locations of each of the plurality of access points; and a controller on board the bed, the controller adapted to send to the processing station signal strength data of the messages, wherein the processing station generates a location estimate of the bed within a hospital based upon the signal strength data and the data indicating locations of each of the plurality of access points.

7. The location detection system of claim 6 wherein the controller is adapted to send the signal strength data to the processing station using the wireless transceiver, and wherein the processing station includes map data indicating locations of the access points within the hospital.

8. The location detection system of claim 7 wherein the hospital computer network is an Ethernet-based computer network.

9. The location detection system of claim 6 further comprising:

an infrared transceiver supported on the bed, the infrared transceiver adapted to transmit an interrogation signal; and a plurality of locators positioned at fixed locations, each of the locators adapted to wirelessly transmit a unique identifier in response to the interrogation signal from the infrared transceiver; and wherein the controller is adapted to send the unique identifier to the processing station, the processing station being further adapted to generate a location estimate of the bed within the hospital based upon the unique identifier.

10. The location detection system of claim 9 wherein the processing station is further adapted to generate a location estimate of at least one of the access points based upon the location estimate of the bed and the signal strength data.

11. The location detection system of claim 9 wherein the processing station is adapted to access data indicating locations of each of the plurality of access points, to generate a first location estimate of the bed based upon the signal strength data and the data indicating locations of each of the plurality of access points, and to generate a second location estimate of the bed based upon the unique identifier.

12. The location detection system of claim 11 wherein the processing station is further adapted to generate a third location estimate of the bed by combining the first and second location estimates.

13. The location detection system of claim 11 wherein the processing station is further adapted to forward at least one of the first and second location estimates to a second processing station communicatively coupled to the hospital computer network.

14. The location detection system of claim 13 wherein the processing station forwards the first location estimate to the second processing station if the bed is moving, and the processing station forwards the second location estimate to the second processing station if the bed is stationary and positioned adjacent to one of the locators.

15. The location detection system of claim 13 wherein the processing station forwards the first location estimate to the second processing station if the bed has a brake off; and the processing station forwards the second location estimate to the second processing station if the bed has the brake on.

16. The location detection system of claim 6 wherein the processing station is adapted to transmit the location estimate of the bed to the bed.

17. The location detection system of claim 16 wherein the controller is adapted to transmit the location estimate of the bed wirelessly to another device.

18. A person support apparatus comprising:

a frame;

a support surface adapted to support a person thereon;

a wireless transceiver adapted to wirelessly communicate with a plurality of access points of a computer network, the wireless transceiver adapted to receive messages from the plurality of access points;

a sensor adapted to wirelessly communicate with a locator positioned at a fixed location within a hospital; and a controller adapted to determine in which room of the hospital the person support apparatus is located based upon data from the messages and to determine in which zone of the room the person support apparatus is located based on communication between the sensor and the locator.

19. The person support apparatus of claim 18 wherein the controller is further adapted to transmit the room and zone to a processing station located remotely from the person support apparatus and communicatively coupled to the computer network.

20. The person support apparatus of claim 18 wherein the controller determines the room based upon signal strength data of the messages when a brake on the person support apparatus is off.

21. The person support apparatus of claim 20 wherein the messages further include a media access control (MAC) address for each of the access points.

22. The person support apparatus of claim 21 wherein the wireless transceiver wirelessly communicates with the plurality of access points in accordance with Institute of Electrical and Electronics Engineers (IEEE) standard 802.11, and the sensor is adapted to receive an electromagnetic signal from the locator.

23. A person support apparatus comprising:
a frame;
a support surface adapted to support a person thereon;
a first wireless transceiver adapted to wirelessly communicate with a plurality of access points of a computer network, the first wireless transceiver adapted to receive messages from the plurality of access points;
a second wireless transceiver adapted to wirelessly communicate with a locator positioned at a fixed location within a facility, the second wireless transceiver adapted to receive a unique identifier from the locator;
a memory in which map data indicating a location of the locator is stored; and
a controller adapted to determine signal strength data of the messages, to wirelessly receive location data from another person support apparatus that is in communication with at least one of the access points, and to generate a location estimate of the at least one of the access points of the computer network based upon the unique identifier, the map data, the location data, and the signal strength data.

24. The person support apparatus of claim 23 wherein the controller is further adapted to wirelessly transmit the location estimate to another person support apparatus that is in communication with the at least one of the access points.

25. The person support apparatus of claim 24 wherein the first wireless transceiver wirelessly communicates with the plurality of access points in accordance with Institute of Electrical and Electronics Engineers (IEEE) standard 802.11, and the second wireless transceiver is an infrared receiver adapted to receive an infrared signal from the locator.

* * * * *